US012673983B1

(12) United States Patent
Groff et al.

(10) Patent No.: US 12,673,983 B1
(45) **Date of Patent: *Jul. 7, 2026**

(54) ***E. COLI* STRAINS FOR PRODUCING FULL-LENGTH ANTIBODIES**

(71) Applicant: Sutro Biopharma, Inc., South San Francisco, CA (US)

(72) Inventors: Daniel Groff, Alameda, CA (US); Jeffrey Hanson, Oakland, CA (US)

(73) Assignee: Sutro Biopharma. Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/231,362

(22) Filed: Jun. 6, 2025

Related U.S. Application Data

(63) Continuation of application No. 17/244,893, filed on Apr. 29, 2021, now Pat. No. 12,351,850.

(60) Provisional application No. 63/018,436, filed on Apr. 30, 2020.

(51) Int. Cl.
*C12N 15/70* (2006.01)
*C07K 16/00* (2006.01)

(52) U.S. Cl.
CPC .............. *C07K 16/00* (2013.01); *C12N 15/70* (2013.01)

(58) Field of Classification Search
CPC ..... C12P 21/02; C07K 16/2878; C07K 16/00; C07K 2317/14; C07K 16/3092; C07K 2317/622; C12N 15/70; C12N 9/1252; C12Y 108/01007; C12Y 207/07007
USPC .......................................................... 435/69.1
See application file for complete search history.

(56) References Cited

U.S. PATENT DOCUMENTS

| | | | |
|---|---|---|---|
| 4,816,397 | A | 3/1989 | Boss |
| 8,288,148 | B2 | 10/2012 | Cervin |
| 8,574,869 | B2 | 11/2013 | Kao et al. |
| 8,685,668 | B2 | 4/2014 | Minea et al. |
| 8,802,394 | B2 | 8/2014 | Minea et al. |
| 8,852,886 | B2 | 10/2014 | Dubois et al. |
| 8,877,916 | B2 | 11/2014 | Alexandrov |
| 9,416,388 | B2 | 8/2016 | Ruddock et al. |
| 9,976,164 | B2 | 5/2018 | Ruddock |
| 10,093,704 | B2 | 10/2018 | Oganesyan et al. |
| 10,465,197 | B2 | 11/2019 | Mcclain et al. |
| 11,407,975 | B2 | 8/2022 | Groff |
| 2008/0206818 | A1 | 8/2008 | Wich et al. |
| 2019/0112357 | A1 | 4/2019 | Ahuja et al. |
| 2020/0172915 | A1 | 6/2020 | McClain et al. |

FOREIGN PATENT DOCUMENTS

| | | | |
|---|---|---|---|
| CN | 104837863 | A | 8/2015 |
| EP | 3360960 | A1 | 8/2018 |
| JP | 2015-510392 | A | 4/2015 |
| JP | 2020-014392 | A | 1/2020 |
| JP | 2022-513017 | A | 2/2022 |
| WO | 2011100362 | A1 | 8/2011 |
| WO | 2013/096925 | A1 | 6/2013 |
| WO | 2013/185115 | A1 | 12/2013 |
| WO | 2016/187466 | A1 | 11/2016 |
| WO | 2017/093254 | A1 | 6/2017 |
| WO | 2019/055931 | A1 | 3/2019 |

OTHER PUBLICATIONS

Nowroozi et al., Appl. Microbiol. Biotechnol, 2014, vol. 98: 1567-1581.*

Vo et al., (Authorea, vol. 2, Jul. 2020, pp. 1-14.*

Ayyar et al., ("Optimizing antibody expression: The nuts and bolts". Methods, vol. 116, Mar. 1, 2017.*

Gaciarz et al., "Systematic screening of soluble expression of antibody fragments in the cytoplasm of *E. coli*," Microb Cell Fact, (2016), 15(22):1-10.

Gaciarz et al., "Efficient soluble expression of disulfide bonded proteins in the cytoplasm of *Escherichia coli* in fed-batch fermentations on chemically defined minimal media", Microbial Cell Factories, vol. 16, No. 108, 2017, 12 pages.

Kaur et al., "Strategies for Optimization of Heterologous Protein Expression in *E. coli:* Roadblocks and Reinforcements", International Journal of Biological Macromolecules, vol. 106, 2018, pp. 803-822.

Lobstein et al., "SHuffle, A Novel *Escherichia coli* Protein Expression Strain Capable of Correctly Folding Disulfide Bonded Proteins in its Cytoplasm", Microbial Cell Factories, vol. 11, No. 1, 2012, 16 pages.

Robinson et al, "Efficient expression of full-length antibodies in the cytoplasm of engineered bacteria," Nature Communications, Aug. 27, 2015, 9 pages, DOI: 10.1038/ncomms9072.

Robinson, Michael-Paul "Remodeling Antibodies from the Inside Out: Functional Engineering of Full-Length Antibodies in the Cytoplasm of Bacteria," Ph.D. Dissertation, Cornell University, (Dec. 2017), 149 pages.

PCT/US2019/060345 , "International Search Report and Written Opinion", Mar. 24, 2020, 12 pages.

Ayyar, et al., "Optimizing antibody expression: The nuts and bolts", Methods, vol. 116, Mar. 1, 2017 (Mar. 1, 2017), pp. 51-62, XP055621465, NL ISSN: 1046-2023, DOI: 10.1016/j.ymeth.2017.01.009.

Reddy, et al., "Platform development for expression and purification of stable isotope labeled monoclonal antibodies in *Escherichia coli*", mAbs, Jul. 30, 2018 (Jul. 30, 2018), pp. 1-11, XP055825272, USISSN: 1942-0862, DOI: 10.1080/19420862.2018.1496879 Retrieved from the Internet: URL:https:// www.tandfonline.com/doi/pdf/10.1080/19420862.2018.1496879?needAccess=true.

(Continued)

*Primary Examiner* — Tekchand Saidha
*Assistant Examiner* — Mohammad Y Meah
(74) *Attorney, Agent, or Firm* — Kilpatrick Townsend & Stockton LLP

(57) ABSTRACT

This disclosure provides methods and compositions related to producing full-length antibodies in *E. coli* having an oxidative cytoplasm, which is helpful for maintaining the three-dimensional structure and stability of proteins having disulfide bonds. The *E. coli* is used to produce full length antibody in high yield.

25 Claims, 14 Drawing Sheets

Specification includes a Sequence Listing.

(56) References Cited

OTHER PUBLICATIONS

Reilly, et al., “Production of Monoclonal Antibodies in *E. coli*”, Jan. 1, 2010 (Jan. 1, 2010), Current Trends In Monoclonal Antibody Development And Manufacturing, Springer, US, pp. 295-308, XP009143519, ISBN: 978-0-387-76642-3.

Wals, et al., “Unnatural amino acid incorporation in *E. coli:* current and future applications in the design of therapeutic proteins”, Frontiers in Chemistry, vol. 2, Apr. 1, 2014 (Apr. 1, 2014), pp. 1-12, XP055826160, DOI: 10.3389/fchem.2014.00015 Retrieved from the Internet: URL:https://www.ncbi.nlm.nih.gov/pmc/articles/PMC3982533/pdf/fchem-02-00015.pdf.

Anonymous: “Novagen—pET-21 a-d( +) Vectors”, Dec. 1, 1998 (Dec. 1, 1998), XP055825703, Retrieved from the Internet: URL:https://www.helmholtz-muenchen.de/fileadmin/PEPF/pET vectors/pET-21 a-d_MAP .pdf [retrieved on Jul. 19, 2021], 2 pages.

Monje-Casas, et al., “Expression Analysis of the nrdHIEF Operon from Escherichia coli,” The Journal Of Biological Chemistry, vol. 276(21), pp. 18031-18037, Feb. 2001.

PCT/US2021/030115, “International Search Report and Written Opinion”, mailed Jul. 30, 2021, 24 pages.

Robinson et al., “Efficient expression of full-length antibodies in the cytoplasm of engineered bacteria”, Nature Communications, vol. 6, No. 8072, pp. 1-9 (Aug. 27, 2015).

Novagen, “pET-21a-d(+) Vectors”, (Feb. 20, 2025), pp. 1-2, Internet <URL: http://www.synthesisgene.com/vector/pET-21a.pdf>, [search date: Feb. 20, 2025], upload date: unknown.

Qiagen, “CompactPrep(TM) Plasmid Mega/Giga Purification Handbook”, pp. 1-36, Internet <URL: https://www.qiagen.com/US/resources/download.aspx?id=53e36633-f2bb-4ad3-92b1-93c9b1da9159&lang=en>, [search date: Feb. 20, 2025] (Jan. 2008).

Kessler et al., Expression, purification, and isotope labeling of the Fv of the human H IV-1 neutralizing antibody 447-52D for NM R studies. Prot. Express. Purification., 2003, vol. 29: 291-303. (Year: 2003).

Lee et al., Enhanced production of human full-length immunoglobulin G1 in the periplasm of *Escherichia coli.* Appl. Microbial. Biotechnol., 2014, vol. 98: 1237-1246. (Year: 2014).

Simmons et al., Translational level is a critical factor for the secretion of heterologous proteins in *Escherichia coli.* Nat. Biotechnol., 1996, vol. 14: 629-634. (Year: 1996).

Simmons et al., Expression of full-length immunoglobulins in *Escherichia coli:* rapid and efficient production of aglycosylated antibodies. J. Immunol. Methods., 2002, vol. 263: 133-147. (Year: 2002).

Li et al., Sutro Biopharma, Poster AACR, 2018. (Year: 2018).

Nowroozi et al., Metabolic pathway optimization using ribosome binding site variants and combinatorial gene assembly. Appl. Microbial. Biotechnol, 2014, vol. 98: 1567-1581. (Year: 2014).

Vo et al., Optimized expression of Hfq protein increases *Escherichia coli* growth by enhancing acid resistance. Authorea, vol. 2, Jul. 2020, pp. 1-14. (Year: 2020).

Axup et al ( Synthesis of site specific antibody-drug conjugates using unnatural amino acids. Proceedings to the National Academy of Sciences vol. 109, No. 40, 2 Oct. 12, 2012. (Year: 2012).

Makino et al., “Comprehensive engineering of *Escherichia coli* for enhanced expression of IgG antibodies”, Metabolic Engineering, vol. 13, No. 2 (Mar. 2011), pp. 241-251.

Roy et al., “Development of a high yielding expression platform for the introduction of non-natural amino acids in protein sequences”, mAbs, vol. 12, No. 1 (Nov. 27, 2019), e1684749.

* cited by examiner (1)

(2)

(3)

(4)

(5)

(6)

(7)

(8)

(9)

(10)

(11)

(12)

(13)

(14)

(15)

(16)

(17)

(18)

(19)

(20)

(21)

(22)

(23)

(24)

(25)

(26)

(27)

(28)

(29)

and
(30)

(31)

(32)

(33)

(34)

(35)

(36)

(37)

(38)

(39)

(40)

(41)

(42)

(43)

SEQUENCE LISTING

```
Sequence total quantity: 38
SEQ ID NO: 1           moltype = AA  length = 455
FEATURE                Location/Qualifiers
REGION                 1..455
                       note = Description of Artificial Sequence: Synthetic
                        polypeptide
source                 1..455
                       mol_type = protein
                       organism = synthetic construct
SEQUENCE: 1
MEVQLVESGG GLVQPGGSLR LSCAASGFNT TTKSIHWVRQ APGKGLEWVG EIYPRDGITD  60
YADSVKGRFT ISADTSKNTA YLQMNSLRAE DTAVYYCARG GWHWRSGYSY YLDYWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
ELLGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSREEMTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPGK                              455

SEQ ID NO: 2           moltype = AA  length = 215
FEATURE                Location/Qualifiers
REGION                 1..215
                       note = Description of Artificial Sequence: Synthetic
                        polypeptide
source                 1..215
                       mol_type = protein
                       organism = synthetic construct
SEQUENCE: 2
MDIQMTQSPS SLSASVGDRV TITCRASQDV NTAVAWYQQK PGKAPKLLIY SASFLYSGVP  60
SRFSGSRSGT DFTLTISSLQ PEDFATYYCQ QHYTTPPTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                              215

SEQ ID NO: 3           moltype = AA  length = 455
FEATURE                Location/Qualifiers
REGION                 1..455
                       note = Description of Artificial Sequence: Synthetic
                        polypeptide
SITE                   412
```

```
                        note = Non-natural amino acid
VARIANT                 412
                        note = Non-natural amino acid
source                  1..455
                        mol_type = protein
                        organism = synthetic construct
SEQUENCE: 3
MEVQLVESGG GLVQPGGSLR LSCAASGFNT TTKSIHWVRQ APGKGLEWVG EIYPRDGITD  60
YADSVKGRFT ISADTSKNTA YLQMNSLRAE DTAVYYCARG GWHWRSGYSY YLDYWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
ELLGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSREEMTKNQ VSLTCLVKGF YPSDIAVEWE SNGQPENNYK TTPPVLDSDG SXFLYSKLTV  420
DKSRWQQGNV FSCSVMHEAL HNHYTQKSLS LSPGK                             455

SEQ ID NO: 4            moltype = AA  length = 455
FEATURE                 Location/Qualifiers
REGION                  1..455
                        note = Description of Artificial Sequence: Synthetic
                         polypeptide
SITE                    188
                        note = Non-natural amino acid
VARIANT                 188
                        note = Non-natural amino acid
source                  1..455
                        mol_type = protein
                        organism = synthetic construct
SEQUENCE: 4
MEVQLVESGG GLVQPGGSLR LSCAASGFNT TTKSIHWVRQ APGKGLEWVG EIYPRDGITD  60
YADSVKGRFT ISADTSKNTA YLQMNSLRAE DTAVYYCARG GWHWRSGYSY YLDYWGQGTL  120
VTVSSASTKG PSVFPLAPSS KSTSGGTAAL GCLVKDYFPE PVTVSWNSGA LTSGVHTFPA  180
VLQSSGLXSL SSVVTVPSSS LGTQTYICNV NHKPSNTKVD KKVEPKSCDK THTCPPCPAP  240
ELLGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSREEMTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPGK                             455

SEQ ID NO: 5            moltype = AA  length = 215
FEATURE                 Location/Qualifiers
REGION                  1..215
                        note = Description of Artificial Sequence: Synthetic
                         polypeptide
SITE                    43
                        note = Non-natural amino acid
VARIANT                 43
                        note = Non-natural amino acid
source                  1..215
                        mol_type = protein
                        organism = synthetic construct
SEQUENCE: 5
MDIQMTQSPS SLSASVGDRV TITCRASQDV NTAVAWYQQK PGXAPKLLIY SASFLYSGVP  60
SRFSGSRSGT DFTLTISSLQ PEDFATYYCQ QHYTTPPTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 6            moltype = AA  length = 455
FEATURE                 Location/Qualifiers
REGION                  1..455
                        note = Description of Artificial Sequence: Synthetic
                         polypeptide
SITE                    188
                        note = Non-natural amino acid
SITE                    412
                        note = Non-natural amino acid
VARIANT                 188
                        note = Non-natural amino acid
VARIANT                 412
                        note = Non-natural amino acid
source                  1..455
                        mol_type = protein
                        organism = synthetic construct
SEQUENCE: 6
MEVQLVESGG GLVQPGGSLR LSCAASGFNT TTKSIHWVRQ APGKGLEWVG EIYPRDGITD  60
YADSVKGRFT ISADTSKNTA YLQMNSLRAE DTAVYYCARG GWHWRSGYSY YLDYWGQGTL  120
VTVSSASTKG PSVFPLAPSS KSTSGGTAAL GCLVKDYFPE PVTVSWNSGA LTSGVHTFPA  180
VLQSSGLXSL SSVVTVPSSS LGTQTYICNV NHKPSNTKVD KKVEPKSCDK THTCPPCPAP  240
ELLGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
```

```
PSREEMTKNQ VSLTCLVKGF YPSDIAVEWE SNGQPENNYK TTPPVLDSDG SXFLYSKLTV  420
DKSRWQQGNV FSCSVMHEAL HNHYTQKSLS LSPGK                             455

SEQ ID NO: 7            moltype = AA  length = 455
FEATURE                 Location/Qualifiers
REGION                  1..455
                        note = Description of Artificial Sequence: Synthetic
                         polypeptide
SITE                    249
                        note = Non-natural amino acid
VARIANT                 249
                        note = Non-natural amino acid
source                  1..455
                        mol_type = protein
                        organism = synthetic construct
SEQUENCE: 7
MEVQLVESGG GLVQPGGSLR LSCAASGFNT TTKSIHWVRQ APGKGLEWVG EIYPRDGITD  60
YADSVKGRFT ISADTSKNTA YLQMNSLRAE DTAVYYCARG GWHWRSGYSY YLDYWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
ELLGGPSVXL FPPKPKDTLM ISRTPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSREEMTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPGK                             455

SEQ ID NO: 8            moltype = AA  length = 455
FEATURE                 Location/Qualifiers
REGION                  1..455
                        note = Description of Artificial Sequence: Synthetic
                         polypeptide
SITE                    188
                        note = Non-natural amino acid
SITE                    412
                        note = Non-natural amino acid
VARIANT                 188
                        note = Non-natural amino acid
VARIANT                 412
                        note = Non-natural amino acid
source                  1..455
                        mol_type = protein
                        organism = synthetic construct
SEQUENCE: 8
MEVQLVESGG GLVQPGGSLR LSCAASGFNI RTQSIHWVRQ APGKGLEWIG DIFPIDGITD  60
YADSVKGRFT ISADTSKNTA YLQMNSLRAE DTAVYYCARG SWSWPSGMDY YLDYWGQGTL  120
VTVSSASTKG PSVFPLAPSS KSTSGGTAAL GCLVKDYFPE PVTVSWNSGA LTSGVHTFPA  180
VLQSSGLXSL SSVVTVPSSS LGTQTYICNV NHKPSNTKVD KKVEPKSCDK THTCPPCPAP  240
ELLGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSREEMTKNQ VSLTCLVKGF YPSDIAVEWE SNGQPENNYK TTPPVLDSDG SXFLYSKLTV  420
DKSRWQQGNV FSCSVMHEAL HNHYTQKSLS LSPGK                             455

SEQ ID NO: 9            moltype = AA  length = 215
FEATURE                 Location/Qualifiers
REGION                  1..215
                        note = Description of Artificial Sequence: Synthetic
                         polypeptide
source                  1..215
                        mol_type = protein
                        organism = synthetic construct
SEQUENCE: 9
MDIQMTQSPS SVSASVGDRV TITCRASQGI GSWLAWYQQK PGKAPKLLIY AADRLQSGVP  60
SRFSGSGSGT DFTLTISSLQ PEDFATYYCQ QYHTYPLTFG GGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 10           moltype = AA  length = 454
FEATURE                 Location/Qualifiers
REGION                  1..454
                        note = Description of Artificial Sequence: Synthetic
                         polypeptide
SITE                    411
                        note = Non-natural amino acid
VARIANT                 411
                        note = Non-natural amino acid
source                  1..454
                        mol_type = protein
                        organism = synthetic construct
SEQUENCE: 10
MQVQLVESGG GVVQPGRSLR LSCAASGFNF SDYGMHWVRQ APGKGLEWVA VIWYDGSISY  60
```

-continued

```
YADSVKGRFT ISRDNSKNTL YLQMNSLRAE DTAVYYCARG GTVEHGAVYG TDVWGQGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS XFLYSKLTVD  420
KSRWQQGNVF SCSVMHEALH NHYTQKSLSL SPGK                              454

SEQ ID NO: 11          moltype = AA  length = 450
FEATURE                Location/Qualifiers
REGION                 1..450
                       note = Description of Artificial Sequence: Synthetic
                        polypeptide
source                 1..450
                       mol_type = protein
                       organism = synthetic construct
SEQUENCE: 11
MEVQLVQSGA EVKKPGASVK VSCKASGYTF DSYGISWVRQ APGQGLEWMG WISAYNGNTN  60
YAQKLQGRVT MTTDTSTNTA YMELRSLRSD DTAVYYCARD VDYGTGSGYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCEVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 12          moltype = AA  length = 215
FEATURE                Location/Qualifiers
REGION                 1..215
                       note = Description of Artificial Sequence: Synthetic
                        polypeptide
source                 1..215
                       mol_type = protein
                       organism = synthetic construct
SEQUENCE: 12
MSYELTQPPS VSVSPGQTAR ITCSGDALPK QYAYWYQQKP GQAPVMVIYK DTERPSGIPE  60
RFSGSSSGTK VTLTISGVQA EDEADYYCQS ADNSITYRVF GGGTKVTVLG QPKAAPSVTL  120
FPPSSEELQA NKATLVCLIS DFYPGAVTVA WKADSSPVKA GVETTTPSKQ SNNKYAASSY  180
LSLTPEQWKS HRSYSCQVTH EGSTVEKTVA PTECS                             215

SEQ ID NO: 13          moltype = AA  length = 452
FEATURE                Location/Qualifiers
REGION                 1..452
                       note = Description of Artificial Sequence: Synthetic
                        polypeptide
source                 1..452
                       mol_type = protein
                       organism = synthetic construct
SEQUENCE: 13
MEVQLVESGG GLVQPGGSLR LSCAASGFNI DRYYIHWVRQ APGKGLEWVA GITPVRGYTE  60
YADSVKDRFT ISADTSKNTA YLQMNSLRAE DTAVYYCARG YVYRMWDSYD YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCEVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 14          moltype = AA  length = 215
FEATURE                Location/Qualifiers
REGION                 1..215
                       note = Description of Artificial Sequence: Synthetic
                        polypeptide
source                 1..215
                       mol_type = protein
                       organism = synthetic construct
SEQUENCE: 14
MDIQMTQSPS SLSASVGDRV TITCRASQDV NTAVAWYQQK PGKAPKLLIY SASFLYSGVP  60
SRFSGSRSGT DFTLTISSLQ PEDFATYYCQ QHYTTPPTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 15          moltype = AA  length = 453
FEATURE                Location/Qualifiers
REGION                 1..453
                       note = Description of Artificial Sequence: Synthetic
                        polypeptide
source                 1..453
                       mol_type = protein
```

-continued

```
                       organism = synthetic construct
SEQUENCE: 15
MQVQLVESGG GVVQPGRSLR LSCAASGFTF SSYGMHWVRQ APGKGLEWVA VIWYDGSYKY  60
YADSVKGRFT ISRDNSKNTL YLQMNSLRAE DTAVYYCARE EAPENWDYAL DVWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCEVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 16          moltype = AA  length = 216
FEATURE                Location/Qualifiers
REGION                 1..216
                       note = Description of Artificial Sequence: Synthetic
                        polypeptide
source                 1..216
                       mol_type = protein
                       organism = synthetic construct
SEQUENCE: 16
MEIVLTQSPG TLSLSPGERA TLSCRASQSV SSSYLAWYQQ KPGQAPRLLI YGASSRATGI  60
PDRFSGSGSG TDFTLTISRL EPEDFAVYYC QQYGRSPFSF GPGTKVDIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                           216

SEQ ID NO: 17          moltype =   length =
SEQUENCE: 17
000

SEQ ID NO: 18          moltype =   length =
SEQUENCE: 18
000

SEQ ID NO: 19          moltype =   length =
SEQUENCE: 19
000

SEQ ID NO: 20          moltype =   length =
SEQUENCE: 20
000

SEQ ID NO: 21          moltype =   length =
SEQUENCE: 21
000

SEQ ID NO: 22          moltype =   length =
SEQUENCE: 22
000

SEQ ID NO: 23          moltype =   length =
SEQUENCE: 23
000

SEQ ID NO: 24          moltype = AA  length = 455
FEATURE                Location/Qualifiers
REGION                 1..455
                       note = Description of Artificial Sequence: Synthetic
                        polypeptide
source                 1..455
                       mol_type = protein
                       organism = synthetic construct
SEQUENCE: 24
MEVQLVESGG GLVQPGGSLR LSCAASGFNI RTQSIHWVRQ APGKGLEWIG DIFPIDGITD  60
YADSVKGRFT ISADTSKNTA YLQMNSLRAE DTAVYYCARG SWSWPSGMDY YLDYWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
ELLGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSREEMTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPGK                            455

SEQ ID NO: 25          moltype = AA  length = 454
FEATURE                Location/Qualifiers
REGION                 1..454
                       note = Description of Artificial Sequence: Synthetic
                        polypeptide
source                 1..454
                       mol_type = protein
                       organism = synthetic construct
```

-continued

```
SEQUENCE: 25
MQVQLVESGG GVVQPGRSLR LSCAASGFNF SDYGMHWVRQ APGKGLEWVA VIWYDGSISY  60
YADSVKGRFT ISRDNSKNTL YLQMNSLRAE DTAVYYCARG GTVEHGAVYG TDVWGQGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPGK                             454

SEQ ID NO: 26           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 26
taatacgact cactataggg                                             20

SEQ ID NO: 27           moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 27
MEVQLVESGG GLVQPGGSLR LSCAASGFNI KDTYIHWVRQ APGKGLEWVA RIYPTNGYTR  60
YADSVKGRFT ISADTSKNTA YLQMNSLRAE DTAVYYCSRW GGDGFYAMDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 28           moltype =   length =
SEQUENCE: 28
000

SEQ ID NO: 29           moltype =   length =
SEQUENCE: 29
000

SEQ ID NO: 30           moltype = DNA  length = 89
FEATURE                 Location/Qualifiers
misc_feature            1..89
                        note = Description of Artificial Sequence: Synthetic
                         oligonucleotide
source                  1..89
                        mol_type = other DNA
                        organism = synthetic construct
SEQUENCE: 30
taattgtgag cggataacaa ttacgagctt catgcacagt gaaatcatga aaaatttatt  60
tgctttgtga gcggataaca attataata                                   89

SEQ ID NO: 31           moltype = DNA  length = 13
FEATURE                 Location/Qualifiers
misc_feature            1..13
                        note = Description of Artificial Sequence: Synthetic
                         oligonucleotide
source                  1..13
                        mol_type = other DNA
                        organism = synthetic construct
SEQUENCE: 31
aaggaggtaa aaa                                                    13

SEQ ID NO: 32           moltype = DNA  length = 13
FEATURE                 Location/Qualifiers
misc_feature            1..13
                        note = Description of Artificial Sequence: Synthetic
                         oligonucleotide
source                  1..13
                        mol_type = other DNA
                        organism = synthetic construct
SEQUENCE: 32
```

```
aggagatata cat                                                  13

SEQ ID NO: 33          moltype = DNA  length = 13
FEATURE                Location/Qualifiers
misc_feature           1..13
                       note = Description of Artificial Sequence: Synthetic
                        oligonucleotide
source                 1..13
                       mol_type = other DNA
                       organism = synthetic construct
SEQUENCE: 33
aagagatata cat                                                  13

SEQ ID NO: 34          moltype = DNA  length = 13
FEATURE                Location/Qualifiers
misc_feature           1..13
                       note = Description of Artificial Sequence: Synthetic
                        oligonucleotide
source                 1..13
                       mol_type = other DNA
                       organism = synthetic construct
SEQUENCE: 34
aaaagatata cat                                                  13

SEQ ID NO: 35          moltype = DNA  length = 2054
FEATURE                Location/Qualifiers
misc_feature           1..2054
                       note = Description of Artificial Sequence: Synthetic
                        polynucleotide
source                 1..2054
                       mol_type = other DNA
                       organism = synthetic construct
SEQUENCE: 35
aaggaggtaa aaaatggaca ttcaaatgac ccagtctccg tcgtcactgt ccgcatccgt  60
tggcgaccgc gttaccatca cgtgccgtgc gtcgcaagat gtgaacaccg ccgtggcgtg  120
gtatcagcaa aaaccgggca aagctccgaa gctgctgatc tattcagcct ctttcctgta  180
ctcgggtgtt ccgtcccgtt tctcaggctc tcgctcgggt acggatttca ccctgactat  240
ttcttcactg caaccggaag attttgcgac gtactactgt cagcagcatt acacgactcc  300
gccgaccttt ggtcagggta ccaaggtcga gattaagcgt accgtggctg caccatccgt  360
gtttatcttc cctccgtctg atgagcagct gaaatccggt acggcgtcgg tcgtctgctt  420
gctgaataac ttctatccgc gtgaagcgaa ggtgcaatgg aaggttgaca atgccctgca  480
gtcaggtaac tcccaagagt ctgttaccga acaagattcg aaagactcaa cctactccct  540
gtcttcgacg ctgacgttgt ccaaagcgga ctatgagaaa cacaaggttt acgcatgtga  600
agtgacccac cagggcctgt catctccggt caccaaatca tttaatcgcg gtgagtgcta  660
aacccctta agaaggagat atacatatgg aagttcaatt agtcgagtct ggtggcggct  720
tagttcaacc tggtggttca ttgcgtctgt cttgcgctgc atcgggtttt aacaccacca  780
cgaaatccat tcattgggtg cgccaggccc caggtaaagg cctggaatgg gtcggcgaga  840
tctacccgcg tgacggtatt acggattatg cggattcggt gaagggtcgc ttcaccatct  900
ccgcggatac tagcaagaat accgcgtatc tgcagatgaa ctctctgcgt gcagaggaca  960
ccgcggtcta ctactgtgcc cgtggcggct ggcactggcg ctcgggttat tcatactatc  1020
tggactactg gggtcagggt acgttggtta ccgtgtcatc cgcgtcaacc aagggtccgt  1080
cggtttttcc gctggcgccg tcgtcaaaat ctacgtccgg tggtaccgcc gctctgggtt  1140
gcctggttaa agactacttt ccggagccgg tcacggtttc gtggaactct ggtgccctga  1200
cttctggcgt ccacacgttc ccagccgttt tgcagtcatc cggtctgtac tcgttgtcct  1260
ctgtggtcac ggtgccgtca tcgtctctgg gcacccaaac ctatatctgc aatgtcaacc  1320
acaaaccgtc caatacgaaa gttgacaaaa aagtcgagcc gaaatcttgc gacaagaccc  1380
acacgtgccc tccgtgcccg gcaccggaac tgctgggcgg tccgtcggtg ttcctgttcc  1440
cgccgaagcc gaaagatact ctgatgatct cacgtacccc ggaagtcacg tgtgttgttg  1500
ttgacgtgtc acacgaagat ccagaggtga aattcaattg gtatgtggac ggtgtcgaag  1560
tgcataatgc caaaaccaaa ccgcgcgagg aacagtacaa ctccacctac cgcgtcgtgt  1620
cggtgttgac cgtcctgcat caagactggc tgaacggtaa agagtacaag tgcaaggttt  1680
caaataaggc actgcctgcg ccgattgaaa agaccatctc taaggcaaag ggccagccgc  1740
gtgagccaca ggtgtatacc ctgccgccgt cgcgtgaaga aatgaccaag aaccaagttt  1800
cactgacgtg tctggtcaag ggcttttatc cgtccgatat tgcggtggag tgggagtcta  1860
atggccagcc ggaaaacaat tacaaaacga ctccgccggt gctggattcc gacggttcgt  1920
ttttcctgta ttccaagctg accgttgaca aatcacgttg gcagcaaggc aacgtttttt  1980
cttgttcggt aatgcacgaa gcgctgcaca atcattacac ccagaaatca ctgtcgttgt  2040
ctccgggcaa ataa                                                 2054

SEQ ID NO: 36          moltype = DNA  length = 2348
FEATURE                Location/Qualifiers
misc_feature           1..2348
                       note = Description of Artificial Sequence: Synthetic
                        polynucleotide
source                 1..2348
                       mol_type = other DNA
                       organism = synthetic construct
SEQUENCE: 36
aaggaggtaa aaaatggaca ttcaaatgac ccagtctccg tcgtcactgt ccgcatccgt  60
```

```
tggcgaccgc gttaccatca cgtgccgtgc gtcgcaagat gtgaacaccg ccgtggcgtg  120
gtatcagcaa aaaccgggca aagctccgaa gctgctgatc tattcagcct ctttcctgta  180
ctcgggtgtt ccgtcccgtt tctcaggctc tcgctcgggt acggatttca ccctgactat  240
ttcttcactg caaccggaag attttgcgac gtactactgt cagcagcatt acacgactcc  300
gccgaccttt ggtcagggta ccaaggtcga gattaagcgt accgtggctg caccatccgt  360
gtttatcttc cctccgtctg atgagcagct gaaatccggt acggcgtcgg tcgtctgctt  420
gctgaataac ttctatccgc gtgaagcgaa ggtgcaatgg aaggttgaca atgccctgca  480
gtcaggtaac tcccaagagt ctgttaccga acaagattcg aaagactcaa cctactccct  540
gtcttcgacg ctgacgttgt ccaaagcgga ctatgagaaa cacaaggttt acgcatgtga  600
agtgacccac cagggcctgt catctccggt caccaaatca tttaatcgcg gtgagtgcta  660
acccccctagc ataacccctt ggggcctcta aacgggtctt gaggggtttt ttgcccctga  720
gacgcgtcaa tcgagttcgt acctaagggc gacaccccct aattagcccg gatttttttt  780
gcgaaattaa tacgactcac tatagggaga ccacaacggt ttccctctag aaataatttt  840
gtttaacttt aagaaggagat atacatatgg aagttcaatt agtcgagtct ggtggcggct  900
tagttcaacc tggtggttca ttgcgtctgt cttgcgctgc atcgggtttt aacaccacca  960
cgaaatccat tcattgggtg cgccaggccc caggtaaagg cctggaatgg gtcggcgaga  1020
tctacccgcg tgacggtatt acggattatg cggattcggt gaagggtcgc ttcaccatct  1080
ccgcggatac tagcaagaat accgcgtatc tgcagatgaa ctctctgcgt gcagaggaca  1140
ccgcggtcta ctactgtgcc cgtggcggct ggcactggcg ctcgggttat tcatactatc  1200
tggactactg gggtcagggt acgttggtta ccgtgtcatc cgcgtcaacc aagggtccgt  1260
cggtttttcc gctggcgccg tcgtcaaaat ctacgtccgg tggtaccgcc gctctgggtt  1320
gcctggttaa agactacttt ccggagccgg tcacggtttc gtggaactct ggtgccctga  1380
cttctggcgt ccacacgttc ccagccgttt tgcagtcatc cggtctgtac tcgttgtcct  1440
ctgtggtcac ggtgccgtca tcgtctctgg gcacccaaac ctatatctgc aatgtcaacc  1500
acaaaccgtc caatacgaaa gttgacaaaa aagtcgagcc gaaatcttgc gacaagaccc  1560
acacgtgccc tccgtgcccg gcaccggaac tgctgggcgg tccgtcggtg ttcctgttcc  1620
cgccgaagcc gaaagatact ctgatgatct cacgtacccc ggaagtcacg tgtgttgttg  1680
ttgacgtgtc acacgaagat ccagaggtga aattcaattg gtatgtggac ggtgtcgaag  1740
tgcataatgc caaaaccaaa ccgcgcgagg aacagtacaa ctccacctac cgcgtcgtgt  1800
cggtgttgac cgtcctgcat caagactggc tgaacggtaa agagtacaag tgcaaggttt  1860
caaataaggc actgcctgcg ccgattgaaa agaccatctc taaggcaaag ggccagccgc  1920
gtgagccaca ggtgtatacc ctgccgccgt cgcgtgaaga aatgaccaag aaccaagttt  1980
cactgacgtg tctggtcaag ggcttttatc cgtccgatat tgcggtggag tgggagtcta  2040
atggccagcc ggaaaacaat tacaaaacga ctccgccggt gctggattcc gacggttcgt  2100
ttttcctgta ttccaagctg accgttgaca aatcacgttg gcagcaaggc aacgtttttt  2160
cttgttcggt aatgcacgaa gcgctgcaca atcattacac ccagaaatca ctgtcgttgt  2220
ctccgggcaa ataatgagtc gaccggctgc taacaaagcc cgaaaggaag ctgagttggc  2280
tgctgccacc gctgagcaat aactagcata accccttggg gcctctaaac gggtcttgag  2340
gggttttt                                                          2348
```

```
SEQ ID NO: 37          moltype = DNA  length = 2348
FEATURE                Location/Qualifiers
misc_feature           1..2348
                       note = Description of Artificial Sequence: Synthetic
                        polynucleotide
source                 1..2348
                       mol_type = other DNA
                       organism = synthetic construct
SEQUENCE: 37
aaggaggtaa aaaatggaca ttcaaatgac ccagtctccg tcgtcactgt ccgcatccgt  60
tggcgaccgc gttaccatca cgtgccgtgc gtcgcaagat gtgaacaccg ccgtggcgtg  120
gtatcagcaa aaaccgggca aagctccgaa gctgctgatc tattcagcct ctttcctgta  180
ctcgggtgtt ccgtcccgtt tctcaggctc tcgctcgggt acggatttca ccctgactat  240
ttcttcactg caaccggaag attttgcgac gtactactgt cagcagcatt acacgactcc  300
gccgaccttt ggtcagggta ccaaggtcga gattaagcgt accgtggctg caccatccgt  360
gtttatcttc cctccgtctg atgagcagct gaaatccggt acggcgtcgg tcgtctgctt  420
gctgaataac ttctatccgc gtgaagcgaa ggtgcaatgg aaggttgaca atgccctgca  480
gtcaggtaac tcccaagagt ctgttaccga acaagattcg aaagactcaa cctactccct  540
gtcttcgacg ctgacgttgt ccaaagcgga ctatgagaaa cacaaggttt acgcatgtga  600
agtgacccac cagggcctgt catctccggt caccaaatca tttaatcgcg gtgagtgcta  660
acccccctagc ataacccctt ggggcctcta aacgggtctt gaggggtttt ttgcccctga  720
gacgcgtcaa tcgagttcgt acctaagggc gacaccccct aattagcccg gatttttttt  780
gcgaaattaa tacgactcac tatagggaga ccacaacggt ttccctctag aaataatttt  840
gtttaacttt aagaaggagat atacatatgg aagttcaatt agtcgagtct ggtggcggct  900
tagttcaacc tggtggttca ttgcgtctgt cttgcgctgc atcgggtttt aacaccacca  960
cgaaatccat tcattgggtg cgccaggccc caggtaaagg cctggaatgg gtcggcgaga  1020
tctacccgcg tgacggtatt acggattatg cggattcggt gaagggtcgc ttcaccatct  1080
ccgcggatac tagcaagaat accgcgtatc tgcagatgaa ctctctgcgt gcagaggaca  1140
ccgcggtcta ctactgtgcc cgtggcggct ggcactggcg ctcgggttat tcatactatc  1200
tggactactg gggtcagggt acgttggtta ccgtgtcatc cgcgtcaacc aagggtccgt  1260
cggtttttcc gctggcgccg tcgtcaaaat ctacgtccgg tggtaccgcc gctctgggtt  1320
gcctggttaa agactacttt ccggagccgg tcacggtttc gtggaactct ggtgccctga  1380
cttctggcgt ccacacgttc ccagccgttt tgcagtcatc cggtctgtac tcgttgtcct  1440
ctgtggtcac ggtgccgtca tcgtctctgg gcacccaaac ctatatctgc aatgtcaacc  1500
acaaaccgtc caatacgaaa gttgacaaaa aagtcgagcc gaaatcttgc gacaagaccc  1560
acacgtgccc tccgtgcccg gcaccggaac tgctgggcgg tccgtcggtg ttcctgttcc  1620
cgccgaagcc gaaagatact ctgatgatct cacgtacccc ggaagtcacg tgtgttgttg  1680
ttgacgtgtc acacgaagat ccagaggtga aattcaattg gtatgtggac ggtgtcgaag  1740
tgcataatgc caaaaccaaa ccgcgcgagg aacagtacaa ctccacctac cgcgtcgtgt  1800
```

-continued

```
cggtgttgac cgtcctgcat caagactggc tgaacggtaa agagtacaag tgcaaggttt  1860
caaataaggc actgcctgcg ccgattgaaa agaccatctc taaggcaaag ggccagccgc  1920
gtgagccaca ggtgtatacc ctgccgccgt cgcgtgaaga aatgaccaag aaccaagttt  1980
cactgacgtg tctggtcaag ggcttttatc cgtccgatat tgcggtggag tgggagtcta  2040
atggccagcc ggaaaacaat tacaaaacga ctccgccggt gctggattcc gacggttcgt  2100
ttttcctgta ttccaagctg accgttgaca aatcacgttg gcagcaaggc aacgtttttt  2160
cttgttcggt aatgcacgaa gcgctgcaca atcattacac ccagaaatca ctgtcgttgt  2220
ctccgggcaa ataatgagtc gaccggctgc taacaaagcc cgaaaggaag ctgagttggc  2280
tgctgccacc gctgagcaat aactagcata accccttggg gcctctaaac gggtcttgag  2340
gggtttt                                                            2348

SEQ ID NO: 38          moltype = DNA  length = 2348
FEATURE                Location/Qualifiers
misc_feature           1..2348
                       note = Description of Artificial Sequence: Synthetic
                        polynucleotide
source                 1..2348
                       mol_type = other DNA
                       organism = synthetic construct
SEQUENCE: 38
aaggaggtaa aaaatggaca ttcaaatgac ccagtctccg tcgtcactgt ccgcatccgt  60
tggcgaccgc gttaccatca cgtgccgtgc gtcgcaagat gtgaacaccg ccgtggcgtg  120
gtatcagcaa aaaccgggca aagctccgaa gctgctgatc tattcagcct ctttcctgta  180
ctcgggtgtt ccgtcccgtt tctcaggctc tcgctcgggt acggatttca ccctgactat  240
ttcttcactg caaccggaag attttgcgac gtactactgt cagcagcatt acacgactcc  300
gccgaccttt ggtcagggta ccaaggtcga gattaagcgt accgtggctg caccatccgt  360
gtttatcttc cctccgtctg atgagcagct gaaatccggt acggcgtcgg tcgtctgctt  420
gctgaataac ttctatccgc gtgaagcgaa ggtgcaatgg aaggttgaca atgccctgca  480
gtcaggtaac tcccaagagt ctgttaccga acaagattcg aaagactcaa cctactccct  540
gtcttcgacg ctgacgttgt ccaaagcgga ctatgagaaa cacaaggttt acgcatgtga  600
agtgacccac cagggcctgt catctccggt caccaaatca tttaatcgcg gtgagtgcta  660
accccctagc ataacccctt ggggcctcta aacgggtctt gaggggtttt ttgcccctga  720
gacgcgtcaa tcgagttcgt acctaagggc gacaccccct aattagcccg gatttttttt  780
gcgaaattaa tacgactcac tatagggaga ccacaacggt ttccctctag aaataatttt  840
gtttaacttt aagaaaagat atacatatgg aagttcaatt agtcgagtct ggtggcggct  900
tagttcaacc tggtggttca ttgcgtctgt cttgcgctgc atcgggtttt aacaccacca  960
cgaaatccat tcattgggtg cgccaggccc caggtaaagg cctggaatgg gtcggcgaga  1020
tctacccgcg tgacggtatt acggattatg cggattcggt gaagggtcgc ttcaccatct  1080
ccgcggatac tagcaagaat accgcgtatc tgcagatgaa ctctctgcgt gcagaggaca  1140
ccgcggtcta ctactgtgcc cgtggcggct ggcactggcg ctcgggttat tcatactatc  1200
tggactactg gggtcagggt acgttggtta ccgtgtcatc cgcgtcaacc aagggtccgt  1260
cggtttttcc gctggcgccg tcgtcaaaat ctacgtccgg tggtaccgcc gctctgggtt  1320
gcctggttaa agactacttt ccggagccgg tcacggtttc gtggaactct ggtgccctga  1380
cttctggcgt ccacacgttc ccagccgttt tgcagtcatc cggtctgtac tcgttgtcct  1440
ctgtggtcac ggtgccgtca tcgtctctgg gcacccaaac ctatatctgc aatgtcaacc  1500
acaaaccgtc caatacgaaa gttgacaaaa aagtcgagcc gaaatcttgc gacaagaccc  1560
acacgtgccc tccgtgcccg gcaccggaac tgctgggcgg tccgtcggtg ttcctgttcc  1620
cgccgaagcc gaaagatact ctgatgatct cacgtacccc ggaagtcacg tgtgttgttg  1680
ttgacgtgtc acacgaagat ccagaggtga aattcaattg gtatgtggac ggtgtcgaag  1740
tgcataatgc caaaaccaaa ccgcgcgagg aacagtacaa ctccacctac cgcgtcgtgt  1800
cggtgttgac cgtcctgcat caagactggc tgaacggtaa agagtacaag tgcaaggttt  1860
caaataaggc actgcctgcg ccgattgaaa agaccatctc taaggcaaag ggccagccgc  1920
gtgagccaca ggtgtatacc ctgccgccgt cgcgtgaaga aatgaccaag aaccaagttt  1980
cactgacgtg tctggtcaag ggcttttatc cgtccgatat tgcggtggag tgggagtcta  2040
atggccagcc ggaaaacaat tacaaaacga ctccgccggt gctggattcc gacggttcgt  2100
ttttcctgta ttccaagctg accgttgaca aatcacgttg gcagcaaggc aacgtttttt  2160
cttgttcggt aatgcacgaa gcgctgcaca atcattacac ccagaaatca ctgtcgttgt  2220
ctccgggcaa ataatgagtc gaccggctgc taacaaagcc cgaaaggaag ctgagttggc  2280
tgctgccacc gctgagcaat aactagcata accccttggg gcctctaaac gggtcttgag  2340
gggtttt                                                            2348
```

*E. COLI* STRAINS FOR PRODUCING FULL-LENGTH ANTIBODIES

SEQUENCE LISTING

The instant application contains a Sequence Listing which has been submitted electronically in XML format and is hereby incorporated by reference in its entirety. Said XML Sequence Listing, created on Jun. 18, 2025, is named 091200-1510590-006820US_ST26.xml and is 63,078 bytes in size.

BACKGROUND OF THE INVENTION

Full-length antibodies play major roles in treating a wide variety of human diseases. As the demand for antibody therapeutics increases, the development of host systems for enhanced and less expensive production of the full-length antibodies has also become more important. Almost all therapeutic antibodies approved to date are predominantly produced in mammalian hosts; these production methods have drawbacks such as high production cost and long-term cultivation. Alternative production systems such as bacteria and yeasts have been considered. Still, these systems have their own limitations. For example, the proteins produced in these systems often require refolding and secretion across several biological membranes and lack disulfide bonds that are essential for maintaining the three-dimensional form of the antibodies. Also, it remains a challenge to express the heavy chain and light chain of the same antibody in appropriate ratios to ensure the heterotetramer form of the full-length antibodies can be produced in maximum yield. Thus, there remains a need for producing full-length antibodies in high yield in order to meet the demand for commercial production.

SUMMARY OF INVENTION

This disclosure provides a method to produce a full-length antibody comprising a heavy chain (HC) and a light chain (LC) in high yield. The method comprises culturing *E. coli* cells expressing a coding sequence for the HC and a coding sequence for the LC under conditions permissible for producing the HC and LC, and the full-length antibody can be produced in an amount of at least 200 mg/L. In some embodiments, the full-length antibody is produced at a wet weight percentage in a range from 0.05% to 20%, from 0.05% to 10%, from 0.05% to 5%, or from 0.05% to 1% relative to the weight of wet cell pellet produced from the *E. coli* cells in the culture.

In some embodiments, at least some of the *E. coli* cells contain an oxidative cytoplasm. In some embodiments, the method comprises transforming the plasmid to the *E. coli* strain. In some embodiments, the HC and LC are produced in the cytoplasm of the *E. coli*. In some embodiments, the method further comprises assembling the produced HC and LC under non-reducing conditions to form the full-length antibody. In some embodiments, the molar ratio of the produced HC and the produced LC from the *E. coli* is 1:1 to 1:3.

In some embodiments, expression of HC, LC, or both is controlled by a promoter, for example, a T7 promoter or a promoter that has substantially similar promoter strength as the T7 promoter. In some embodiments, the plasmid comprises a biscistronic operon, wherein the bicistronic operon comprises the coding sequence for the HC and the coding sequence for the LC. The bicistronic operon may comprise a promoter that drives expression of both the HC and LC, and the promoter is a T7 promoter or a promoter that has substantially similar promoter strength as the T7 promoter. In some embodiments, the bicistronic operon comprises a T7 terminator. In some embodiments, the plasmid encoding the HC and LC comprises a first monocistronic operon for the HC and a second monocistronic operon for LC. In some embodiments, the first operon comprises a ribosomal binding site that comprises a sequence selected from any of SEQ ID NO: 18-20 and the second monocistronic operon comprises a ribosomal binding site comprising the sequence of SEQ ID NO: 17. In some embodiments, the first monocistronic operon or the second monocistronic operon each independently comprise a T7 promoter or a promoter that has substantially similar promoter strength as the T7 promoter. In some embodiments, the first or second monocistronic operon each independently comprise a T5 promoter, or a promoter that has substantially similar promoter strength as the T5 promoter. In some embodiments, the first and second monocistronic operons comprise the same promoter. In some embodiments, the first and second monocistronic operons comprise different promoters.

*E. coli* cell may comprise a first ribosome-binding site for translation of the HC and a second ribosomal binding site for translation of the LC, wherein the first and second ribosomal binding sites are selected such that the molar ratio of HC and LC produced from the *E. coli* ranges from 1:1 to 1:3. In some embodiments, the first ribosomal binding site comprises a sequence selected from the group consisting of SEQ ID NO: 17-19, and the second ribosomal binding site comprises a sequence that is selected from the group consisting of SEQ ID NO: 20-23. In some embodiments, the first ribosomal binding site comprises a sequence of SEQ ID NO: 17 or SEQ ID NO: 18.

In some embodiments, the HC and/or the LC of the full-length antibody comprises at least one non-natural amino acid. For example, the non-natural amino acid can be para-methylazido-L-phenylalanine (pAMF), AEK, or pAcF. For example, the coding sequence of the HC and/or the coding sequence of the LC can be modified to have at least one non-natural amino acid codon, and the non-natural amino acid codon that does not result in incorporation of one of the 20 naturally occurring amino acids. The at least one non-natural amino acid may be introduced by charging a tRNA that contains anticodons that are complementary to the at least one non-natural amino acid codon, e.g., the amber codon (TAG). In some embodiments, the codon that is immediately 3' to at least one of the non-natural amino acid is codon optimized to boost the expression of the HC or LC.

In certain embodiments, the full-length antibody that can be produced using the methods is a B10 antibody, an H01 antibody, a 7219 antibody, an anti-PD1 antibody, an anti HER2 antibody (e.g., trastuzumab), an anti-Tim3 antibody, or an anti LAG3 antibody. In some embodiments, the coding sequence for the HC of the B10 antibody contains a mutation relative to SEQ ID NO: 1, wherein the mutation results in a codon for a natural amino acid is being substituted with a non-natural amino acid codon, and the natural amino acid being substituted is one or more amino acids selected from F412, Y188, and F249. A non-natural amino acid can be introduced to the HC or the LC by charging a tRNA that is complementary to the non-natural amino acid codon. In some embodiments, the coding sequence for the LC of the B10 antibody or the anti HER2 antibody contains a mutation relative to SEQ ID NO: 2, wherein the mutation results in a codon for a natural amino acid is being substituted with a non-natural amino acid codon, wherein the natural amino acid is K43 or E162.

In some embodiments, the method of producing a full length FolRa-B10 IgG antibody comprises transforming an *E. coli* host strain with a construct expressing FolRa-B10 IgG, where the S181 codon of the HC encoding sequence is AGC or AGT.

In some embodiments, the method further comprises covalently linking a warhead moiety to the non-natural amino acid on the HC or the LC of the full-length antibody via a linker.

BRIEF DESCRIPTION TO THE DRAWINGS

Figure 5:
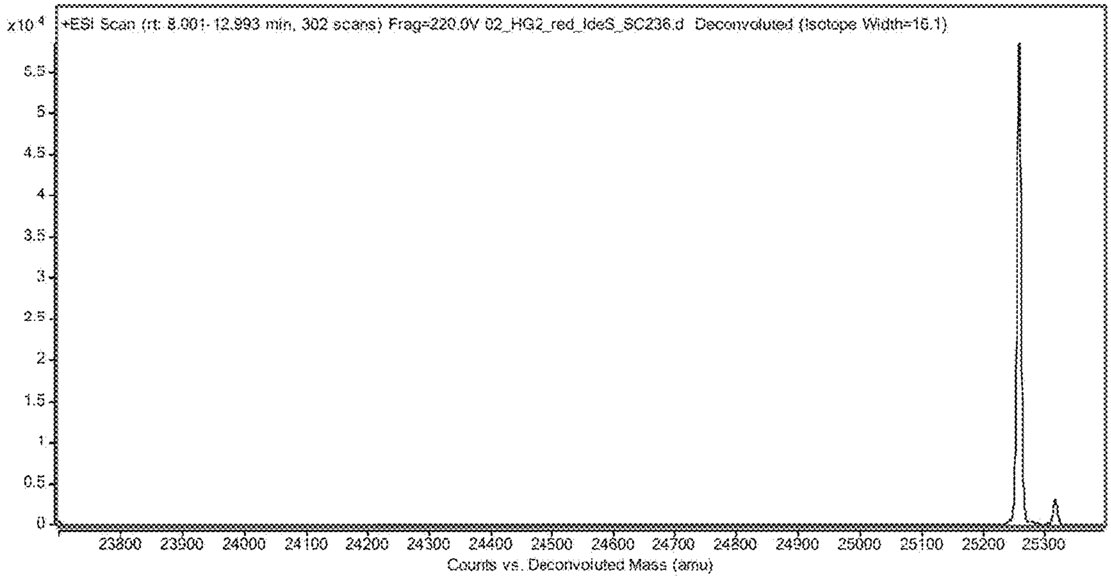

FIG. 5 shows the results of deconvoluted LCMS spectra for Fc-fragment of B10 F412pAMF that is conjugated to the DBCO-maytansine drug-linker SC236. The predominant species observed has a mass of 25257.97 Da compared with the theoretical mass of 25258.04 Da for the conjugate. No species were observed near 23974.14 Da, the theoretical mass for the unconjugated Fc fragment. This conjugate has a calculated conjugation efficiency of 99.997%.

Figure 6:
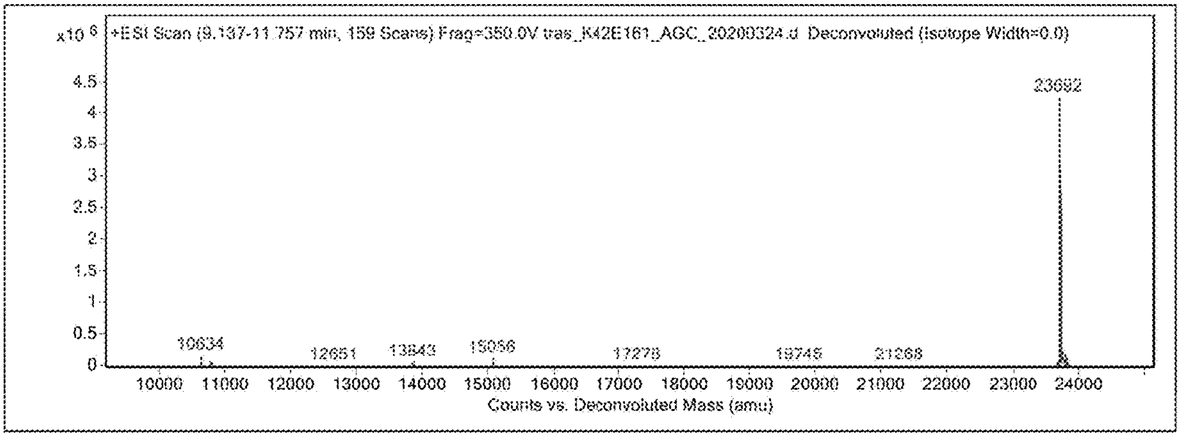

FIG. 6 shows the results of LCMS of purified trastuzumab LC K43pAcPhe E162pAcPhe run in positive ionization mode. There is one clean peak corresponding to the expected mass for the 2× pAcPhe LC product.

Figure 7:
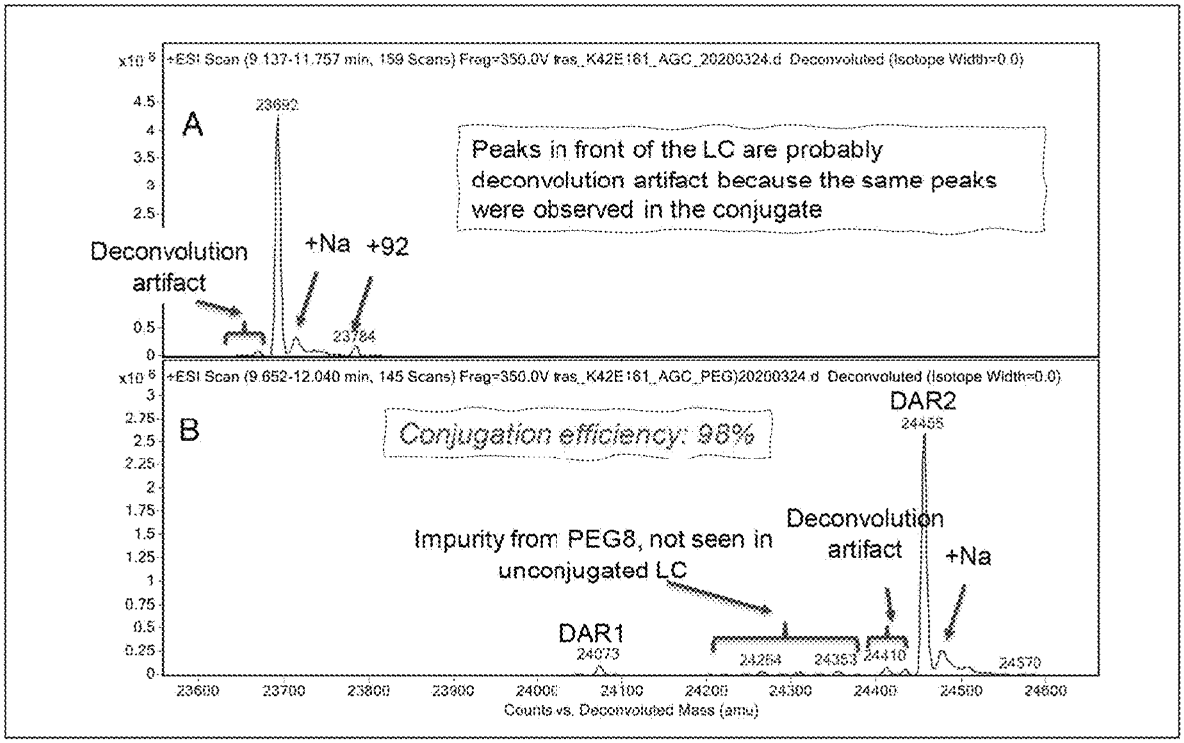
Figure 8A:
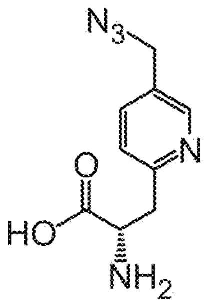
Figure 8A:
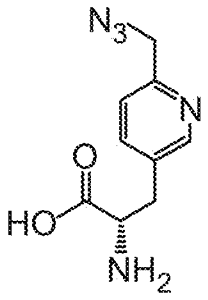
Figure 8A:
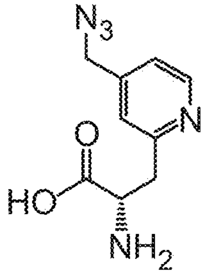
Figure 8A:
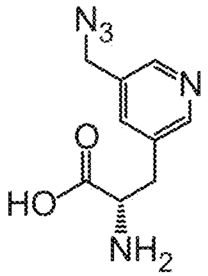
Figure 8A:
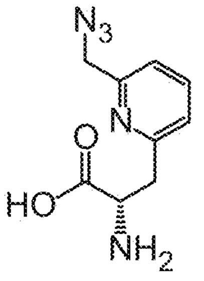
Figure 8B:
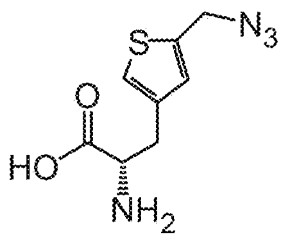
Figure 8B:
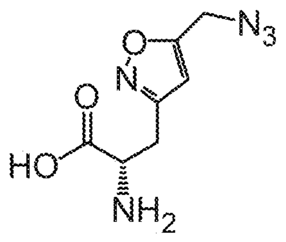
Figure 8B:
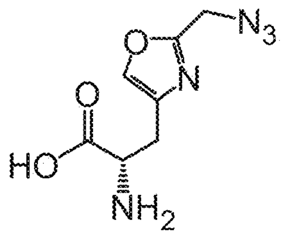
Figure 8B:
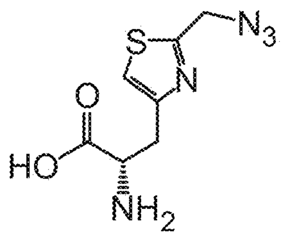
Figure 8B:
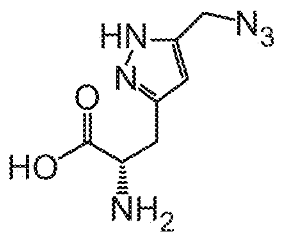
Figure 8C:
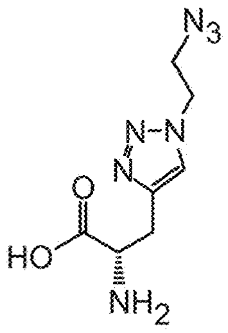
Figure 8C:
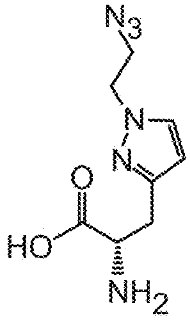
Figure 8C:
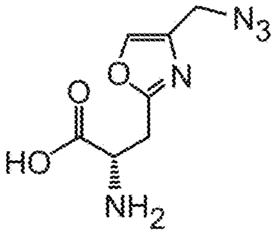
Figure 8C:
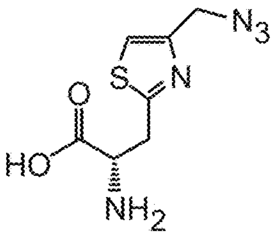
Figure 8C:
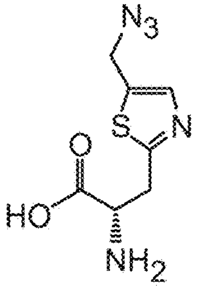
Figure 8D:
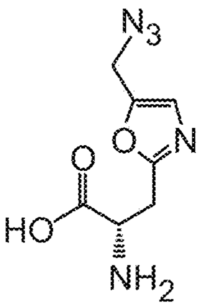
Figure 8D:
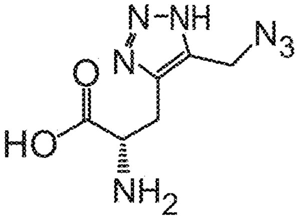
Figure 8D:
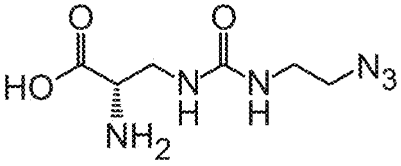
Figure 8D:
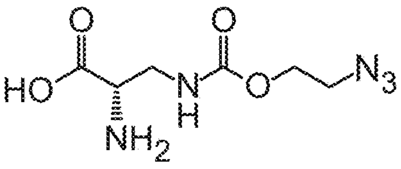
Figure 8D:
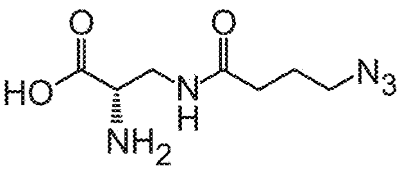
Figure 8E:
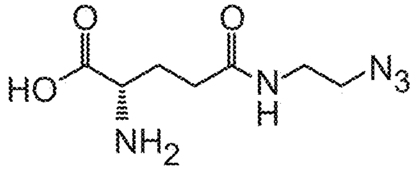
Figure 8E:
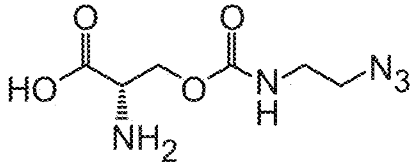
Figure 8E:
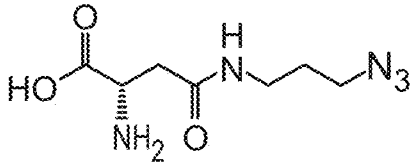
Figure 8E:
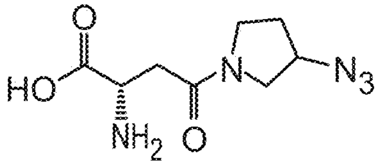
Figure 8E:
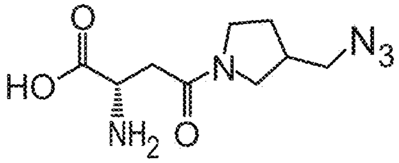
Figure 8F:
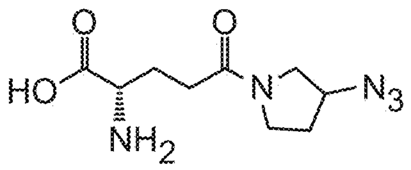
Figure 8F:
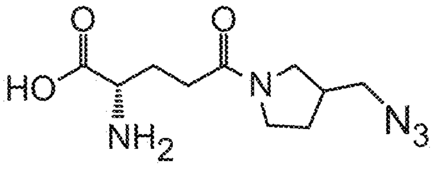
Figure 8F:
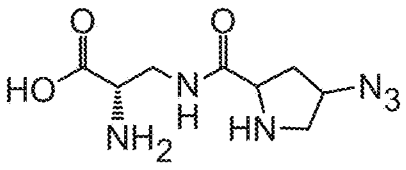
Figure 8F:
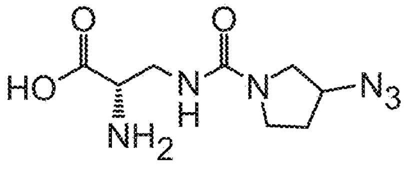
Figure 8F:
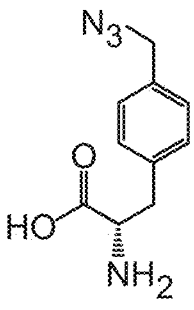
Figure 8F:
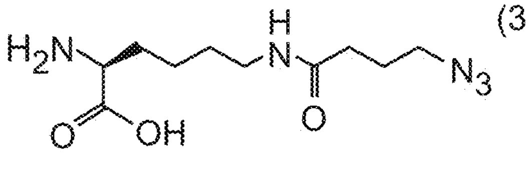
Figure 8G:
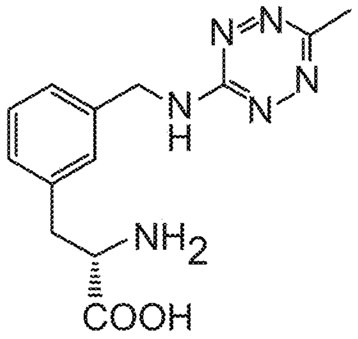
Figure 8G:
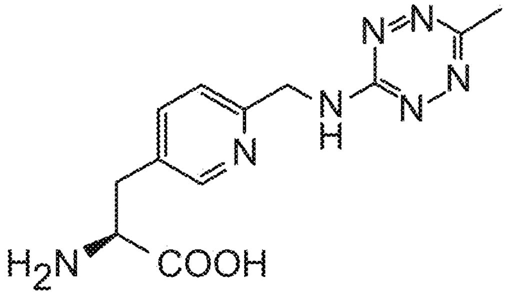
Figure 8G:
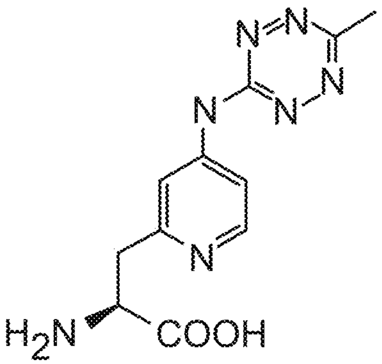
Figure 8G:
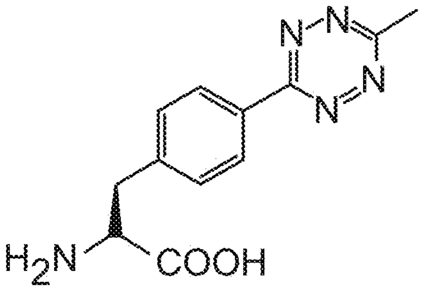
Figure 8H:
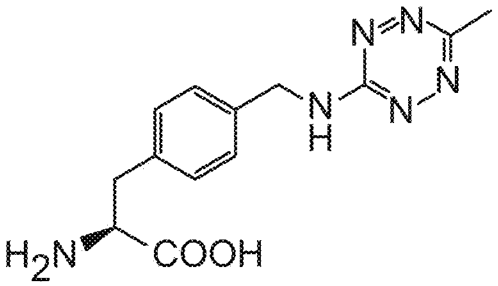
Figure 8H:
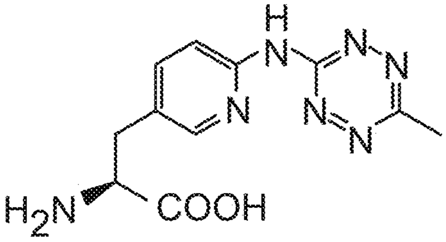
Figure 8H:
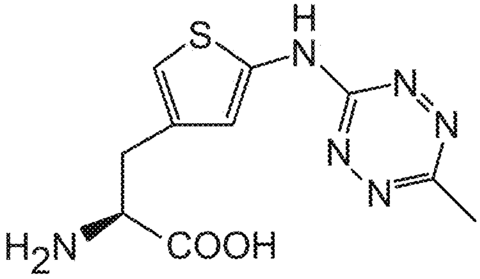
Figure 8H:
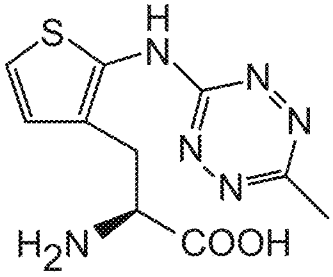
Figure 8I:
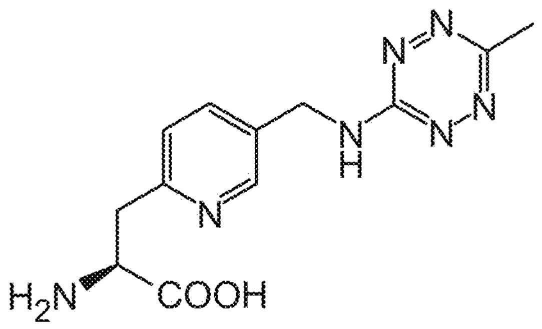
Figure 8I:
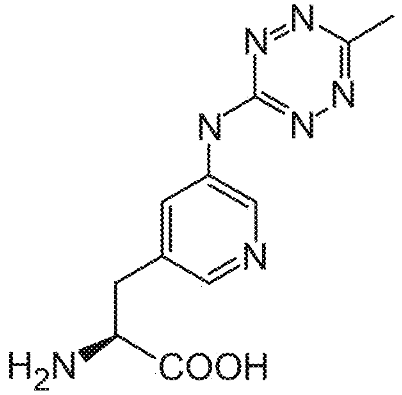
Figure 8I:
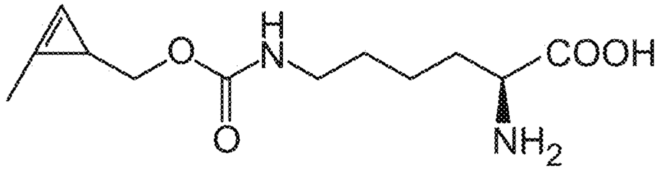
Figure 8I:
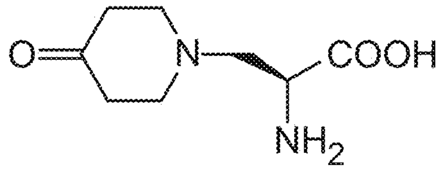

FIG. 7 shows the results of the LCMS of purified trastuzumab LC K43pAcPhe E162pAcPhe after oxime ligation with PEG8-alkoxy amine, run in positive ionization mode. Conjugation efficiency was calculated using peaks at 23692, 24073 and 24455 AMUs which correspond to the expected mass for the 0, 1 and 2 PEG8 products respectively. A) shows LC before oxime ligation and B) after oxime ligation. The calculated conjugation efficiency was around 98%.

FIG. 8A-8I show exemplary non-natural amino acids that can be used in the methods disclosed herein.

DETAILED DESCRIPTION OF THE INVENTION

I. Introduction

This disclosure provides methods of producing a full-length antibody by expressing both the heavy chain (HC) and the light chain (LC) of the antibody in *E. coli* cells. The method of the present invention utilizes a combination of features that allow the production of full-length antibodies in high yield, e.g., at a concentration of greater than 200 mg of protein per liter of culture medium.

The *E. coli* cells typically have an oxidative cytoplasm, which helps the formation of the disulfide bonds that are required to maintain the three-dimensional structure and stability of the antibody. The methods employ a strong promoter to drive the transcription of the HC, the LC, or both. In some embodiments, the promoter is a T7 promoter or a T5 promoter. In some cases, the strength of the promoter is substantially similar to that of the T7 promoter or the T5 promoter. In some cases, the methods employ optimized ribosomal binding sites to ensure efficient translation and/or assembly of the HC and LC of the antibodies.

The inventors have found that maintaining the proportional expression of the heavy chain (HC) and light chain (LC), i.e. the ratio of the amount of expression of the HC and LC within an optimal range, can increase the yield of the full-length and properly assembled antibody. For example, it is desirable to maintain the molar ratio of the produced HC and LC from the *E. coli* culture within a suitable range, e.g., from 1:1 to 1:3, from 1:1 to 1:2.5, or from 1:1 to 1:2. In some approaches, maintaining the expression of the HC and LC within the optimal range ratio is achieved by using one or two promoters that can control the transcription level of HC and LC. In some approaches, the proportional expression of the HC and LC in the *E. coli* culture is achieved by using modified ribosomal binding sites to control the translation efficiency of the HC and LC. Exemplary ribosomal binding sequences are provided herein.

In some approaches, at least one of the HC and the LC coding sequence is modified to comprise at least one non-natural amino acid codon (e.g., an amber codon), provided that the non-natural amino acid codon does not result in incorporation of one of the 20 naturally occurring amino acids. These non-natural amino acids may serve as potential reactive groups for conjugating with one or more biologically active adducts in a site-specific manner.

This disclosure incorporates the entire content of the International Application No., PCT/US2019/060345 by reference.

II. Definition

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, NY 1989); Ausubel et al., CURRENT PROTOCOLS IN MOLECULAR BIOLOGY, John Wiley and Sons (Hoboken, NY 1995).

As used herein the singular forms "a," "and," and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

The term "about" denotes a range of −/+10% of a reference value, e.g., "about 10," means 10−/+10×10%=9-11.

Unless explicitly stated otherwise, the terms "yield" or "titer" refer to the amount of antibody produced (including the total amount of HC and LC) relative to the culture medium volume. For example, 200 mg/L refers to 200 mg of antibody produced per liter of culture medium.

The term "*E. coli* strain" refers to a subtype of *E. coli*, the cells of which have a certain biological form and share certain genetic makeup. The term "*E. coli* strain having oxidative cytoplasm" refers to that some or all of the cells derived from the strain each have an oxidative cytoplasm.

The term "amino acids" refers to naturally occurring and non-naturally occurring amino acids, as well as amino acids such as proline, amino acid analogs, and amino acid mimetics that function in a manner similar to naturally occurring amino acids.

The term "naturally occurring amino acids" or "naturally encoded amino acids" refer to the proteinogenic amino acids known to those of skill in the art. They include the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and the less common pyrrolysine and selenocysteine. Naturally encoded amino acids include post-translational variants of the 22 naturally occurring amino acids such as prenylated amino acids, isoprenylated amino acids, myrisoylated amino acids, palmitoylated amino acids, N-linked glycosylated amino acids, O-linked glycosylated amino acids, phosphorylated amino acids, and acylated amino acids.

The term "non-natural amino acid" refers to an amino acid that is not a proteinogenic amino acid or a post-translationally modified variant thereof. In particular, the term refers to an amino acid that is not one of the 20 common amino acids, pyrrolysine, selenocysteine, or post-translationally modified variants thereof.

The term "aminoacylation" or "aminoacylate" refers to the complete process in which a tRNA is charged with its correct amino acid that is a result of adding an aminoacyl group to a compound. As it pertains to this invention, a tRNA that undergoes aminoacylation or has been aminoacylated is one that has been charged with an amino acid, and an amino acid that undergoes aminoacylation or has been aminoacylated is one that has been charged to a tRNA molecule.

The term "aminoacyl-tRNA synthetase" or "tRNA synthetase" or "synthetase" or "aaRS" or "RS" refers to an enzyme that catalyzes a covalent linkage between an amino acid and a tRNA molecule. This results in an aminoacylated tRNA molecule, which is a tRNA molecule that has its respective amino acid attached via an ester bond.

The term "charged" in the context of tRNA refers to the aminoacylation of a tRNA with an amino acid, both natural and non-natural, where the aminoacylation permits a ribosome to incorporate the amino acid into a polypeptide being translated from mRNA.

The term "biologically active adduct" refers to a chemical, molecule or reagent that can perform a function in a cell or an organism. For example, the function may include cell proliferation, apoptosis, post-translational modification (e.g., phosphorylation), cell signaling activation, cell signaling inactivation, cell death, or cell labeling.

The term "selective incorporating" in the context of protein translation refers to including or introducing a specific amino acid (e.g., a specific non-natural amino acid) in a predetermined, desired amino acid position in the sequence of the protein without disturbing the desired function of the protein.

The term "preferentially aminoacylates" refers to the preference of a tRNA synthtase to aminoacylate (charge) a particular tRNA molecule with a predetermined amino acid molecule compared to another amino acid molecule. In other words, the tRNA synthtase can selectively aminoacylate a non-natural amino acid (nnAA) over a naturally occurring amino acid. For example, the tRNA synthtase can aminoacylate a specific nnAA at a frequency of greater than 90%, (e.g., 91%, 92%, 93%, 94%, 95%, 96%, 97%, 98%, 99%, or 100%), compared to any or all other natural amino acids.

The term "naturally occurring amino acid" refers to any one of the 20 amino acids encoded by the genetic code, such as arginine, Arg, R; histidine, His, H; lysine, Lys, K; aspartic acid, Asp, D; glutamic acid, Glu, E; serine, S, Ser; threonine, Thr, T; asparagine, Asn, N; glutamine, Gln, Q; cysteine, Cys, G; glycine, Gly, G; proline, Pro, P; alanine, Ala, A; isoleucine, Ile, I; leucine, Leu, L; methionine, Met, M; phenylalanine, Phe, F; tryptophan, Trp, W; tyrosine, Tyr, Y; and valine, Val, V, that are precursors to proteins.

Amino acids may be referred to herein by either the commonly known three-letter symbols or by the one-letter symbols recommended by the IUPAC-IUB Biochemical Nomenclature Commission. Nucleotides, likewise, may be referred to by their commonly accepted single-letter codes.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid or polynucleotide is used interchangeably with gene, cDNA, and mRNA encoded by a gene.

The term "peptide," "protein," and "polypeptide" are used herein interchangeably and refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins and truncated proteins, wherein the amino acid residues are linked by covalent peptide bonds.

The term "substitution at amino acid position" refers to a change of an amino acid residue at a specific position of the amino acid sequence of a protein. For example, the term "X20Y" refers to the replacement of the wild-type (reference) amino acid X at amino acid position 20 of the protein with the amino acid Y.

The term "suppression codon" refers to a nucleotide triplet that is introduced into a polynucleotide at a predetermined location and is recognized by a specific tRNA that can recognize a stop codon (e.g., an amber, ochre or opal stop codon) and allows translation to read through the codon to produce the protein, thereby suppressing the stop codon.

The term "antibody" refers to a protein functionally defined as a binding protein and structurally defined as comprising an amino acid sequence that is recognized by one of skill as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The term "full-length antibody," used interchangeably with "full-length IgG," refers to an immunoglobulin (antibody) structural unit comprising a tetramer, each is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab)'2 dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies also include single chain antibodies (antibodies that exist as a single polypeptide chain), and single chain Fv antibodies (sFv or scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston, et al. (1988) Proc. Nat. Acad. Sci. USA, 85: 5879-5883. While the VH and VL are connected to each as a single polypeptide chain, the VH and VL domains associate non-covalently. The first functional antibody molecules to be expressed on the surface of filamentous phage were single-chain Fv's (scFv); however, alternative expression strategies have also been successful. For example, Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally, and the dimer is incorporated into the phage particle via linkage of one of the chains to g3p (see, e.g., U.S. Pat. No. 5,733,743). The scFv antibodies and a number of other structures converting the naturally aggregated, but chemically separated light and heavy polypeptide chains from an antibody V region into a molecule that folds into a three-dimensional structure substantially similar to the structure of an antigen-binding site are known to those of skill in the art (see, e.g., U.S. Pat. Nos. 5,091,513, 5,132,405, and 4,956,778). Antibodies also include all those that have been displayed on phage (e.g., scFv, Fv, Fab and disulfide linked Fv (Reiter et al. (1995) Protein Eng. 8: 1323-1331). Antibodies can also include diantibodies, miniantibodies and scFv-Fc fusions.

The term "reductase" refers to a thioredoxin reductase (TrxB), glutathione or glutathione reductase (Gor) or any other enzyme that can reduce members of the thioredoxin or glutaredoxin systems.

The term "thioredoxin" includes thioredoxin 1 (TrxA) and thioredoxin 2 (TrxC), as described in Rietsch and Beckwith (1998) Ann. Rev. Genet. 32: 163. Thioredoxins are small proteins characterized by the presence of the motif Cys-Xaa-Xaa-Cys (where Xaa denotes any amino acid) in their active site. Thioredoxin is re-reduced by thioredoxin reductase (encoded by the trxB gene) and NADPH. In a trxB mutant, thioredoxin accumulates in an oxidized form. TrxA is encoded by the trxA gene and TrxB is encoded by the trxB gene.

The term "gor" refers to the glutathione oxidoreductase gene and the term "GOR" refers to glutathione oxidoreductase.

"DsbC" is a protein encoded by the gene dsbC, which catalyzes disulfide bond isomerization. DsbC null mutants have a defect in the folding of proteins with multiple disulfide bonds.

The term "glutathione" refers to γ-L-glutamyl-L-cysteinyl-glycine (GSH), which is a highly conserved low molecular weight thiol found in many organisms including cyanobacteria, proteobacteria, a few strains of gram-positive bacteria, and in all eukaryotes having mitochondria and chloroplasts. Glutathione is synthesized by the action of two enzymes: glutamate-cysteine ligase (gshA) and glutathione synthetase (gshB). Glutamate-cysteine ligase catalyzes the reaction between glutamic acid and cysteine to form γ-glutamyl cysteine, which is subsequently conjugated to glycine by glutathione synthetase to form GSH.

A nucleic acid is "operably linked" to another nucleic acid when it is placed into a functional relationship with another nucleic acid sequence. For example, a promoter or enhancer is operably linked to a coding sequence if it affects the transcription of the sequence; or a ribosomal binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, the synthetic oligonucleotide adaptors or linkers are used in accordance with conventional practice.

AhpC is one of the two subunits of the alkyl hydrogen peroxide reductase AhpCF. The other subunit of AhpCF is flavoenzyme AhpF. Tarataglia et al, J. Biol. Chem., Volume 265, 10535-10540, 1990; Smillie et al, Genbank submission NCBL gi; 216542, 1993). These two proteins act together;

AhpF uses NADH or NADPH as electron donor to AhpC, which reduces physiological lipid peroxides such as linoleic acid hydroperoxide and thymine hydroperoxide and non-physiological alkyl hydroperoxides to their respective non-toxic alcohol forms. This enzymatic complex (or system) scavenges oxygen and its derivatives. AhpC has been demonstrated to act as specific alkyl hydroperoxide-scavenging enzyme for protection against oxygen radical damage, though elimination of reactive nitrogen intermediates also has been demonstrated to occur. AhpF is related to thioredoxin reductases possessing an extended additional N-terminal fragment essential to specifically reduce AhpC.

The term "cytosolic" when used to describe a protein refers to that the protein is present in the cytosol of a cell.

A "heterologous protein or polypeptide" refers to a protein or polypeptide which is not normally produced in the host cell. A heterologous polypeptide can be from the same species and type as the host cell provided that it is expressed from a nucleic acid which has been introduced into the host cell.

An "exogenous polypeptide" refers to a polypeptide that is not naturally produced in a cell and is expressed or present in the cell after being introduced into the cell.

A "null mutation" refers to a mutation in a gene that result in a nonfunctional gene. The null mutation can cause complete lack of production of associated gene product or a product that does not function properly.

The term "protein disulfide isomerase," used interchangeably with the term "disulfide isomerase" or "PDI," refers to an enzyme that catalyzes disulfide bond formation and isomerization. PDI has been implicated in the catalysis of disulfide bond formation and rearrangement through in vitro data. (Creighton et al. (1980) *J. Mol. Biol.* 142:43; Feedman et al. (1989) *Biochem. Soc. Symp.* 5:167; and Bardwell and Beckwith (1993) *Cell* 74:899. Yeast mutants in PDI have been shown to have a defect in the formation of disulfide bonds in carboxypeptidase Y (LaMantia and Lennarz (1993) *Cell* 74:899). Use of PDI for expression of heterologous proteins in host cells is further described in PCT application having publication No. WO 93/25676; WO 94/08012; and EP 509,841.

The term "prolyl isomerase," used interchangeably with "peptidylprolyl isomerase" or "PPlase," refers to an enzyme found in both prokaryotes and eukaryotes that interconverts the cis and trans isomers of peptide bonds with the amino acid proline. Proteins with prolyl isomerase activity include, but are not limited to, cyclophilin (e.g., accession #Q13427), FKBPs (e.g., accession #Q02790), parvulin (e.g., accession #Q9Y237), Tig (e.g., accession #P0A850), SlyD (e.g., accession #POA9K9), and yCpr6 (e.g., accession #S000004206).

The term "deaggregase" refers to a protein chaperone that aids in deaggregating and/or solubilizing proteins of interest that are produced, for example, in a bacterial free translation system. Such chaperones are particularly helpful at high concentrations because their mechanism of action is stoichiometric rather than catalytic and is believed to work by stabilizing hydrophobic patches of the newly synthesized protein while the protein is folding. Non-limiting examples of deaggregases include Skp (e.g., accession #POAEU7), GroEL (e.g., accession #POA6F5), GroES (e.g., accession #POA6F9), DnaK (e.g., accession #POA6Y8), DnaJ (e.g., accession #P08622), or GrpE (e.g., accession #P09372).

When a protein is described to be in a "reduced state," it refers to the protein having more electrons than its oxidized form.

The term "oxidative cytoplasm" refers to the cytosol of a cell in which a substrate is more likely to become oxidized than reduced.

The term "thioredoxin reductase activity" refers to the ability of thioredoxin reductase (TRXB) to maintain thioredoxin 1 in the reduced state.

The term "thioredoxin 1 activity" refers to the ability of thioredoxin1 (TRXA) to maintain ribonucleotide reductase at reduced state.

The term "peroxyreductase activity" refers to the ability of AhpC to reduce physiological lipid oxide.

The term "glutathione reductase activity" refers to the ability of catalyzing the reduction of glutathione disulfide (GSSG) to the sulfhydryl form glutathione (GSH). For example, glutathione reductase (GOR) possesses the glutathione reductase activity.

The term "recombinant" or "recombinantly" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids.

The term "culture titer" refers to the concentration of the protein in the culture media. For example, a culture titer of "136 mg/l" refers to 136 mg protein per 1 liter of cell culture media.

The term "lysate titer" refers to the concentration of the protein in the cell lysate. For example, a lysate titer of "0.655 g/l" refers to 0.655 g protein per 1 liter of cell lysate.

The term "weight percentage," when used to describe the titer or yield of protein produced from a cell culture, refers to the wet weight percentage, i.e., the ratio of the weight of a protein (e.g., IgG) to the weight of cell pellet (undried), from which the protein is extracted. The cell pellet is collected from a cell culture expressing the protein and lysed to release the protein using standard techniques (e.g., as described in Example 6). As an illustrative example, if 100 g cell pellet is lysed to produce 1 liter of lysate, which is determined to contain 50 mg IgG, the weight percentage of the IgG is 50 mg/100 g=0.05%.

III. Host Cells—*E. coli* Strains Having an Oxidative Cytoplasm

The *E. coli* strain in this disclosure can be any *E. coli* strain that is known to one of skill in the art. In some embodiments, the *E. coli* strain is a A (K-12), B, C or D strain. In some embodiments, each of at least some *E. coli* cells from the *E. coli* strain contains an oxidative cytoplasm such that the disulfide bonds in the antibody can form and be maintained. The oxidative status of the cytosol is typically assessed by measuring the redox potential of the cytoplasm of the *E. coli* cell. Methods for measuring cellular redox status are well known, e.g., as described in Gilbert et al. (1990) Adv. Enzymol. Rel. Areas Mol. Biol. 63:69; Holmgren and Fgestedt (1982) J. Biol. Chem. 257: 6926; and Hwang et al. (1992) Science 257: 1496. In some cases, the cytosol of the *E. coli* strain has redox potential in the range of −400 mV to −100 mV, e.g., −350 mV to −150 mV, −300 mV to −200 mV, or −291 mV to −250 mV.

Producing an *E. coli* Strain Having Oxidative Cytoplasm by Genetic Engineering

An *E. coli* strain having oxidative cytoplasm may be one that displays reduced or abolished expression or activity of at least one reductase as compared to a corresponding wild type *E. coli* strain. The reductase may be one or more reductases selected from the group consisting of thioredoxin reductase, glutathione reductase, and glutathione. In some approaches, the *E. coli* strain contains a null mutation in at least one of the reductase disclosed above. In some embodiments, the *E. coli* strain lacks the activity of a thioredoxin reductase encoded by trxB; lacks the activity of a thioredoxin 1 encoded by trxA; and/or lacks the activity of a glutathione reductase encoded by gor. In some embodiments, the *E. coli* strain expresses a mutated AhpC protein, wherein the mutated AhpC protein has glutathione reductase activity. In one illustrative embodiment, the *E. coli* strain is the Snuggle strain, which comprises null mutations in trxA, trxB, and gor and lacks the thioredoxin reductase activity (TrxB), thioredoxin 1 activity (TrxA), and glutathione reductase activity (GOR). The Snuggle strain also overexpresses a DsbC without its signal sequence and overexpresses a variant of the ahpC gene (ahpC*) that encoded an enzyme that lacks perioxireductase activity but has glutathione reductase activity. Methods for confirming that expression of these enzymes are reduced are well known and for example, as disclosed below.

Methods of Introducing Mutations to *E. coli*

In some embodiments, the gene modifications, e.g., the knock-outs of trxA and trxB, can be performed with a site-specific recombination. Site-specific recombination uses enzymes possessing both endonuclease activity and ligase activity and the enzymes recognize a certain part of DNA sequences and replace it with any other corresponding DNA sequences, see Yang W. and Mizuuchi K., Structure, 1997, Vol. 5, 1401-1406(9). Site-specific recombination systems are well known in the art, e.g., Int/att system from bacterio λ phage, Cre/LoxP system from PI bacteriophage and FLP-FRT system from yeast.

Non-limiting examples of methods of introducing site-specific recombination to various proteins disclosed herein include the Cre/Lox and Flp/Frt recombination systems. Both systems are well-known in the art. For instance, site-specific integration into bacterial chromosomes has been reported (see, e.g., Sauer et al., Proc. Natl. Acad. Sci. 85. 5166-5170 (1988); Fukushige et al., Proc. Natl. Acad. Sci., 89. 7905-7907 (1992); Baubonis et al., Nucleic Acids Research. 21, 2025-2029 (1993); Hasan et al., Gene, 150. 51-56 (1994); Golic et al., Cell. 59, 499-509 (1989); Sauer, Mol. Cell. Biolo. 1_, 2087-2096 (1987); Sauer et al., Methods: Companion to Methods in Enzymol. 4., 143-149 (1992); Sauer et al., The New Biologist. 2., 441-449 (1990); Sauer et al., Nucleic Acids Res. 17. 147-161 (1989); Qin et al., Proc. Natl. Acad. Sci. 91. 1706-1710 (1994); Orban et al., Proc. Natl. Acad. Sci., 89, 6861-6865 (1992)). Specific deletions of chromosomal sequences and rearrangements and the excision of foreign DNA as a plasmid from X vectors are also known (see, e.g., Barinaga, Science. 265, 27-28 (1994); Sauer, Methods in Enzymol. 225. 890-900 (1993); Sauer et al., Gene, 70. 331-341 (1988); Brunelli et al., Yeast, 1309-1318 (1993); Invitrogen (San Diego, CA) 1995 Catalog, 35; Clontech (Palo Alto, CA) 1995/1996 Catalog, 187-188). Cloning schemes have been generated so that recombination either reconstitutes or inactivates a functional transcription unit by either deletion or inversion of sequences between recombination sites (see, e.g., Odell et al., Plant Physiol. 106. 447-458 (1994); Gu et al., Cell. 73. 1155-1164 (1993); Lakso et al., Proc. Natl. Acad. Sci. 89. 6232-6236 (1992); Fiering et al., Proc. Natl. Acad. Sci. 90. 8469-8473 (1973); O'Gorman et al., Science. 251, 1351-55 (1991); Jung et al., Science, 259, 984-987 (1993)).

Genes encoding the Cre or Flp recombinases can be provided in trans under the control of either constitutive, inducible or developmentally-regulated promoters, or purified recombinase has been introduced (see, e.g., Baubonis et al., supra; Dang et al., Develop. Genet. 13, 367-375 (1992); Chou et al., Genetics. 131. 643-653 (1992); Morris et al., Nucleic Acids Res. 19. 5895-5900 (1991)).

In some embodiments, the genomic manipulations disclosed herein are performed with a modified site-specific recombination protocol from Kirill A. Datsenko and Barry L. Wanner Proc Natl Acad Sci USA. 2000 Jun. 6; 97(12): 6640-6645. In one embodiment, knocking out a gene for example, trxA, can be performed as follows: A PCR amplicon was generated comprising an antibiotic resistance gene flanked by two FRT sites and homology extensions, (H1 and H2), which are homologous to the two ends of the gene to be knocked out. After transforming cells with this PCR product, the gene to be knocked out is then replaced by the antibiotic resistance gene through Red-mediated recombination in these flanking homology regions. After selection, the resistance gene can be eliminated using a helper plasmid expressing the FLP recombinase, which acts on the directly repeated FRT (FLP recognition target) sites flanking the resistance gene. The Red and FLP helper plasmid can be simply cured by growth at 37° C. because they are temperature-sensitive replicons. Knocking-in a gene, such as dsbC, can be performed by standard molecular cloning techniques that are well known for one skilled in the art.

In some embodiments, the inactivation including deletion of a gene is performed using a CRISPR/Cas system. The CRISPR/Cas system uses a Cas protein and at least one to two ribonucleic acids that are capable of directing the Cas protein to a sequence in a target gene, e.g., gor, to remove the gene. Methods of using CRISPR/Cas system to eliminate gene expression are well known and described in e.g., US. Pat. Pub. No. 2014/0170753, the disclosure of which hereby is incorporated by reference in its entirety.

Additional methods of knocking out a target gene include, but are not limited to, homologous recombination technology, transcription activation of the effector nuclease (Transcription Activator-Like Effector Nuclease, TALEN) technology, a zinc finger nuclease (Zinc-Finger Nuclease, ZFN). These methods are also well known in the art.

Confirming Modified Expression of the Reductases

Various methods can be used to determine protein expression level of the various modified genes in the *E. coli*, and/or confirm whether a gene has been knocked out or knocked in. For example, expression of a gene can be determined by conventional Northern blotting to quantitate the transcription of mRNA. Various labels may be employed, most commonly radioisotopes. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like.

In some embodiments, the expressed protein can be purified and quantified using gel electrophoresis (e.g., PAGE), Western analysis or capillary electrophoresis (e.g., Caliper LabChip). Protein synthesis in cell-free translation reactions may be monitored by the incorporation of radiolabeled amino acids, typically, $^{35}$S-labeled methionine or $^{14}$C-labeled leucine. Radiolabeled proteins can be visualized for molecular size and quantitated by autoradiography after electrophoresis or isolated by immunoprecipitation. The incorporation of recombinant His tags affords another means of purification by $Ni^{2+}$ affinity column chromatography. Protein production from expression systems can be measured as soluble protein yield or by using an assay of enzymatic or binding activity.

In some embodiments, if the protein to be quantified possesses defined biological activity, for example, enzymatic activity (such as alkaline phosphatase) or growth inhibition activity, the expression of the protein of interest can be confirmed by assaying its activity by incubating with proper substrates.

Measuring Enzymatic Activities

In some embodiments, a mutation introduced in one or more of the genes, e.g., trxA, does not abolish protein expression or mRNA expression, but results in a mutein that lacks the activity that the corresponding wild type protein possesses, e.g., thioredoxin activity of TrxA. It is understood by one of skill in the art that sometimes knocking out a gene does not require completely abolishing its activity; thus for purpose of this disclosure, lacking an activity means the mutant protein ("mutein") loses 85-100% of the activity of the control protein, e.g., the wild type protein. The various muteins generated can be tested to confirm that they lack the activity of the wild type protein. For example, each of the coding sequences for the muteins can be separately expressed in a host strain, and the muteins are purified and tested for their activities, as described below.

Confirming the Loss of Thioredoxin Reductase Activity,

In one embodiment, the thioredoxin reductase activity can be measured by its activity in reducing 5,5-Dithiobis(2-nitrobenzoic acid) (DTNB) in the presence of NADPH. The reaction is typically started by mixing DTNB with thioredoxin reductase (TrxR), thioredoxin (Trx), and NADPH. The increase in absorbance at 412 nm are observed over time. The activity of the enzyme can be defined as the rate of absorbance increase. An embodiment of detecting thioredoxin reductase activity is disclosed in U.S. Pat. No. 8,592,468, the relevant portion of the disclosure is herein incorporated by reference.

Confirming the Loss of Thioredoxin Activity

Methods for determining thioredoxin activity are also well known. In one embodiment, the assay is an insulin precipitation assay, such as described by Sung-Jong Jeon et al., European Journal of Biochemistry, Vol. 269, No. 22. Thioredoxins are known to possess an activity as disulfide reductases of insulin; and reduction of insulin disulfide bonds can be measured by the increase in turbidity due to precipitation of the free insulin B-chain. In one illustrative example, a standard assay mixture contains 0.1M potassium phosphate (pH 7.0), 1 mMv EDTA, and 0.13 mM bovine insulin in the absence or in the presence of the recombinant protein, and the reaction was initiated upon the addition of 1 mm dithiothreitol. An increase of the absorbance at 650 nm was monitored at 30° C.

Confirming the Loss of Glutathione Reductase Activity

The glutathione reductase activity of the AhpC* or the loss of the glutathione reductase activity of the mutein GOR can also be monitored. In some embodiments, the glutathione reductase activity is measured by its activity in reducing cysteine. For example, cysteine were incubated with reduction solution containing the candidate protein, e.g., AhpC* or the mutein GOR, in the presence of cofactors. Preferably the cofactor is a coenzyme. Preferably the cofactor is nicotinamide adenine dinucleotide phosphate (NADPH) or nicotinamide adenine dinucleotide (NADH). The reaction reduces cystine to cysteine. The schematic reaction is as follows:

CYS–CYS+2GSH→2CYS+GSSG

GSSG+NADPH→2GSH+NADP+H

The activity can be measured by measuring the production of cysteine. In one particular example, the glutathione reductase activity in terms of reducing cysteine is described in WO2018114576.

Confirming the Loss of Peroxyreductase Activity of AhpC

The lack of peroxyreductase activity of AhpC* can be confirmed by incubating the protein with organic hydroperoxides or hydrogen peroxide in the presence of NADH. A functional peroxyreductase would convert these substrates into water in an NADH-dependent mechanism; a lack of evidence of such conversion indicates a lack of peroxyreductase activity.

Maintaining an Oxidative Cytoplasm by Inhibiting Reductase Activity

Alternatively, the redox potential of the cytoplasm of the *E. coli* cell can be modulated by contacting the cell with an agent that is capable of inhibiting the activity of the one or more reductases in the cell. The redox potential of the cytoplasm can be adjusted to an oxidative state that can promote disulfide bond formation and protein stability. Agents that are capable of inhibiting the one or more reductases as disclosed above are well known, for example, aurothioglucose, aurothiomalate or $CuSO_4$.

Suitable reductase inhibitors can also be identified by screening a library of compounds in an in vitro enzymatic assay. The activities of a target reductase in the presence or absence of a candidate compound can be measured and compared, and the candidate compound can be selected as the reductase inhibitor if it demonstrated an ability to reduce the reductase activity in the assay.

Additional Properties of the *E. coli* Strain that May Promote Antibody Yield

In some embodiments, the *E. coli* strain further expresses a cytosolic prokaryotic disulfide isomerase, which can facilitate protein folding and further improve antibody yield. In one embodiment, the disulfide isomerase is DsbC. In one embodiment, the disulfide isomerase is a yeast protein disulfide isomerase (yPDI), e.g., as described in Groff et al., MAbs 6(3): 671-678 (2014). In some embodiments, the *E. coli* strain further expresses a disulfide oxidase to help promoter disulfide formation and enhance IgG assembly. In one embodiment, the disulfide oxidase is DsbA. In one embodiment, the disulfide reductase is Qsox. In some embodiments, the protein isomerase is a prolyl isomerase. Suitable prolyl isomerase may be include, but are not limited to, FkpA, cyclophilin, FKBPs, parvulin, or slyD. deaggregase skP or groEL/groES, danK, dnaJ, or grpE.

Confirming the Cytosol of the *E. coli* Strain is at an Oxidative State

Whether the *E. coli* strain has an oxidative cytoplasm can be confirmed by measuring the redox potential of the cytoplasm, as disclosed above. Alternatively, the oxidative status of the cytoplasm can be verified by assessing the biological activity of a test protein having one or more disulfide bonds, for example, an LC that is difficult to express in a wild type *E. coli* strain. Preferred test polypeptides or proteins are those which are normally secreted from cells or which are membrane proteins. In some cases, these polypeptides are modified by the deletion or mutation of the signal sequence, such that the proteins are not exported outside of the cytoplasm of the cell.

As one illustrative example, a coding sequence for the LC of the B10 antibody (SEQ ID NO: 2) can be engineered into an expression cassette under a suitable promoter and transformed into the modified *E. coli* strain. The soluble protein fraction that contains the LC is measured. A suitable *E. coli* strain will be able to express in a soluble form of at least 1 mg/100 mL of the LC. Methods for preparing a bacterial lysate and measuring the amount of protein expression (e.g., the expression of LC) in the lysate are well known. In some embodiments, the *E. coli* cells can be treated with a lysis agent to produce a lysate. Cytoplasmic proteins can be released by treating the lysate with enzymes, such as benzonase and egg white lysozyme. The insoluble protein fraction can be separated from the soluble fraction by, e.g., centrifugation. The soluble protein fraction (containing the LC) can be collected and analyzed by SDS-PAGE. The amount of LC protein in the soluble protein fraction can then be quantified by, e.g., densitometry.

IV. Antibodies of Interest

The methods provided herein can be used for recombinant production of any full-length antibodies in *E. coli* cells. Disulfide bonds are present in antibodies and thus the present system are beneficial to prevent degradation and increase yield of the antibody. Any antibodies can be produced using the method described herein in a yield, referring to the amount of protein per liter of culture medium, that is at least about 200 mg/L, at least about 250 mg/L, at least about 500 mg/L, at least about 750 mg/L, or at least about 1000 mg/L. In some embodiments, the antibody is selected from the group consisting of a B10 antibody, an H01 antibody, a 7219 antibody (an anti-CD74 antibody), an anti-PD1 antibody, an anti-Tim3 antibody, an anti-HER2 antibody (e.g., trastuzumab), and an anti LAG3 antibody. B10 and H01 are different antibodies but both target the Folate receptor. Polynucleotides encoding the HC and LC of the antibodies can be introduced into the host cells to express the HC and LC, which can then be assembled to form full-length antibodies. Non-limiting examples of the antibodies are listed in Table 1.

TABLE 1

Exemplary antibodies

| Antibody name | HC (SEQ ID NO) | LC (SEQ ID NO) |
|---|---|---|
| B10 | 1 | 2 |
| H01 | 24 | 2 |
| 7209 | 25 | 9 |
| anti-PD1 | 11 | 12 |
| anti-Tim3 | 13 | 14 |
| anti LAG3 | 15 | 16 |
| Trastuzumab | 27 | 2 |

V. Promoters

Promoters that can be used in the methods of the invention to drive the transcription of the HC or LC may be any appropriate promoter sequence suitable for *E. coli*. Such promoters may include mutant, truncated, and hybrid promoters, and may be obtained from polynucleotides encoding extracellular or intracellular polypeptides either endogenous (native) or heterologous (foreign) to the cell. A promoter used herein may be a constitutive or an inducible promoter.

In some embodiments, the promoter is a constitutive promoter. The promoter may be one that has substantially the same promoter strength as T7, i.e., the strength of the promoter is at least 60%, at least 70%, at least 80% of the strength of T7 promoter. In some embodiments, the T7 promoter comprises or consists of a sequence of SEQ ID NO: 19. In some embodiments, the promoter may exhibit a strength that is within the range of 50-200%, e.g., 80%-150% or 90%-140%, of the strength of T7 promoter. Non-limiting examples of promoters that are suitable for driving the transcription of the HC and LC in the *E. coli* cells include a T3 promoter, an SP6 promoter, a pBad, an XylA, or a PhoA promoter.

The strength of two promoters can be compared by comparing the amount of transcription of a same gene product initiated by the two promoters. For example, host cells containing an expression construct with the promoter to be tested ("test host cells") and control host cells containing a control expression construct (containing the reference promoter, e.g., T7 promoter) can be grown in culture in replicates. The total RNA of the host cells and controls can be extracted and measured by absorbance at 260 nm. cDNA can then be synthesized from the equal amount of total RNA from the test host cells and the control host cells. RT-PCR can be performed to amplify the cDNA corresponding to the transcript produced from the promoter. An exemplary method is described in De Mey et al. ("Promoter knock-in: a novel rational method for the fine tuning of genes", BMC Biotechnol 2010 Mar. 24; 10:26).

In some embodiments, the promoters that drive the expression of the HC and LC are the same, for example, both are T7 promoters. In some cases, the HC and LC are directed by one singular promoter, e.g., one single T7 promoter in a bicistronic operon, as disclosed below. In some embodiments, the promoters for the HC and LC are different promoters. In some embodiments, the promoter strength of the HC and LC are substantially the same. In some embodiments, the promoter strength of the HC and LC are different.

VI. Vector

Polynucleotides encoding an LC and an HC of the antibody can be inserted into one or two replicable vectors for expression in the *E. coli*. Many vectors are available for this purpose, and one skilled in the art can readily select suitable vectors for use in the methods disclosed herein. Besides the gene of interest and promoter that drives the expression of the gene, the vector typically comprises one or more of the following: a signal sequence, an origin of replication, or one or more marker genes.

In some embodiments, a bicistronic vector, which employs a promoter to transcribe both the HC and LC coding sequences. In some embodiments, the HC coding sequence is proximal to the promoter. In some embodiments, the LC coding sequence is proximal to the promoter. Any of promoters disclosed herein can be used in the bicistronic vector. In some embodiments, the promoter is the T7 promoter. In some embodiments, the bicistronic vector further comprises a transcriptional terminator, such as the T7 terminator. The HC and the LC coding sequences may be separated by 15 to 30 nucleotides, e.g., 20 to 24 nucleotides, that is, the two closest nucleotides, one on the HC and the other on the LC, are separated by 15 to 30 nucleotides, e.g., 20 to 24 nucleotides. In some embodiments, the HC and the LC coding sequence are separated by a nucleotide sequence comprising a sequence that encodes a ribosomal binding site.

In some embodiments, the plasmid encoding the HC and LC comprises two monocistronic operons, one for the HC and the other for the LC production. In some embodiments, the two monocistronic operons share the same promoter, e.g., a T7 promoter or a T5 promoter. In some embodiments, the two monocistronic operons comprise different promoters. i.e., the promoter in the monocistronic operon for LC and the promoter in the monocistronic operon for the HC are of different sequence and/or having different promoter activity. Any of the promoters disclosed herein can be used in the vector comprising the two monocistronic operons. In some embodiments, each monocistronic operon further comprises a transcriptional terminator, such as the T7 terminator.

In some embodiments, the translation of the HC is modulated by a first ribosomal binding site and the translation of the LC is modulated by a second ribosomal binding site. The ribosomal binding sites are independently selected to ensure the amount of expression of the HC and LC is at a desired ratio, for example, to ensure the molar ratio of the HC to LC is within the range of 1:1 to 1:3, e.g., about 2.5. This approach can boost the yield of the full-length antibody that are formed by the HC and LC produced in the *E. coli* culture. The ratio of the HC to LC can be determined based on the amount of HC and LC produced in the cell lysate obtained from the *E. coli* culture. The amount of the HC and LC can be determined using any methods suitable for protein quantification. In one illustrative embodiment, the *E. coli* culture is collected and lysed to prepare cell lysates. Optionally, the cell lysates are purified by, e.g., chromatography. The cell lysates or purified cell lysates are treated with a reducing agent (e.g., DTT) to separate the HC and LC. The reduced cell lysate sample can then be analyzed on a SDS-PAGE gel, in which HC and LC are separated and resolved by size. The gel is then blotted using an antibody that recognizes the HC and/or LC. The signal associated with binding between the antibody and HC or LC can be quantified. The signal is proportionally related to the amount of HC or LC produced in the culture.

In some embodiments, the first ribosomal binding site or the second ribosomal binding site comprises SEQ ID NO: 28. In some embodiments, the second ribosomal binding site comprises SEQ ID NO: 29. In some embodiments, the first ribosomal binding site comprises SEQ ID NO: 28 and the second ribosomal binding site comprises SEQ ID NO: 29. In some embodiments, the first ribosomal binding site comprises a sequence that is selected from the group consisting of SEQ ID NO: 17-19, and the second ribosomal binding site comprises a sequence that is selected from the group consisting of SEQ ID NO: 20-23; see Example 13. Tables 2 and 3. In some embodiments, the first ribosomal binding site comprises a sequence selected from the group consisting of SEQ ID NO: 20-22, and the second ribosomal binding site comprises SEQ ID NO: 17-19 (e.g., SEQ ID NO: 17); see Example 24. In some embodiments, the second ribosomal binding site comprises SEQ ID NO: 21. In some embodiments, the second ribosomal binding site comprises SEQ ID NO: 22. In some embodiments, the first ribosomal binding site comprises SEQ ID NO: 17 or SEQ ID NO: 18. Any of the sequences disclosed for the first ribosomal binding site can be used as the second ribosomal binding site so long as the amount of expression of the HC and LC can be maintained at a desired ratio as described above.

In some embodiments, the antibody is selected from the group consisting of SP7219 IgG, B10 IgG, H01 IgG, αPD1 IgG, αTim3 IgG, αLAG3 IgG, and variants thereof.

VII. Antibodies Comprising Non-Natural Amino Acids

Antibodies produced using the methods may comprise at least one non-natural amino acid. In some embodiments, the non-natural amino acids are incorporated in the HC or LC at specific sites in the protein. These non-natural amino acids typically have bio-orthogonal reactive chemical side chains which can be used for conjugation with various biologically active adduct. See below. This approach can introduce additional functionality to the antibody, such as fluorescent or radioactive labels, photoactivatable markers, pharmacokinetic modifying PEGs, or chemotherapeutic agents.

The one or more non-natural amino acids can be located at selected site-specific positions in the heavy chain, or light chain, or both, of the antibody. The site-specific position can be in any domain of the antibody, including any variable domain and any constant domain.

The number of non-natural amino acids present in the LC, HC, or both may vary, ranging from 1-10, e.g., from 2-8, from 3-6, from 5-10, or from 3-7. Heavy chains comprising one or more non-natural amino acids In certain embodiments, the antibodies provided herein comprise one or more non-natural amino acids, each replacing a natural amino acid at a position selected from the group consisting of heavy chain residues HC-F412, HC-K121, HC-Y188, HC-F249, HC-221, HC-S136, HC-525, HC-A40, HC-S119, HC-S190, HC-K222, HC-R19, HC-Y52, or HC-570. In these designations, HC indicates a heavy chain residue. Light chains comprising one or more non-natural amino acids In certain embodiments, the antibodies provided herein comprise one or more non-natural amino acids, each replacing a natural amino acid at a position selected from LC-K43, LC-E162, LC-T22, LC-S7, LC-N152, LC-K43, LC-E162, or LC-D170. In these designations, LC indicates a light chain residue.

An antibody disclosed herein may also contain non-natural amino acids at any combination of the positions in HC and LC as described above.

Illustrative Antibodies Comprising Non-Natural Amino Acids

In one illustrative embodiment, the antibody is a B10 antibody comprising an HC having one or mutations selected from positions HC-F412, HC-Y188, HC-F249 relative to SEQ ID NO: 1, and positions LC-K43 relative to SEQ ID NO: 5. The mutations result in the amino acid codons at these positions being replaced with one or more non-natural amino acid codons. In one embodiment, the non-natural amino acid codon is the amber codon. In some embodiments, the B10 antibody comprises an HC having a sequence selected from the group consisting of SEQ ID NO: 3, 4, 6, and 7; and/or an LC having a sequence of SEQ ID NO: 5. In another illustrative embodiment, the antibody is trastuzumab, which comprises an LC, in which at least one of LC-E42 and LC-E162 is replaced by a non-natural amino acid.

Non-Natural Amino Acids

Suitable non-natural amino acids that can be incorporated in the antibodies include, for example, those disclosed in U.S. Pat. Nos. 10,179,909; 9,938,516; 9,682,934; 10,596,270; and 10,610,571, the entire contents of which are herein incorporated by reference.

The non-natural amino acid may comprise a reactive group useful for forming a covalent bond to a linker or a biologically active adduct (aka a payload), as described below. In certain embodiments, the reactive group is selected from the group consisting of amino, carboxy, acetyl, hydrazino, hydrazido, semicarbazido, sulfanyl, azido and alkynyl. The non-natural amino acids may be L-amino acids, or D-amino acids, or racemic amino acids. In certain embodiments, the non-natural amino acids described herein include D-versions of the natural amino acids and racemic versions of the natural amino acids.

In certain embodiments, the non-natural amino acid is according to any of the following formulas:

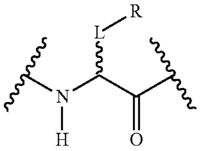
,
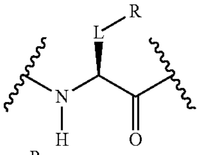
or
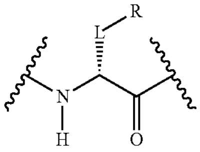
.

In the above formulas, the wavy lines indicate bonds that connect to the remainder of the polypeptide chains of the antibodies. These non-natural amino acids can be incorporated into polypeptide chains just as natural amino acids are incorporated into the same polypeptide chains. In certain embodiments, the non-natural amino acids are incorporated into the polypeptide chain via amide bonds as indicated in the formulas. In the above formulas, R designates any functional group without limitation, so as long as the amino acid residue is not identical to a natural amino acid residue. In certain embodiments, R can be a hydrophobic group, a hydrophilic group, a polar group, an acidic group, a basic group, a chelating group, a reactive group, a therapeutic moiety or a labeling moiety. In the above formulas, each L represents a linker (e.g., a divalent linker), as further described below.

In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, antigen-binding polypeptide that includes a non-naturally encoded amino acid containing an azido functional group can be reacted with a polymer (including but not limited to, poly(ethylene glycol) or, alternatively, a second polypeptide containing an alkyne moiety to form a stable conjugate resulting for the selective reaction of the azide and the alkyne functional groups to form a Huisgen [3+2]cycloaddition product.

Exemplary non-naturally encoded amino acids that may be suitable for use in the present invention and that are useful for reactions with water soluble polymers, including but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid, and the saccharide is replaced by a covalent linkage not commonly found in nature-including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-natural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of skill in the art. For organic synthesis techniques, see, e.g., Organic Chemistry by Fessendon and Fessendon, (1982, Second Edition, Willard Grant Press, Boston Mass.); See, also, U.S. Patent Application Publications 2003/0082575 and 2003/0108885, which is incorporated by reference herein; Advanced Organic Chemistry by March (Third Edition, 1985, Wiley and Sons, New York); and Advanced Organic Chemistry by Carey and Sundberg (Third Edition, Parts A and B, 1990, Plenum Press, New York). Additional publications describing the synthesis of non-natural amino acids include, e.g., WO 2002/085923 entitled "In vivo incorporation of Non-natural Amino Acids;" Matsoukas et al., (1995) J. Med. Chem., 38, 4660-4669; King, F. E. & Kidd, D. A. A. (1949) A New Synthesis of Glutamine and of γ-Dipeptides of Glutamic Acid from Phthylated Intermediates. J. Chem. Soc., 3315-3319; Friedman, O. M. & Chatterrji, R. (1959) Synthesis of Derivatives of Glutamine as Model Substrates for Anti-Tumor Agents. J. Am. Chem. Soc. 81, 3750-3752; Craig, J. C. et al. (1988) Absolute Configuration of the Enantiomers of 7-Chloro-4 [[4-(diethylamino)-1-methylbutyl]amino]quinoline (Chloroquine). J. Org. Chem. 53, 1167-1170; Azoulay, M., Vilmont, M. & Frappier, F. (1991) Glutamine analogues as Potential Antimalarials, Eur. J. Med. Chem. 26, 201-5; Koskinen, A. M. P. & Rapoport, H. (1989) Synthesis of 4-Substituted Prolines as Conformationally Constrained Amino Acid Analogues. J. Org. Chem. 54, 1859-1866; Christie, B. D. & Rapoport, H. (1985) Synthesis of Optically Pure Pipecolates from L-Asparagine. Application to the Total Synthesis of (+)-Apovincamine through Amino Acid Decarbonylation and Iminium Ion Cyclization. J. Org. Chem. 1989:1859-1866; Barton et al., (1987) Synthesis of Novel a-Amino-Acids and Derivatives Using Radical Chemistry: Synthesis of L- and D-α-Amino-Adipic Acids, L-a-aminopimelic Acid and Appropriate Unsaturated Derivatives. Tetrahedron Lett. 43:4297-4308; and, Subasinghe et al., (1992) Quisqualic acid analogues: synthesis of beta-heterocyclic 2-aminopropanoic acid derivatives and their activity at a novel quisqualate-sensitized site. J. Med. Chem. 35:4602-7. See also, patent applications entitled "Protein Arrays," filed Dec. 22, 2003, Ser. No. 10/744,899 and Ser. No. 60/435,821 filed on Dec. 22, 2002.

Many non-natural amino acids are based on natural amino acids, such as tyrosine, glutamine, phenylalanine, and the like and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a C6-C20 straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenyalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of non-natural amino acids that may be suitable for use in the present invention include, but are not limited to, an azidoethoxycarbonyl lysine (AEK), a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-azido-methyl-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of non-natural amino acids that may be suitable for use in the present invention are provided in, for example, WO 2002/085923 entitled "In vivo incorporation of non-natural amino acids." See also Kiick et al., (2002) Incorporation of azides into recombinant proteins for chemoselective modification by the Staudinger ligation, PNAS 99:19-24, for additional methionine analogs.

Particular examples of useful non-natural amino acids include, but are not limited to, p-acetyl-L-phenylalanine, O-methyl-L-tyrosine, L-3-(2-naphthyl)alanine, 3-methyl-phenylalanine, O-4-allyl-L-tyrosine, 4-propyl-L-tyrosine, tri-O-acetyl-GlcNAc b-serine, L-Dopa, fluorinated phenylalanine, isopropyl-L-phenylalanine, p-azido-methyl-L-phenyl alanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, isopropyl-L-phenylalanine, and p-propargyloxy-phenylalanine. Further useful examples include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine.

In particular embodiments, the non-natural amino acids are selected from p-acetyl-phenylalanine, p-ethynyl-phenylalanine, p-propargyloxyphenylalanine, p-azido-methyl-phenylalanine, and p-azido-phenylalanine. In one embodiment, the non-natural amino acid is p-azido phenylalanine. This amino acid residue is known to those of skill in the art to facilitate Huisgen [3+2] cyloaddition reactions (so-called "click" chemistry reactions) with, for example, compounds bearing alkynyl groups. This reaction enables one of skill in the art to readily and rapidly conjugate to the antibody at the site-specific location of the non-natural amino acid.

In certain embodiments, the first reactive group is an alkynyl moiety (including but not limited to, in the non-natural amino acid p-propargyloxyphenylalanine, where the propargyl group is also sometimes referred to as an acetylene moiety) and the second reactive group is an azido moiety, and [3+2]cycloaddition chemistry can be used. In certain embodiments, the first reactive group is the azido moiety (including but not limited to, in the non-natural amino acid p-azido-L-phenylalanine) and the second reactive group is the alkynyl moiety.

The non-natural amino acids used in the methods and compositions described herein have at least one of the following four properties: (1) at least one functional group on the sidechain of the non-natural amino acid has at least one characteristics and/or activity and/or reactivity orthogonal to the chemical reactivity of the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), or at least orthogonal to the chemical reactivity of the naturally occurring amino acids present in the polypeptide that includes the non-natural amino acid; (2) the introduced non-natural amino acids are substantially chemically inert toward the 20 common, genetically-encoded amino acids; (3) the non-natural amino acid can be stably incorporated into a polypeptide, preferably with the stability commensurate with the naturally-occurring amino acids or under typical physiological conditions, and further preferably such incorporation can occur via an in vivo system; and (4) the non-natural amino acid includes an oxime functional group or a functional group that can be transformed into an oxime group by reacting with a reagent, preferably under conditions that do not destroy the biological properties of the polypeptide that includes the non-natural amino acid (unless of course such a destruction of biological properties is the purpose of the modification/transformation), or where the transformation can occur under aqueous conditions at a pH between about 4 and about 8, or where the reactive site on the non-natural amino acid is an electrophilic site. Any number of non-natural amino acids can be introduced into the polypeptide. Non-natural amino acids may also include protected or masked oximes or protected or masked groups that can be transformed into an oxime group after deprotection of the protected group or unmasking of the masked group. Non-natural amino acids may also include protected or masked carbonyl or dicarbonyl groups, which can be transformed into a carbonyl or dicarbonyl group after deprotection of the protected group or unmasking of the masked group and thereby are available to react with hydroxylamines or oximes to form oxime groups.

In further embodiments, non-natural amino acids that may be used in the methods and compositions described herein include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or non-covalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, aldehyde-containing amino acids, amino acids comprising polyethylene glycol or other polyethers, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

In some embodiments, non-natural amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature-including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

In particular embodiments, the non-natural amino acid is one selected from the group of non-natural amino acids shown in FIG. 8A-8I. Such non-natural amino acids may be in the form of a salt or may be incorporated into a non-natural amino acid polypeptide, polymer, polysaccharide, or a polynucleotide and optionally post translationally modified.

In some embodiments, the non-natural amino acid is para-methylazido-L-phenylalanine (pAMF), Azidoethoxycarbonyl lysine (AEK), or p-acetyl-L-phenylalanine (pAcF). In some embodiments, the non-natural amino acid is (S)-2-amino-3-(5-(6-methyl-1,2,4,5-tetrazin-3-ylamino)pyridin-3-yl)propanoic acid.

Incorporation of Non-Natural Amino Acids

Methods for incorporating the non-natural amino acids are well known, e.g., as described in U.S. Pat. Nos. 10,610,571, 9,988,619 and 9,938,516, the entire contents of which are herein incorporated by reference.

In one approach, the coding sequence of the HC or LC is modified to contain at least one non-natural amino acid codon. The non-natural amino acid codon is one that does not result in the incorporation of any of the 20 natural amino acids. In some embodiments, the non-natural amino acid codon is an amber, opal, or ochre stop codon, which is repurposed to charge a non-natural amino acid to its cognate tRNA by a tRNA synthetase instead of terminating translation.

A non-natural amino acid can be charged to a tRNA by a tRNA synthetase, which preferentially acetylates the non-natural amino acid as compared to any of the 20 natural amino acids. tRNA synthetases having such function are known, for example, U.S. Pat. No. 9,938,516 discloses tRNA synthetases that selectively incorporate a non-natural amino acid para-methylazido-L-phenylalanine (pAMF). tRNA synthetases that can selectively incorporate other non-natural amino acids, for example, Azidoethoxycarbonyl lysine (AEK) or -acetyl-L-phenylalanine (pAcF), are also well known; see, for example, Chen et al., *Angew Chem Int Ed Engl.* 2009; 48(22):4052-5 (doi: 10.1002/anie.200900683); and Li et al., *Proc Natl Acad Sci USA,* 2003 Jan. 7; 100(1):56-61. The entire contents of said publications are herein incorporated by reference. Additional exemplary non-natural amino acids that can be incorporated into the antibodies disclosed herein include aralkyl, heterocyclyl, and heteroaralkyl, and lysine-derivative unnatural amino acids. In some embodiments, such non-natural amino acid comprise pyridyl, pyrazinyl, pyrazolyl, triazolyl, oxazolyl, thiazolyl, thiophenyl, or other heterocycle. Such amino acids in some embodiments comprise azides, tetrazines, or other chemical group capable of conjugation to a coupling partner, such as a water soluble moiety.

tRNA synthetases that are capable of selectively incorporating a non-natural amino acid may be also be obtained by genetically modifying a wild type tRNA synthetase to produce mutant tRNA synthetases. Each of these mutant tRNA synthetases can then be tested for its activity in selectively incorporating the non-natural amino acid using in a reporter gene, which contains the desired non-natural amino acid codon. The activity of the mutant tRNA synthetase variant in the presence of the non-natural amino acid (e.g., pAMF) as compared to the 20 common naturally occurring amino acids can be measured by detecting the presence or absence of the reporter protein. One exemplary method of generating mutant tRNA synthetases for incorporating non-natural amino acids is disclosed in U.S. Pat. No. 9,938,516, the entire content of which is herein incorporated by reference.

In some embodiments, the non-natural amino acid codon is a synthetic codon, and the unnatural amino acid is incorporated into the antibody using an orthogonal synthetase/tRNA pair. The orthogonal synthetase may be a synthetase that is modified from any of the natural amino acid synthetases. For example, the orthogonal synthetase may be a proline synthetase, a modified serine synthetase, a modified tryptophan synthetase, or a modified phosphoserine synthetase. The orthogonal tRNA may also be modified from any of the natural amino acid tRNA. For example, the orthogonal tRNA may be a modified alanine tRNA, a modified arginine tRNA, a modified aspartic acid tRNA, a modified cysteine tRNA, a modified glutamine tRNA, a modified glutamic acid tRNA, a modified alanine glycine, a modified histidine tRNA, a modified leucine tRNA, a modified isoleucine tRNA, a modified lysine tRNA, a modified methionine tRNA, a modified phenylalanine tRNA, a modified proline tRNA, a modified serine tRNA, a modified threonine tRNA, or a modified tryptophan tRNA. In some embodiments, a modified tyrosine tRNA, a modified valine tRNA, or a modified phosphoserine tRNA.

Codon Optimization

Codon optimization may be used to increase the rate of translation of the HC or LC or to produce recombinant RNA transcripts having desirable properties, such as a longer half-life, as compared with transcripts produced using a non-optimized sequence. The HC or LC coding sequences may be optimized to maximize expression efficiency in *E. coli*. In particular, when expressing an HC or an LC polynucleotide having a non-natural amino acid codon in *E. coli*, bases that are in the vicinity of the non-natural amino acid codon may have affect the mRNA conformation in the P site in the ribosome and thus have an impact on the efficiency of incorporating the non-natural amino acid. Thus, it is desirable to optimize the codons for the amino acid in the vicinity of the non-natural amino acid codon to maximize the yield of the antibodies having the non-natural amino acids. In some embodiments, the codon that is immediately 3' to the non-natural amino acid codon is optimized in order to maximize expression. The optimal codon can be selected by comparing the yield of HCs (or LC) produced from expressing the HC (or LC) coding sequences having different codons for the same amino acid that is located immediately 3' to the non-natural amino acid codon and selecting the coding sequence that produces the highest yield. In one illustrative example, the coding sequence for the HC of the B10 antibody has an amber codon instead of a tyrosine (Y) codon at position 180. Position 181, which is located immediately 3' to the amber codon, is a serine. The HC coding sequence having a serine codon AGC or AGT at the position produced higher titer than the HC coding sequence having a serine codon TCG at the same position. See, Example 11, FIG. 2.

VIII. Methods

Unless defined otherwise, all technical and scientific terms used herein have the meaning commonly understood by one of ordinary skill in the art to which this invention belongs. Practitioners are particularly directed to Green, M. R., and Sambrook, J., eds., Molecular Cloning: A Laboratory Manual, 4th ed., Cold Spring Harbor Laboratory Press, Cold Spring Harbor, N.Y. (2012), and Ausubel, F. M., et al., Current Protocols in Molecular Biology (Supplement 99), John Wiley & Sons, New York (2012), which are incorporated herein by reference, for definitions and terms of the art. Standard methods also appear in Bindereif, Schón, & Westhof (2005) Handbook of RNA Biochemistry, Wiley-VCH, Weinheim, Germany which describes detailed methods for RNA manipulation and analysis, and is incorporated herein by reference. Examples of appropriate molecular techniques for generating recombinant nucleic acids and instructions sufficient to direct persons of skill through many cloning exercises are found in Green, M. R., and Sambrook, J., (Id.); Ausubel, F. M., et al., (Id.); Berger and Kimmel, Guide to Molecular Cloning Techniques, Methods in Enzymology (Volume 152 Academic Press, Inc., San Diego, Calif. 1987); and PCR Protocols: A Guide to Methods and Applications (Academic Press, San Diego, Calif. 1990), which are incorporated by reference herein.

PCR amplification methods are well known in the art and are described, for example, in Innis et al., PCR Protocols: A Guide to Methods and Applications, Academic Press Inc. San Diego, Calif., 1990. An amplification reaction typically includes the DNA that is to be amplified, a thermostable DNA polymerase, two oligonucleotide primers, deoxynucleotide triphosphates (dNTPs), reaction buffer and magnesium. Typically a desirable number of thermal cycles is between 1 and 25. Methods for primer design and optimization of PCR conditions are well known in the art and can be found in standard molecular biology texts such as Ausubel et al., Short Protocols in Molecular Biology, $5^{th}$ Edition, Wiley, 2002, and Innis et al., PCR Protocols, Academic Press, 1990. Computer programs are useful in the design of primers with the required specificity and optimal amplification properties (e.g., Oligo Version 5.0 (National Biosciences)). In some embodiments, the PCR primers may additionally contain recognition sites for restriction endonucleases, to facilitate insertion of the amplified DNA fragment into specific restriction enzyme sites in a vector. If restriction sites are to be added to the 5' end of the PCR primers, it is preferable to include a few (e.g., two or three) extra 5' bases to allow more efficient cleavage by the enzyme. In some embodiments, the PCR primers may also contain an RNA polymerase promoter site, such as T7 or SP6, to allow for subsequent in vitro transcription. Methods for in vitro transcription are well known to those of skill in the art (see, e.g., Van Gelder et al., Proc. Natl. Acad. Sci. U.S.A. 87:1663-1667, 1990; Eberwine et al., Proc. Natl. Acad. Sci. U.S.A. 89:3010-3014, 1992).

When the antibodies described herein are referred to by name, it is understood that this includes antibodies with similar functions and having HCs and LCs with similar amino acid sequences. For example, the name "B10 antibody" includes the wild-type antibody having an HC of a sequence of SEQ ID NO: 1, and an LC of a sequence of SEQ ID NO: 2, as well as antibodies having an HC and/or light chain having similar amino acid sequences to the SEQ ID NO: 1 or SEQ ID NO: 2. The sequence similarity may be at least 80%, 85%, 90%, 95%, 96%, 97%, 98%, or 99%. The sequence identity of a protein is determined using the BLASTP program with the defaults wordlength of 3, an expectation (E) of 10, and the BLOSUM62 scoring matrix (see Henikoff and Henikoff, *Proc. Natl. Acad. Sci. USA* 89:10915-10919, 1992).

Transformation

Vectors comprising the HC and LC coding sequences may be transfected into a host cell by standard techniques. The various forms of the term "transfection" are intended to encompass a wide variety of techniques commonly used for the introduction of exogenous DNA into a *E. coli* cell, e.g., electroporation, calcium-phosphate precipitation, DEAE-dextran transfection and the like. *E. coli* cells transformed with the vector can be cultured under suitable growth conditions to allow the expression of HC and LC. Cells are harvested and cell lysates are prepared using standard techniques.

Assembling the HC and LC

The cell lysates prepared from the *E. coli* culture can be adjusted to a condition to allow the two LC and two HC to assemble into a tetrameric form of the full-length antibody, including allowing the dimerization of the two heavy chain and association between the heavy chain and light chain through formation of the disulfide bonds. Typically, cell lysates are adjusted to a suitable pH (e.g., pH 8.0), and incubated for an extended time by shaking to allow the formation of disulfide bonds and the assembling of the full-length antibody. In one illustrative example, the cell lysate is adjusted to pH 8.0 with 100 mM Tris HCl by incubating for 16 hrs in a FlowerPlate (m2p-labs) at 25° C. with shaking at 650 rpm.

Purifying the Full-Length Antibody

The assembled IgGs were purified from cell lysate using standard affinity chromatography methods. Various methods for protein purification, chromatography, electrophoresis, centrifugation, and crystallization are described in Coligan et al. (2000) Current Protocols in Protein Science, Vol. 1, John Wiley and Sons, Inc., New York. Methods for cell-free synthesis are described in Spirin & Swartz (2008) Cell-free Protein Synthesis, Wiley-VCH, Weinheim, Germany. The extent of the assembly of the HC and LC in the antibody can be determined using methods well known in the art, e.g., by a caliper bioanalyzer (Perkin Elmer, Richmond, CA) under non-reducing conditions.

Titer/Yield

The titer of the assembled full-length antibodies can be determined using standard methods such as, but not limited to, SDS-PAGE, western blotting, chromatography, e.g., analytical size exclusion chromatography, liquid chromatography and HPLC, immuno-based assays, and enzyme-linked immunosorbent assays (ELISAs). One illustrative example is shown in Example 22.

In some embodiments, especially when the *E. coli* cells are grown in high density for IgG production, for example, the $OD_{600}$ is in the range of 50-150, the titer of the full-length antibody (in terms of the amount of antibody per liter of culture medium) produced using the methods disclosed herein is greater than about 200 mg/L, about 250 mg/L, about 300 mg/L, about 350 mg/L, about 400 mg/L, about 450 mg/L, about 500 mg/L, about 550 mg/L, about 600 mg/L, about 650 mg/L, about 700 mg/L, about 750 mg/L, about 800 mg/L, about 850 mg/L, about 900 mg/L, about 950 mg/L, about 1000 mg/L or more. In other embodiments, the protein of interest is produced at a concentration (amount or level) of greater than about 1000 mg/L, e.g., about 1100 mg/L, about 1200 mg/L, about 1300 mg/L, about 1400 mg/L, about 1500 mg/L, about 1600 mg/L, about 1700 mg/L, about 1800 mg/L, about 1900 mg/L, about 2000 mg/L, or more. Typically, high density growth is performed in bioreactors in a volume of 0.5 liter to 5 liters, one illustration of which is shown in Example 6. However, it is contemplated that the methods described herein may be performed at larger scales, including in culture volumes of at least 500 L, at least 1000 L, at least 2000 L, at least 2500 L, at least 3000 L, at least 5000 L, at least 8000 L, at least 10,000 L, or greater.

In some embodiments, the titer of the full-length antibody produced using the methods disclosed herein is at a wet weight percentage in a range from 0.05% to 20%, from 0.05% to 10%, from 0.05% to 5%, from 0.05% to 4%, from 0.05% to 3%, from 0.05% to 2%, from 0.05% to 1%, or from 0.05% to 0.5% relative to the weight of a wet cell pellet produced from the *E. coli* cells in the culture. In terms of the lower end of the range, the titer of the full-length antibody produced is at a wet weight percentage that is at least 0.05%, at least 0.1%, at least 0.2%, at least 0.3%, at least 0.4%, at least 0.5%, or at least 0.6% relative to the weight of the *E. coli* cells in the culture.

IX. Antibody-Drug Conjugates

Antibodies produced using the methods in this disclosure can be conjugated to a biologically active adduct (aka, a payload) using a chemical reaction such as click chemistry. In some cases, the antibody comprises one or more non-natural amino acids at specific sites in the protein sequence, and the biologically active adduct can be conjugated to these non-natural amino acids. Having antibodies containing the non-natural amino acids at the desired amino acid location, a biologically active adduct can be conjugated to the non-natural amino acid using a chemical reaction such as the click chemistry. For instance, the pAMF containing antibody produced using the methods disclosed herein can be purified by standard procedures. Then, the purified protein is subject to a click chemistry reaction (e.g., copper(I)-catalyzed azide-alkyne 1,3-cycloaddition reaction or copper-free catalyzed azide-aklyne 1,3-cycloaddition reaction) to directly conjugate a biologically active adduct to the pAMF residue.

Exemplary biologically active adducts for use in the present invention include, but are not limited to, small molecules, oligonucleotides, peptides, amino acids, nucleic acids, sugars, oligosaccharides, polymers, synthetic polymers, chelators, fluorophores, chromophores, other detectable agents, drug moieties, cytotoxic agents, detectable agents, and the like.

Detailed descriptions of a click chemistry reaction for conjugation of a biologically active adduct are found in, e.g., Baskin et al., *Proc. Natl. Acad. Sci.,* 2007, 104: 16793-16797; Kim et al., *Curr. Opin. Chem. Biol.,* 2013, 14:412-419; and Bundy and Swartz, *Bioconjug. Chem.,* 2010, 21(2): 255-263.

In a click chemistry reaction, alkynes are activated for [3+2]cycloaddition with azides. The biologically active adduct containing (e.g., linked to) a strained aklyne (e.g., cyclooctyne or variant thereof) can undergo strain-promoted alkyne-azide cycloaddition with the non-natural amino acid para-methylazido-L-phenylalanine on the protein of interest, thereby conjugating the biologically active adduct to the protein at the amino acid position of the non-natural amino acid. A preferred strained alkyne reagent is the reagent DBCO, shown below.

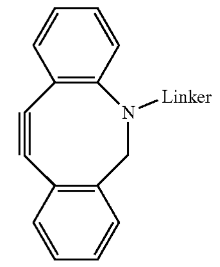

Linker

In certain embodiments, the antibodies can be linked to the biologically active adduct with one or more linkers capable of reacting with an antibody amino acid (e.g., an non-natural amino acid) and with the biologically active adduct. The term "linker" is used to refer to groups or bonds that normally are formed as the result of a chemical reaction and typically are covalent linkages. A linker used in this disclosure can be any linkers apparent to those of skill in the art. In certain embodiments, the linker is any divalent or multivalent linker known to those of skill in the art. Useful divalent linkers include alkylene, substituted alkylene, heteroalkylene, substituted hteroalkylene, arylene, substituted arylene, heteroarlyne, and substituted heteroarylene. In certain embodiments, the linker is C1-10 alkylene or C1-10 heteroalkylene. Suitable linkers are also disclosed in U.S. Pat. No. 10,596,270, the entire content of which is herein incorporated by reference.

The conjugated protein of interest can be purified according to standard methods known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J. -C. Janson and Lars Ryden, editors, VCH Publishers, New York, 1989) to obtain substantially pure polypeptides.

The conjugated protein of interest can be quantitated according to standard methods known in the art including, but not limited to, mass spectrometry (e.g., ESI-TOF mass spectrometry and tanden mass spectometry), microfluidic electrophoresis, gel electrophoresis, Western blotting, immunoassays (e.g., ELISA), and other assays to assess the activity of the conjugated protein.

X. Use

Antibodies produced by the invention, including those incorporating non-natural amino acids, can be used for one or more of the following purposes or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in form or shape); effecting biorhythms or circadian cycles or rhythms; effecting the fertility of male or female subjects;

effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, the ability to bind antigens or complement); and the ability to act as an antigen in vaccine composition to raise an immune response against such protein or another material or entity which is cross-reactive with such protein.

The antibodies produced by the invention can be used for any purpose known to one of skill in the art. Preferred uses include medical uses, including diagnostic uses, prophylactic, and therapeutic uses. For example, the antibodies can be prepared for topical or other type of administration. Accordingly, the proteins produced by the invention are solubilized or suspended in pharmacologically acceptable solutions to form pharmaceutical compositions for administration to a subject. Appropriate buffers for medical purposes and methods of administration of the pharmaceutical compositions are further set forth below. It will be understood by a person of skill in the art that medical compositions can also be administered to subjects other than humans, such as for veterinary purposes.

It is understood that the examples and embodiments described herein are for illustrative purposes only, and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

EXAMPLES

The following examples are offered to illustrate, but not to limit, the claimed invention.

Example 1. Production of Plasmids for Expression of IgGs in Snuggle

IgG production requires the concurrent synthesis of heavy chain (HC) and light chain (LC) polypeptides. To produce IgG expression plasmid pJ411-HC-LC B10, the genes for the HC and LC were cloned into a single bicistronic operon with a T7 promoter and T7 terminator. The bicistronic operon comprises SEQ ID NO: 35. This plasmid has a high copy pUC origin of replication and contains a Kanamycin selectable marker. Plasmid sequences were verified by cloning. Both the HC and LC had independent ribosomal binding sites. To optimize the ratio of HC and LC, mutations were made in the ribosomal binding site of either gene. The parent plasmids PJ411, PJ411, PJ 401, PJ 434, which were used to produce various expression plasmids in the examples, were purchased from ATUM (Newwark, CA). The same expression plasmid pJ411-HC-LC B10 was used in Examples 1-6.

For purposes of this disclosure and examples, "αFolRa B10" and "B10 WT" are used interchangeably. In some cases, additional nomenclature is added to indicate the promoter used in the construct. For example, "B10 WT-T7p" represents a B10 WT construct that uses a T7 promoter.

Example 2. Shake Flask Example Wt IgG Expression

The *E. coli* strain for expression of αFolR IgG B10 was made by transforming Snuggle, as disclosed in PCT/US2019/060345, with plasmid pJ411-HC-LC B10. This strain was grown overnight at 37° C. in terrific broth (TB) with 50 μg/ml kanamycin. In the morning, it was diluted 1:50 into fresh TB+Kan and grown at 37° C. until an $OD_{600}$ of 1.5. At this point, expression of the HC and LC genes were induced by the addition of arabinose to a final concentration of 0.2%. The temperature was adjusted to 25° C. and protein expression continued for 16 hours. Cells were harvested by centrifugation at 6000×g for 10 minutes.

Example 3. Analysis of Shake Flask In Vivo IgG Expression

Cells were harvested by centrifugation at 6000×g for 10 minutes as described in Example 2 and were then frozen. Thawed cells were lysed by sonication in modified S30 buffer (10 mM Tris HCl pH 8.2, 2 mM Magnesium Acetate, 60 mM Potassium Acetate and 0.1 mg/l hen egg white lysozyme) at 10 mL/g wet cell weight (wcw) and debris was removed by centrifugation at 19,000×g for 30 min. IgGs were purified from the cell lysate using standard protein A affinity chromatography methods, and antibody concentration was determined by UV/Vis spectroscopy.

Example 4. Comparison of In Vivo IgG Expression in Oxidizing Cytoplasm Strains Shuffle and Snuggle Strains Snuggle and Shuffle (NEB, Cambridge MA) were transformed with plasmid pJ411-HC-LC B10. The difference in the genetic composition of Suggle and Shuffle is described in International Application No. PCT/US2019/060345. In brief, the Shuffle strain lacks the thioredoxin reductase activity (TRXB) and glutathione reductase activity (GOR). The Shuffle also overexpresses a DsbC without its signal sequence and a variant of the ahpC gene (ahpC*) encoding an enzyme that lacks peroxyreductase activity but has glutathione reductase activity. As compared to Shuffle, the Snuggle strain has been further engineered (based on Shuffle) so that it also lacks the thioredoxin 1 activity (TrxA). As a result, the Snuggle strain comprises null mutations in trxA, trxB, and gor and thus lacks the thioredoxin reductase activity (TrxB), thioredoxin 1 activity (TrxA), and glutathione reductase activity (GOR). The Snuggle strain also overexpresses a DsbC without its signal sequence and overexpresses a variant of the ahpC gene (ahpC*) that encoded an enzyme that lacks perioxireductase activity but has glutathione reductase activity.

Cell from both strains were grown overnight at 37° C. in terrific broth (TB) with 50 μg/ml kanamycin. In the morning, both cultures were diluted 1:50 into fresh TB+Kan and grown at 37° C. until both strains reached a final $OD_{600}$ of 1.5. IgG expression was induced in SBDG419 by the addition of a final concentration of 0.2% arabinose. IgG expression in Shuffle cells was induced by the addition of 1 mM IPTG final concentration. The temperature was adjusted to 25° C. and protein expression continued for 16 hours.

Figure 1:
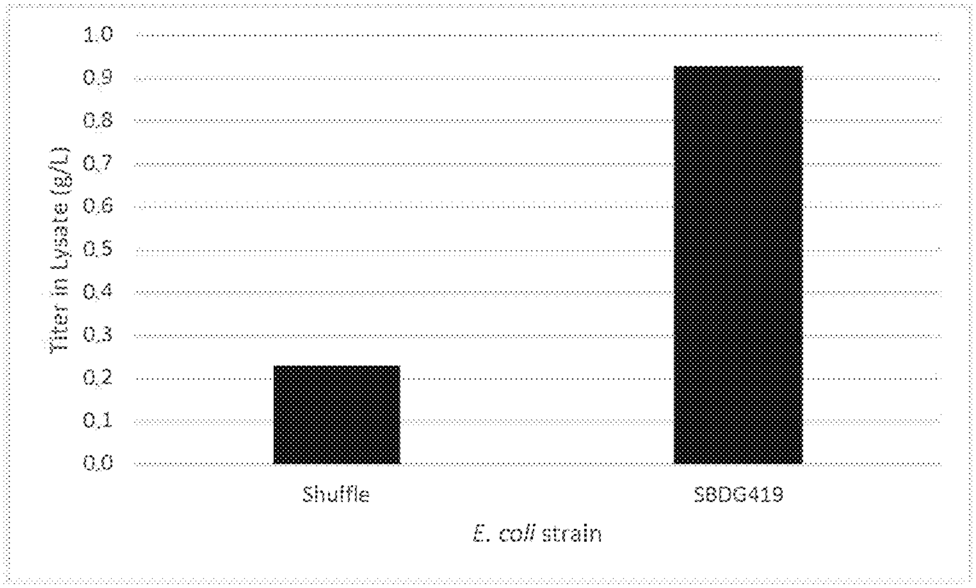
FIG. 1 shows the comparison of titer in cell lysate from Shuffle and Snuggle strains co-expressing the heavy chain (HC) and the light chain (LC) for the FoRa B10 wt IgG, indicating additional mutations present in Snuggle, including e.g., the deletion of the trxA gene and the presence of the wt ahpC gene, are essential for high-level IgG synthesis.

FIG. 1 shows a comparison of titer in cell lysate from Shuffle and Snuggle strains co-expressing HC and LC for the FoRa B10 wt IgG, indicating additional mutations present in Snuggle, as described above, are useful for high level IgG synthesis.

Example 5 Cell Banking Strains for In Vivo Production of Wt IgGs in *E. coli*

The post-transformation culture of each of the WT IgG strains (i.e., pJ4l 1-HC-LC B10), described herein, were streaked on a LB plate containing 50 g/mL of Kanamycin and incubated in a 30° C. incubator for colony development. A single colony was then picked and inoculated in a 50 mL bioreactor tube filled with 10 mL of I17-SF Shake Flask Media (Tables 8 and 9 describe the components of I17-SF Shake Flask Media). The tube was then incubated for 15-24 hours at 30° C. and 250 RPM in a shaker with an orbital diameter of 25 mm. Once the OD 595 nm of the culture reached between 2-4, the cells were sub-cultured at a seeding density of 10-25% (v/v) in I17-SF Shake Flask Media. The flask was incubated at 37° C. and 250 RPM in a shaker with an orbital diameter of 25 mm. Once OD 595 nm of 2-3 was reached, the cells were mixed with 80% pre-sterilized glycerol at a concentration of 20% (v/v) and aliquoted into 1 mL cryovials, which were then flash frozen in liquid nitrogen and placed in a −80° C. freezer for long-term storage.

Example 6 Expression and Cell Lysis for Wt IgGs Produced in E. *Coli* with High Density Fermentations The fermentation process was initiated by taking a 1 mL vial of the cell bank and inoculating a shake flask containing I17-SF defined Shake Flask Media with 50 μg/ml kanamycin at about 3% (v/v) seeding density. Once an OD 595 nm of 2-4 was reached, the flask culture was used to inoculate a 500 mL bioreactor at a seeding density of 1.5% (v/v) in batched media, which consists of 30 μg/mL of Kanamycin, 0.1% (v/v) P2000 antifoam and 1.2% (v/v) 10×I17 Media in DI H₂O (Tables 5, 6 and 7 describe the components of 10×I17 Media). The bioreactor temperature, dissolved oxygen, and pH setpoints were 37° C., 30%, and 7, respectively. Once the cells grew to an OD 595 nm between 2-5 in the batch phase, the fed batch phase began by feeding 10×I17 Media at an exponential rate of 0.20 h⁻¹. After 10 hours of the fed-batch phase, the temperature of the bioreactor was decreased to 25° C. and the exponential feed rate was decreased to 0.02 h⁻¹. An hour later, the induction phase began by adding L-Arabinose to a target concentration of 4 g/L based on the starting volume of the bioreactor. The induction phase took 24-48 hours before the harvest. At the end of the fermentation, the culture was collected and centrifuged at 18,592×G and 2-8° C. for 15 min in a floor centrifuge. The supernatant was discarded and the cell pellets were resuspended and washed with S30 Buffer (Table 10 describes the components of S30 Buffer) at a concentration of 16.67% (w/w) and centrifuged again with the same conditions used in the initial harvest step. After the wash, the supernatant was discarded and the cells were resuspended with S30-5 Buffer (Table 11 describes the components of S30-5 Buffer) at a concentration of 16.67% (w/w). The cell resuspension was then passed through an Avestin Homogenizer (EmulsiFlex-C5) at 17,000 Psi to disrupt the cells and generate the crude lysate. The crude lysate was further clarified by centrifuging at 18,000-20,000×G and 2-8° C. for 30 minutes in a floor centrifuge. The supernatant (clarified lysate) was collected and aliquoted, flash frozen in liquid nitrogen, and stored at −80° C.

Example 7 Production of Plasmids for Expression of Pamf Containing IgGs in Snuggle Nonnatural amino acid (NNAA) containing IgG production requires the concurrent synthesis of Heavy Chain (HC) and Light Chain (LC) polypeptides with either the HC and/or LC containing an NNAA. To produce the plasmid, pJ411-HC F412TAG-LC B10, for expression of the antibody B10 HC F412 pAMF, the genes for the HC and LC were cloned into a single bicistronic operon with a T7 promoter and T7 terminator. The codon for HC residue F412 was mutated to TAG to specify the location of the NNAA. This plasmid has a high copy pUC origin of replication and contains the gene for Kanamycin resistance. Plasmid sequences were verified by cloning. Both the HC and LC had independent ribosomal binding sites. To optimize the ratio of HC and LC, mutations were made in the ribosomal binding site of either gene. pJ411-HC F412TAG-LC B10 is identical to pJ411-HC-LC B10, except for the mutation of the F412 codon to TAG.

Co-translational pAMF incorporation also requires expression of an amber suppressor tRNA orthogonal to existing aminoacyl tRNA synthetases (AAtRS) and an orthogonal AAtRS that specifically recognizes the amber suppressor tRNA and the pAMF NNAA. The genes for the pAMF AAtRS and tRNA were cloned as a bicistronic operon into vector pJ434, downstream of the inducible T7 promoter and constitutive promoter Pc0. This vector has a p15A origin of replication and β-lactamase selection marker conferring resistance to carbenicillin. Both the origin and marker are compatible with pJ411. Plasmid sequences were verified by cloning.

Example 8 Shake Flask Example Pamf IgG Expression

The *E. coli* strain for expression of the αFolR IgG with pAMF at residue 404 was made by co-transforming Snuggle strain SBDG419 with plasmid pJ411-HC F412TAG-LC B10 and pJ434 Pc0 pAMF RS-tRNA. This strain was grown overnight at 37° C. in terrific broth (TB) containing 50 μg/ml kanamycin and 100 μg/ml carbenicillin. In the morning, it was diluted 1:50 into fresh TB+Kan/Carb and grown at 37° C. until an OD₆₀₀ of 1.5. At this point, T7 driven transcription of HC, LC, AAtRS, and tRNA genes were induced by the addition of a final concentration of 0.2% arabinose and 2 mM pAMF. The temperature was adjusted to 25° C. and protein expression continued for 16 hours. Cells were harvested by centrifugation at 6000×g for 10 minutes.

Example 9 Cell Banking Strains for In Vivo Production of Pamf-IgGs in *E. coli*

The post-transformation culture of the nnAA IgG strains as described in Example 8 was streaked on a LB plate containing 50 g/mL of Kanamycin and 100 g/mL of Carbenicillin and incubated in a 30° C. incubator for colony development. A single colony was then picked and inoculated in a 50 mL bioreactor tube filled with 10 mL of I17-SF Shake Flask Media containing 100 g/mL of Carbenicillin (refer to Table 8 and 9 for the components of I17-SF Shake Flask Media). The tube was then incubated for 15-24 hours at 30° C. and 250 RPM in a shaker with an orbital diameter of 25 mm. Once the OD 595 nm of the culture reached between 2-4, the cells were sub-cultured at a seeding density of 10-25% (v/v) in I17-SF Shake Flask Media. The flask was incubated at 37° C. and 250 RPM in a shaker with an orbital diameter of 25 mm. Once OD 595 nm of 2-3 was reached, the cells were mixed with 80% pre-sterilized glycerol at a concentration of 20% (v/v) and aliquoted into 1 mL cryovials which were then flash frozen in liquid nitrogen and placed in a −80° C. freezer for long-term storage.

Example 10 Expression and Cell Lysis for Pamf-IgGs Produced in *E. coli* with High Density Fermentations The fermentation process began by taking a 1 mL vial of the cell bank, as described in Example 9, and inoculating a shake flask with I17-SF Shake Flask Media containing 100 g/mL of Carbenicillin at about 3% (v/v) seeding density. Once an OD 595 nm of 2-4 was reached, the flask culture was used to inoculate a 500 mL bioreactor at a seeding density of 1.5% (v/v) in batched media, which consists of 30 g/mL of Kanamycin, 100 g/mL of Carbenicillin, 0.1% (v/v) P2000 antifoam, and 1.2% (v/v) 10×I17 Media in DI $H_2O$ (Tables 5, 6 and 7 describe the components of 10×I17 Media). The bioreactor temperature, dissolved oxygen, and pH setpoints were 370 C, 30%, and 7, respectively. Once the cells grew to an OD 595 nm between 2-5 in the batch phase, the fed batch phase began by feeding 10×I17 Media at an exponential rate of 0.20 $h^{-1}$. After 10 hours of the fed-batch phase, the temperature of the bioreactor was decreased to 25° C., and the exponential feed rate was decreased to 0.02 $h^{-1}$. An hour later, the induction phase began by adding pAMF to a target concentration of 2 mM based on the culture volume of the bioreactor before induction and L-Arabinose to a target concentration of 4 g/L based on the starting volume of the bioreactor. The induction phase took 24-48 hours before the harvest. At the end of the fermentation, the culture was collected and centrifuged at 18,592×G and 2-8° C. for 15 min in a floor centrifuge. The supernatant was discarded and the cell pellets were resuspended and washed with S30 Buffer (refer to Table 10 for more information on the components of S30 Buffer) at a concentration of 16.67% (w/w) and centrifuged again with the same conditions used in the initial harvest step. After the wash, the supernatant was discarded and the cells were resuspended with S30-5 Buffer (refer to Table 11 for information on the components of S30-5 Buffer) at a concentration of 16.67% (w/w). The cell resuspension was then passed through an Avestin Homogenizer (EmulsiFlex-C5) at 17,000 Psi to disrupt the cells and generate the crude lysate. The crude lysate was further clarified by centrifuging at 18,000-20,000 xG and 2-8° C. for 30 minutes in a floor centrifuge. The supernatant (clarified lysate) was collected and aliquoted, flash frozen in liquid nitrogen and stored at −80° C.

Example 11 Optimization of Codons 3' to Tag for Expression of Nnaa Containing IgGs To optimize the S181 codon for production of B10 Y188 pAMF containing IgGs, the HC Y188TAG gene was produced with Ser codons AGC or AGT at the Ser181 position. The genes for the HC and LC were cloned into pJ411 with a single bicistronic operon with a T7 promoter and T7 terminator. This plasmid, pJ411-HC Y188TAG-LC B10, has a high copy pUC origin of replication and contains the gene for Kanamycin resistance. Plasmid sequences were verified by cloning. Both the HC and LC had independent ribosomal binding sites having a sequence of SEQ ID NO: 17 and SEQ ID NO: 20, respectively. pJ411-HC Y188TAG-LC B10 is identical to pJ411-HC-LC B10, except for the mutation of the Y188 codon to TAG.

Strain SBDG419 was co-transformed with the codon optimized B10 expression plasmids and pJ434 containing pAMF RS and tRNA, and pAMF containing IgGs were expressed as in Example 8.

Figure 2:
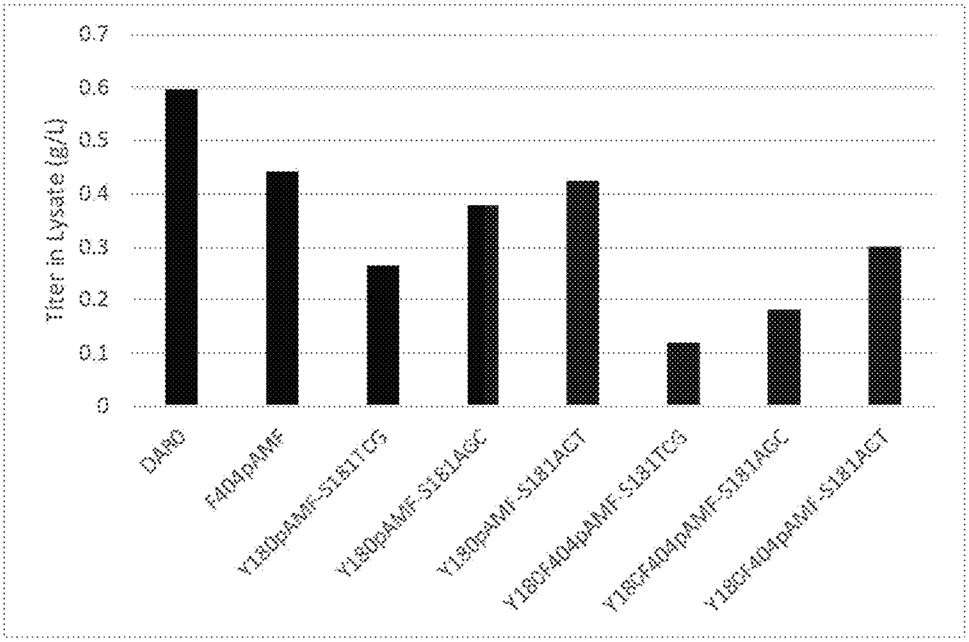
FIG. 2 shows the comparison of titer in cell lysate for FolRa-B10 IgGs produced with 0, 2, or 4 pAMF non-natural amino acids and the indicated S181 codons. "DAR0" represents the B10 IgG that does not contain any non-natural amino acids.

FIG. 2 shows a comparison of titer in cell lysate for FolRa-B10 IgGs produced with 0, 2, or 4 pAMF non-natural amino acids and the indicated S181 codons. As shown in FIG. 2, the HC Y188TAG gene was made with Sercodons AGC and AGT at the Ser181 position shows higher titer than the one having TCG at same position. This indicates that optimization of the 3' S181 codon can substantially improve titers.

Example 12 Reassembly of In Vivo Produced IgGs

IgG reassembly was performed in cell lysate adjusted to pH 8.0 with 100 mM Tris HCl by incubating for 16 hrs in a flowerplate (m2p-labs) at 25° C. with shaking at 650 rpm. Re-assembled IgGs were purified from the cell lysate using standard affinity chromatography methods and assembly was determined by caliper bioanalyzer under non-reducing conditions.

Figure 3:
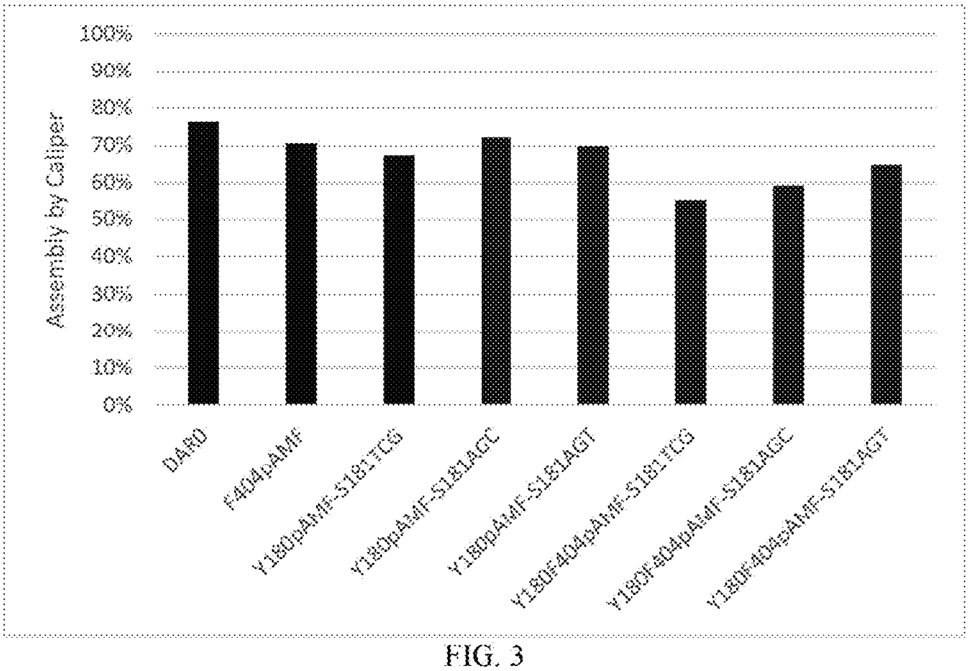
FIG. 3 shows the comparison of assembly of FolRa-B10 IgGs produced with 0, 2, or 4 pAMF non-natural amino acids after overnight reassembly by FlowerPlate determined by caliper bioanalyzer under non-reducing conditions.

FIG. 3 shows a comparison of assembly of FolRa-B10 IgGs produced with 0, 2, or 4 pAMF non-natural amino acids after overnight reassembly by flowerplate determined by caliper bioanalyzer under non-reducing conditions.

Example 13 Screening of Ribosomal Binding Site Variants for Optimal Expression of Iggs in *E. coli*

Plasmids containing ribosomal binding site (RBS) variants of both the HC and LC for the SP7219 IgG were co-transformed in SBDG419 with pJ434 Pc0 pAMF RS-tRNA. Cells were grown overnight at 37° C. in terrific broth (TB) with 50 µg/ml kanamycin and 100 µg/ml carbenicillin. In the morning, it was diluted 1:50 into fresh TB+Kan/Carb and grown at 37° C. until an $OD_{600}$ of 1.5. At this point T7 driven transcription of HC, LC, AAtRNAS and tRNA genes were induced by the addition of a final concentration of 0.2% arabinose and 2 mM pAMF was added to the cultures. The temperature was adjusted to 25° C. and protein expression continued for 16 hours. Cells were harvested by centrifugation at 6000×g for 10 minutes. Cells were lysed by sonication in modified S30 buffer (10 mM Tris HCl pH 8.2, 2 mM Magnesium Acetate and 60 mM Potassium Acetate) at 10 mL/g wcw, and debris was removed by centrifugation at 19,000×g for 30 min. IgGs were purified from the cell lysate using standard affinity chromatography methods and concentration was determined by UV/Vis spectroscopy.

TABLE 2

Ribosomal binding site (RBS) variants used for screening relative HC to LC expression of IgGs in *E. coli*.

| Name | Sequence | SEQ ID NO: | Notes |
|---|---|---|---|
| HC-RBS1 | AGGAGGT | 17 | Consensus RBS |
| HC-RBS2 | AAGAGAT | 18 | First mutant |

TABLE 2-continued

| Ribosomal binding site (RBS) variants used for screening relative HC to LC expression of IgGs in *E. coli.* | | | |
|---|---|---|---|
| Name | Sequence | SEQ ID NO: | Notes |
| HC-RBS3 | AAAAGAT | 19 | Second mutant |
| LC-RBS1 | AGGAGAT | 20 | Canonical LC RBS |
| LC-RBS2 | AAGAGAT | 21 | First mutant |
| LC-RBS3 | AAAAGAT | 22 | Double mutant |
| LC-RBS4 | AAAATAT | 23 | Triple mutant |

TABLE 3

IgG titer for SP7219 comparing ribosomal binding site (RBS) variants screened.

| HC RBS | SEQ ID NO | LC RBS | SEQ ID NO | Lysate titer (g/L) | IgG Weight percentage |
|---|---|---|---|---|---|
| RBS1 | 17 | RBS1 | 20 | 0.35 | 0.35% |
| RBS1 | 17 | RBS2 | 21 | 0.50 | 0.50% |
| RBS1 | 17 | RBS3 | 22 | 0.43 | 0.43% |
| RBS1 | 17 | RBS4 | 23 | 0.45 | 0.45% |
| RBS2 | 18 | RBS1 | 20 | 0.60 | 0.6% |
| RBS3 | 19 | RBS1 | 20 | 0.00 | 0% |

A ribosomal binding sequence for the translation of the heavy chain may be transcribed from a DNA sequence of SEQ ID NO: 28: $AX_1GAGX_2T$ (wherein $X_1$ is A or G and $X_2$ is A or G), and a ribosomal binding sequence for the translation of the light chain may be transcribed from a DNA sequence of SEQ ID NO: 29: $AX_1X_2AX_3AT$ (wherein $X_1$ is G or A, $X_2$ is G or A, and $X_3$ is G or T)

Example 14—Shake Flask Expression of Iggs Containing Pacf and Aek Non-Natural Amino Acid in *E. coli*

Strain SBDG419 was co-transformed with plasmids encoding for the B10 F412TAG IgG encoding for the along with pJ434 Pc0 pAcF RS-tRNA or pJ434 Pc0 Mm PylK RS-Mb PylK tRNA. Azidoethoxycarbonyl lysine (AEK) is a substrate for the WT pyrrolysine synthetase. These strains were grown overnight at 37° C. in terrific broth (TB) with 50 μg/ml kanamycin and 100 μg/ml carbenicillin. In the morning, they were diluted 1:50 into fresh TB+Kan/Carb and grown at 37° C. until an $OD_{600}$ of 1.5. At this point, T7 driven transcription of HC, LC, AAtRNAS and tRNA genes were induced by the addition of a final concentration of 0.2% arabinose and 2 mM pAcF or AEK was added to the cultures as appropriate. The temperature was adjusted to 25° C., and protein expression continued for 16 hours. Cells were harvested by centrifugation at 6000×g for 10 minutes. Cells were lysed by sonication in modified S30 buffer (10 mM Tris HCl pH 8.2, 2 mM Magnesium Acetate and 60 mM Potassium Acetate) at 10 mL/g wcw, and debris was removed by centrifugation at 19,000×g for 30 min. IgGs were purified from the cell lysate using standard affinity chromatography methods, and concentration was determined by UV/Vis spectroscopy.

Figure 4:
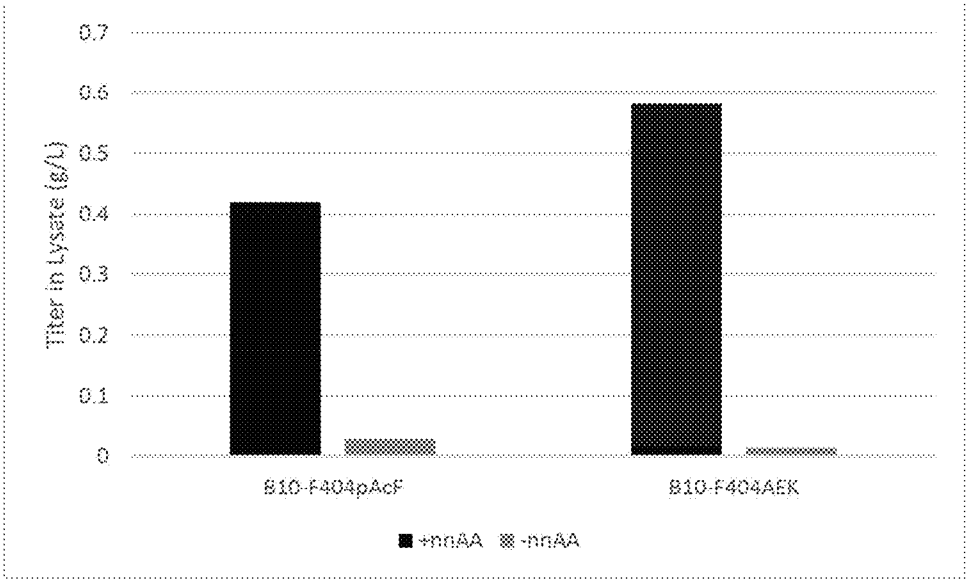
FIG. 4 shows the expression of B10-F412pAcF and B10-F412AEK in the presence and absence of the appropriate non-natural amino acid in the culture media. The low titers in the absence of non-natural amino acid (NNAA) indicate that full-length IgG production requires NNAA for amber suppression.

FIG. 4 shows the expression of BO-F412pAcF and B10-F412AEK, both having a HC ribosomal binding sequence of SEQ ID NO: 17 and an LC ribosomal binding sequence of SEQ ID NO: 20 in the presence and absence of the appropriate non-natural amino acid in the culture media. The low titers in absence of NNAA indicate full-length IgG production requires NNAA for amber suppression.

Example 15 Summary of IgG Titers in Intact *E. coli*

Table 4 and Table 5 summarize the results of titers of IgG produced from *E. coli* in shake flasks or bioreactors under conditions described in the Examples above. The volume of the bioreactors indicated in Table 4 was 0.5 liters.

TABLE 4

Titer of NNAA containing IgGs expressed in *E. coli*

| IgG | DAR | TAG sites | NNAA/system | Scale | Lysate titer (g/l) | Cult. Titer (mg/l) | Wet Weight percentage | Comments |
|---|---|---|---|---|---|---|---|---|
| B10 | 2 | F412 | pAMF/Mj | shake flask | 0.49 | 98 | 0.49% | αFolR IgG |
| B10 | 2 | Y188 | pAMF/Mj | shake flask | 0.38 | 76 | 0.38% | αFolR IgG, S181 WT(TCG) |
| B10 | 2 | Y188 | pAMF/Mj | shake flask | 0.01 | 2 | 0.01% | αFolR IgG, S181 WT(TCG), expressed without NNAA |
| B10 | 2 | Y188 | pAMF/Mj | shake flask | 0.485 | 97 | 0.485% | αFolR IgG, S181 AGC |
| B10 | 2 | Y188 | pAMF/Mj | shake flask | 0.792 | 158.4 | 0.792% | αFolR IgG, S181 AGT |
| B10 | 2 | F249 | pAMF/Mj | shake flask | 0.275 | 55 | 0.275% | αFolR IgG |
| B10 | 4 | F412, K43 | pAMF/Mj | shake flask | 0.615 | 123 | 0.615% | αFolR IgG |
| B10 | 4 | F412, Y188 | pAMF/Mj | shake flask | 0.095 | 19 | 0.095% | αFolR IgG, S181 WT(TCG) |
| B10 | 4 | F412, Y188 | pAMF/Mj | shake flask | 0.375 | 75 | 0.375% | αFolR IgG, S181 AGC |
| B10 | 4 | F412, Y188 | pAMF/Mj | shake flask | 0.44 | 88 | 0.44% | αFolR IgG, S181 AGT |

TABLE 4-continued

| Titer of NNAA containing IgGs expressed in *E. coli* | | | | | | | | |
|---|---|---|---|---|---|---|---|---|
| IgG | DAR | TAG sites | NNAA/system | Scale | Lysate titer (g/l) | Cult. Titer (mg/l) | Wet Weight percentage | Comments |
| B10 | 4 | F412, Y188 | pAMF/Mj | shake flask | 0.285 | 57 | 0.285% | αFolR IgG, S181 WT(TCG), attenuated RF1 |
| B10 | 4 | F412, Y188 | pAMF/Mj | shake flask | 0.215 | 43 | 0.215% | αFolR IgG, S181 AGC attenuated RF1 |
| B10 | 4 | F412, Y188 | pAMF/Mj | shake flask | 0.31 | 62 | 0.310% | αFolR IgG, S181 AGT attenuated RF1 |
| B10 | 4 | F412, Y188 | pAMF/Mj | Bioreactor | 0.38 | 383 | 0.38% | αFolR IgG, S181 WT(TCG) |
| B10 | 4 | F412, Y188 | pAMF/Mj | Bioreactor | 0.49 | 485 | 0.49% | αFolR IgG, S181 AGC |
| B10 | 4 | F412, Y188 | pAMF/Mj | Bioreactor | 0.79 | 796 | 0.79% | αFolR IgG, S181 AGT |
| B10 | 6 | F412, Y188, K43 | pAMF/Mj | shake flask | 0.15 | 30 | 0.15% | αFolR IgG, S181 WT(TCG) |
| B10 | 6 | F412, Y188, K43 | pAMF/Mj | shake flask | 0.29 | 58 | 0.29% | αFolR IgG, S181 AGC |
| B10 | 6 | F412, Y188, K43 | pAMF/Mj | shake flask | 0.35 | 70 | 0.35% | αFolR IgG, S181 AGT |
| H01 | 4 | F412, Y188 | pAMF/Mj | Bioreactor (a volume of 5 liters) | 1.8 | 1771 | 1.8% | STRO2 IgG |
| 7219 | 2 | F412 | pAMF/Mj | Bioreactor (a volume of 5 liters) | 1.1 | 1118 | 1.1% | STRO1 IgG |
| B10 | 2 | F412 | pAcPhe/Mj | shake flask | 0.539 | 107.8 | 0.539% | αFolR IgG |
| B10 | 2 | F412 | AEK/pylK | shake flask | 0.685 | 137 | 0.685% | αFolR IgG |

Purified A280 titers for NNAA IgGs expressed in Snuggle cells co-transformed with plasmids encoding listed IgG and tRNA/AAtRS for specified NNAA. All NNAAs were used at 2 mM except for the third entry in the table which was expressed with 0 mM pAMF. The extremely low titers for this sample demonstrate that NNAA is required for amber suppression and production of full-length IgGs.

TABLE 5

| Titer of *E. coli* expressed IgGs produced in a bioreactor | | | |
|---|---|---|---|
| Product | Bioreactor Volume | Culture titer(mg IgG/L media) | Wet Weight percentage |
| αFolRa B10 IgG | 0.5 L | 1575 | 1.6% |
| αFolRa B10 Y188/F412pAMF IgG | 0.5 L | 796 | 0.80% |
| αFolRa H01 Y188/F412pAMF IgG | 0.5 L | 1771 | 1.7% |
| aCD74 F412pAMF IgG | 0.5 L | 866 | 0.87% |
| aCD74 F412pAMF IgG | 5 L | 1118 | 1.1% |
| aPD1 IgG | 0.5 L | 5922 | 5.9% |
| aTim3 IgG | 0.5 L | 2813 | 2.8% |

Purified A280 titers for NNAA IgGs expressed in Snuggle cells co-transformed with plasmids encoding listed IgG and tRNA/AAtRS for specified NNAA. pAMFW was used at 2 mM.

Example 16 Media and Components for High Density *E. coli* IgG Fermentation

TABLE 6

| Components of 10x 117 Media Solution | | |
|---|---|---|
| Component | Concentration | Unit |
| Potassium Phosphate (Monobasic) | 40.0 | g/L |
| Ammonium sulfate | 15.0 | g/L |
| Potassium Chloride | 10.0 | g/L |
| Sodium Citrate | 10.0 | g/L |
| L-Asparagine•$H_2O$ | 18.5 | g/L |
| L-Methionine | 6.4 | g/L |
| L-Proline | 22.1 | g/L |
| MgSO4•7$H_2O$ | 8.4 | g/L |
| Glucose | 500.0 | g/L |
| Trace Metals (TM) | 3.0 | mL/L |
| Vitamins 1 (V1) | 10.0 | mL/L |
| DI $H_2O$ or better quality | Qs to 1 L | mL |

TABLE 7

| Components of concentrated stock solution of vitamins for 10x 117 Media Solution | | |
|---|---|---|
| Component | Concentration | Units |
| Choline Chloride | 28.64 | g/L |
| Nicotinic Acid (Niacin) | 25.12 | g/L |
| PABA (Aminobenzoic Acid {p-" or "4-"}) | 25.60 | g/L |

TABLE 7-continued

| Components of concentrated stock solution of vitamins for 10x 117 Media Solution | | |
|---|---|---|
| Component | Concentration | Units |
| Pantothenic Acid (B5) | 9.40 | g/L |
| Pyridoxine (B6) (HCl) | 1.47 | g/L |
| Riboflavin (B2) | 3.89 | g/L |
| Thiamine (B1) (HCl) | 17.67 | g/L |
| Potassium Hydroxide (6M) *unit is mL/L | 115.00 | mL/L |
| DI $H_2O$ or better quality | Qs to 1 L | N/A |

TABLE 8

| Components of concentrated stock solution of trace metals for 10x I17 Media Solution | |
|---|---|
| Component | Concentration (g/L) |
| Sodium Citrate Dihydrate | 100.00 |
| Ferric Chloride Hexahydrate | 66.63 |
| Sodium Molybdate Dihydrate | 11.67 |
| Cobalt Chloride Hexahydrate | 11.32 |
| Zince Sulfate Heptahydrate | 11.32 |
| Cupric sulfate Pentahydrate | 11.32 |
| Manganese Sulfate Monohydrate | 6.47 |
| Boric Acid | 4.04 |
| DI $H_2O$ or better quality | Qs to 1 L |

TABLE 9

| Components of I17-SF Shake Flask Media Solution | |
|---|---|
| Component | Concentration (mL/L) |
| 10x Base Salts | 90 |
| 10x I17 Liquid Stock Medium | 10 |
| Kanamycin sulfate (30 g/L stock) | 1 |
| pH to 6.8 +/− 0.1 with 6M KOH | As needed |
| DI $H_2O$ or better quality | Qs to 1 L |

TABLE 10

| Components of 10x Base Salts for 117-SF Shake Flask Media Solution | |
|---|---|
| Component | Concentration (g/L) |
| Potassium Phosphate Monobasic | 75.8 |
| Ammonium sulfate | 15.0 |
| Potassium Chloride | 10.0 |
| Sodium Citrate | 10.0 |
| Magnesium Sulfate Heptahydrate | 8.4 |
| DI $H_2O$ or better quality | Qs to 1 L |

TABLE 11

| Components of S30 Buffer | |
|---|---|
| Component | Concentration (mL/L) |
| 1M Tris, pH 8.2 Stock | 10 |
| 1.4M MgAcO Stock | 10 |
| 6M KAcO Stock | 10 |
| DI $H_2O$ or better quality | 970 |

TABLE 12

| Components of S30-5 Buffer | |
|---|---|
| Component | Concentration (mL/L) |
| 1M Tris, pH 8.2 Stock | 10 |
| 1.4M MgAcO Stock | 1.4 |
| 6M KAcO Stock | 83 |
| DI $H_2O$ or better quality | 1906 |

Example 17 Conjugation of NNAA Containing Mabs

Click chemistry bio-conjugation reactions were carried out for B10-F412TAG IgGs expressed in vivo containing the pAMF, AEK, and pAcF non-natural amino acids. The azide nnAA containing IgGs, B10 F412pAMF, and B10 F412AEK, were conjugated to a DBCO-maytansine linker warhead (SC236) via strain promoted alkyne-azide cycloaddition (SPAAC) "click" chemistry as follows: 1 mg/mL IgG was reacted with a 10-fold molar excess of SC236 in PBS for 16 h at 22 C. The B10 F412pAcF IgG was conjugated to aminooxy-PEG8-methane via oxime ligation as follows: 13 mg/mL IgG was reacted with a 40-fold molar excess of aminooxy-PEG8-methane in 100 mM sodium acetate pH 4.5 for 72 h at 30 C. IgGs were digested with IdeS protease, reduced with DTT, and the extent of the conjugation reaction was determined by LCMS (Agilent Technologies 6520 Accurate-Mass Q-TOF LC/MS).

FIG. 5 shows the deconvoluted LCMS spectra for Fc-fragment of B10 F412pAMF conjugated to the DBCO-maytansine drug-linker SC236. The predominant species observed has a mass of 25257.97 Da compared with the theoretical mass of 25258.04 Da for the conjugate. No species are observed near 23974.14 Da, the theoretical mass for the unconjugated Fc fragment. This conjugate has a calculated conjugation efficiency of 100%.

TABLE 13

| Conjugation efficiency of in vivo produced IgGs containing the nnAAs pAMF, AEK and pAcF determined by LCMS. | | |
|---|---|---|
| Protein | Conjugation partner | Conjugation efficiency |
| B10 F412pAMF IgG | SC236 | 100% |
| B10 F412AEK IgG | SC236 | 100% |
| B10 F412pAcF IgG | Aminooxy-PEG8-methane | 100% |

Example 18. Production of Plasmids for Expression of NNAA Containing Lc in Snuggle Nonnatural amino acid (NNAA) containing LC production requires the synthesis of Light Chain with concurrent incorporation of NNAA. To produce the plasmid, pJ411- trastuzumab LC K43TAG E162TAG, for expression of the LC with a NNAA at the K43 and E162 position, the LC gene was cloned into an operon with a T7 promoter and T7 terminator. The codons for LC residues K43 and E162 were mutated to TAG to specify the location of the NNAA. This plasmid has a high copy pUC origin of replication and contains the gene for Kanamycin resistance. Plasmid sequences were verified by cloning.

Cotranslational NNAA incorporation also requires expression of an amber suppressor tRNA orthogonal to existing aminoacyl tRNA synthetases (AAtRS) and an orthogonal AAtRS that specifically recognizes the amber suppressor tRNA and the pAMF NNAA. The genes for the NNAA AAtRS and tRNA were cloned as a bicistronic operon into vector pJ434, downstream of the inducible T7 promoter and constitutive promoter Pc0. This vector has a p15A origin of replication and β-lactamase selection marker conferring resistance to carbenicillin. Both the origin and marker are compatible with pJ411. Plasmid sequences were verified by cloning.

Example 19 Shake Flask Example P-Ac-Phe LC Expression

The *E. coli* strain for expression of the trastuzumab LC with pAcPhe at residue K43 and E162 were made by co-transforming Snuggle strain SBDG419 with plasmid pJ411-trastuzumab LC K43TAG E162TAG and pJ434 Pc0 pAcPhe RS-tRNA. This strain was grown overnight at 37° C. in terrific broth (TB) with 50 μg/ml kanamycin and 100 μg/ml carbenicillin. In the morning, it was diluted 1:50 into fresh TB+Kan/Carb and grown at 37° C. until an $OD_{600}$ of 1.5. At this point T7 driven transcription of HC, LC, AAtRS, and tRNA genes were induced by the addition of a final concentration of 0.2% arabinose and 2 mM pAcPhe to the cultures. The temperature was adjusted to 25° C. and protein expression continued for 16 hours. Cells were harvested by centrifugation at 6000×g for 10 minutes.

Example 20. Analysis of P-Ac-Phe LC Expression

Cells were frozen at −80° C. overnight, thawed and then resuspended in BPer bacterial protein extraction reagent with 0.01 mg/ml lysosome and 1 μl benzonase nuclease/ml BPer solution to lyse the *E. coli* cells and hydrolyze nucleic acids. After incubating at room temperature for 10 minutes, cells were fully lysed and viscosity from the nucleic acid polymers was reduced. At this point, the lysate was clarified with centrifugation at 24,000×G for 10 minutes. The LC-containing supernatant was saved for analysis. After reduction with 10 mM DTT, the samples were analyzed with a PAGE gel.

Example 21. Purification and Conjugation of P-Ac-Phe LC

Trastuzumab LC K43 pAcPhe E162pAcPhe was purified from lysate after shake flask expression using standard proL chromatography. 143 mg of purified LC were recovered after purification. The LCMS (FIG. 6) of the intact LC indicates that all of the protein recovered was full length and there is no evidence of misincorporation. This means there is good fidelity with this synthetase at both TAG sites, and any truncated proteins do not have affinity for proL. Purified K43pAcPhe E162pAcPhe LC was conjugated. LCMS of the conjugated LC (FIG. 7) demonstrates a drug loading of 1.96 per LC or 98% conjugation efficiency.

TABLE 14

Titers of trastuzumab LC expressed with NNAA

| DAR | TAG sites | NNAA/ system | scale | titer (mg/l culture media) | comments |
|---|---|---|---|---|---|
| 1 | K43 | PAMF/ Mj | 0.5 liter bioreactor | 4100 | titer estimated from gel |
| 1 | K43 | pAcPhe/ Mj | 0.5 literbioreact or | 4100 | titer estimated from gel |
| 1 | K43 | AEK/ PyrK | 0.5 liter bioreactor | 539 | purified protein titer |
| 2 | K43, E162 | pAcPhe/ Mj | shake flask | 166 | S162AGT codon, purified protein titer |
| 2 | K43, E162 | pAcPhe/ Mj | shake flask | 194 | S162AGC codon, purified protein titer |
| 2 | K43, E170 | pAcPhe/ Mj | shake flask | 179 | S171AGT codon, purified protein titer |
| 2 | K43, E170 | pAcPhe/ Mj | shake flask | 180 | S171AGC codon, purified protein titer |

Example 22. Quantifying Protein Production

To measure the amount of HC and LC present in cell lysate, which were reduced with 10 mM DTT, which separated the HC from the LC by treatment with 10 mM DTT and HC and LC protein concentration were determined by Sally Sue automated western blot (Protein Simple, San Jose, CA) according to the manufacturer's directions for the 12-230 kDa separation module (SM-S0001, Protein Simple). Reduced cell lysate was diluted 1:20 in the 0.1× sample buffer. Anti-Human IgG (H+L) Biotin-SP (109-065-003, Jackson ImmunoResearch) was used as a primary antibody at a 1:150 dilution in Antibody Diluant 2. A standard was prepared using a serial dilution of purified H01 antibody in 0.1× sample buffer.

Example 23. Production of IgG Utilizing Alternative Promoter

IgG production requires the concurrent synthesis of heavy chain (HC) and light chain (LC) polypeptides. To produce IgG expression plasmid pJ401-LC-HC B10, the genes for the HC and LC were cloned into a single bicistronic operon with a T5 promoter (T5p) (SEQ ID NO: 23), which recruits the *E. coli* RNA polymerase for transcription. This plasmid has a high copy pUC origin of replication and contains a Kanamycin selectable marker. Plasmid sequences were verified by cloning. Both the HC and LC had independent ribosomal binding sites.

The *E. coli* strain for expression of B10 with this plasmid was made by transforming Snuggle, as disclosed in PCT/US2019/060345, with plasmid pJ401-LC-HC B10. This strain was grown overnight at 37° C. in terrific broth (TB) with 50 μg/ml kanamycin. In the morning, it was diluted 1:50 into fresh TB+Kan and grown at 37° C. until an OD600 of 1.5. At this point, expression of the HC and LC genes were induced by the addition of IPTG to a final concentration of 1 mM. The temperature was adjusted to 25° C., and protein expression continued for 16 hours. Cells were harvested by centrifugation at 6000 g for 10 minutes, lysed, and then IgG expression was analyzed as previously described. The results can be seen in Table 15 indicating that the expression of B10 IgG with the T5 promoter ("B10 WT-T5p") is in line with other high yielding IgGs in a shake flask; conventional expression with the T7 promoter (T7p) ("B10 WT-T7p") is shown for comparison.

TABLE 15

| Titers of IgG B10 transcribed with T5 promoter | | |
|---|---|---|
| B10 expression construct | Lysate titer (g/l) | Culture titer (shake flask) mg/l |
| B10 WT-T7p | 0.655 | 136 |
| B10 WT-T5p | 0.485 | 97 |

Based on the shake flask titers, it is expected that greater than 200 mg/l, or even greater than 1 g/l of the B10 IgG can be produced in the same strain of B10-MO-SDw in high density fermentation setting, such as in bioreactors. This is because previous studies, for example, Example 15, Table 4, show that switching from shake flasks to high-density fermentation usually can increase antibody production by at least 5-fold.

Example 24. Production of IgG Utilizing Alternative Operon Organization

IgG production requires concurrent synthesis of heavy chain (HC) and light chain (LC) polypeptides. Plasmid pJ411 B10 MO was cloned to produce IgG utilizing separate operons for the HC and LC. In this vector the genes for the HC and LC were each cloned into a monocistronic complete operon with a T7 promoter, LC or HC gene and then T7 terminator.

This plasmid has a high copy pUC origin of replication and contains a Kanamycin selectable marker. Plasmid sequences were verified by cloning. Both the HC and LC had independent ribosomal binding sites. To optimize the ratio of HC and LC, mutations were made in the ribosomal binding site of the HC. Three (3) different plasmids were produced, B10-MO-SDs, B10-MO-SDm, B10-MO-SDw, with strong, medium and weak HC ribosomal binding sites comprising SEQ ID NO: 20, 21, and 22, respectively. The LC used the same strong ribosomal binding site (SEQ ID NO: 17) for all constructs because previous studies indicate that more LC expression than HC expression is needed.

The *E. coli* strain for expression of B10 with these plasmids was made by transforming Snuggle, as disclosed in PCT/US2019/060345, with plasmids B10-MO-SDs (SEQ ID NO: 36), B10-MO-SDm (SEQ ID NO: 37), or B10-MO-SDw (SEQ ID NO: 38). This strain was grown overnight at 37° C. in terrific broth (TB) with 50 μg/ml kanamycin. In the morning, it was diluted 1:50 into fresh TB+Kan and grown at 37° C. until an OD600 of 1.5. At this point, expression of the HC and LC genes were induced by the addition of arabinose to a final concentration of 0.2%. The temperature was adjusted to 25° C., and protein expression continued for 16 hours. Cells were harvested by centrifugation at 6000×g for 10 minutes, lysed, and then IgG expression was analyzed as previously described. The results can be seen in Table 16 indicating that the high expression of B10 IgG with separate operons can be achieved with proper SD tuning and HC to LC ratio. The yield for the best construct from this series was in line with other high yielding IgGs in a shake flask; conventional expression with a bicistronic operon ("B10 WT") as described in Example 1 is shown for comparison.

TABLE 16

| Titers of IgG B10 transcribed with separate LC and HC operons | | | |
|---|---|---|---|
| B10 expression construct | Lysate titer (g/l) | Culture titer (shake flask) mg/l | Weight percentage |
| B10 WT (SEQ ID NO: 35) | 0.655 | 131 | 0.655% |
| B10-MO-SDs (SEQ ID NO: 36) | 0.153 | 31 | 0.153% |
| B10-MO-SDm (SEQ ID NO: 37) | 0.123 | 25 | 0.123% |
| B10-MO-SDw (SEQ ID NO: 38) | 0.501 | 100 | 0.501% |

Previous studies, for example, Example 15, table 4, show that switching from shake flasks to high density fermentation usually can increase antibody production by at least 5 fold relative to the shake flask titers. Thus, the results in this example demonstrate that greater than 200 mg/l or even greater than 1 g/l of the B10 IgG can be produced when the same stain of B10-MO-SDw is cultured in high-density fermentation setting such as in bioreactors.

Abbreviations in this Application

- OD 595 nm=Optical Density measure at wavelength of 595 nm
- RPM=Revolutions per minute
- (v/v %)=volume of solute/volume of solution %
- (w/w %)=weight of solute/weight of solution %
- Qs=Quantum satis (add as much as needed to achieve desired
- SD=Shine Dalgarno sequence or ribosomal binding site or RBS;
- SDs or RBSs=strong ribosomal binding site,
- SDm or RBSm=medium strength ribosomal binding site,
- SDw or RBSw=weak strength ribosomal binding site Illustrative Sequences Protein Sequences of IgG LC and HC Expressed in *E. coli*

* denotes site of NNAA

```
(WT B10 HC)
                                                               SEQ ID NO: 1
MEVQLVESGGGLVQPGGSLRLSCAASGFNTTTKSIHWVRQAPGKGLEWVGEIYPRDGITDYADSVKGRFTISADTSKNTAYL

QMNSLRAEDTAVYYCARGGWHSRSGYSYYLDYWGQGTLVTVSSASTKGPSVFPLAPSSKSTSGGTAALGCLVKDYFPEPVTV

SWNSGALTSGVTFPAVLQSSGLYSLLVVTVPSSSLGTQTYICNVNHKPSNTKVDKKVEPKSCDKTHTCPPCPAPELLGGPSV

FLFPPKPKDTLMISRTPEVTCVVVDVSHEDPEVKFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKGFYPSDIAVEWESNGQPENNYKTTPPVLDSDGSF

FLYSKLTVDKSRWQQGNVFSCSVMHEALHNHYTQKSLSLSPGK

(WT B10 LC or H01 LC or trastuzumab LC)
                                                               SEQ ID NO: 2
MDIQMTQSPSSLSASVGDRVTITCRASQDVNTAVAWYQQKPGKAPKLLIYSASFLYSGVPSRFSGSRSGTDFTLTISSLQPE
```

-continued

DFATYYCQQHYTTPPTFGQGTKVEIKRTVAAPSVFIFPPSDEQLKSGTASVVCLLNNFYPREAKVQWKVDNALQSGNSQESV

TEQDSKDSTYSLSSTLTLSKADYEKHKVYACEVTHQGLSSPVTKSFNRGEC (B10 F404TAG HC)

SEQ ID NO: 3

VEVQLVESGGGLVQPGGSLRLSCAASGFNTTTKSIHWVRQAPGKGLEWVGEIYPRDGITDYADSVKGRFTISADTSKNTAYL

QMNSLRAEDTAVYYCARGGWHWRSGYSYYLDYWGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKVDKKVEPKSCDKTHTCPPCPAPELLGGP

SVFLFPPKPKDTLMISRTPEVTCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVKGFYPSDIAVEWESNGQPENNYKTTPPVLDSDG

S*FLYSKLTVDKSRWQQGNVFSCSVMHEALHNHYTQKSLSLSPGK (B10 Y180TAG HC)

SEQ ID NO: 4

MEVQLVESGGGLVQPGGSLRLSCAASGFNTTTKSIHWVRQAPGKGLEWVGEIYPRDGITDYADSVKGRFTISADTSKNTAYL

QMNSLRAEDTAVYYCARGGWHWRSGYSYYLDYWGQGTLVTVSSASTKGPSVFPLAPSSKSTSGGTAALGCLVKDYFPEPVTV

SWNSGALTSGVHTFPAVLQSSGL*SLSSVVTVPSSSLGTQTYICNVNHKPSNTKVDKKVEPKSCDKTHTCPPCPAPELLGGP

SVFLFPPKPKDTLMISRTPEVTCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVKGFYPSDIAVEWESNGQPENNYKTTPPVLDSDG

SFFLYSKLTVDKSRWQQGNVFSCSVMHEALHNHYTQKSLSLSPGK (B10 K42TAG LC)

SEQ ID NO: 5

MDIQMTQSPSSLSASVGDRVTITCRASQDVNTAVAWYQQKPG*APKLLIYSASFLYSGVPSRFSGSRSGTDFTLTISSLQPE

DFATYYCQQHYTTPPTFGQGTKVEIKRTVAAPSVFIFPPSDEQLKSGTASVVCLLNNFYPREAKVQWKVDNALQSGNSQESV

TEQDSKDSTYSLSSTLTLSKADYEKHKVYACEVTHQGLSSPVTKSFNRGEC (B10 Y180TAG F404TAG HC)

SEQ ID NO: 6

MEVQLVESGGGLVQPGGSLRLSCAASGFNTTTKSIHWVRQAPGKGLEWVGEIYPRDGITDYADSVKGRFTISADTSKNTAYL

QMNSLRAEDTAVYYCARGGWHWRSGYSYYLDYWGQGTLVTVSSASTKGPSVFPLAPSSKSTSGGTAALGCLVKDYFPEPVTV

SWNSGALTSGVHTFPAVLQSSGL*SLSSVVTVPSSSLGTQTYICNVNHKPSNTKVDKKVEPKSCDKTHTCPPCPAPELLGGP

SVFLFPPKPKDTLMISRTPEVTCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVKGFYPSDIAVEWESNGQPENNYKTTPPVLDSDG

S*FLYSKLTVDKSRWQQGNVFSCSVMHEALHNHYTQKSLSLSPGK (B10 241TAG HC)

SEQ ID NO: 7

VEVQLVESGGGLVQPGGSLRLSCAASGFNTTTKSIHWVRQAPGKGLEWVGEIYPRDGITDYADSVKGRFTISADTSKNTAYL

QMNSLRAEDTAVYYCARGGWHWRSGYSYYLDYWGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKVDKKVEPKSCDKTHTCPPCPAPELLGGP

SV*LFPPKPKDTLMISRTPEVTCVVVDVSHEDPEVKFNWYVDGVEVHNAKTKPREEQYNSTRYVVSVLTVLHQDWLNGKEYK

CKVSNKALPAPIEKTISKAKGQPREPQVYTLPPSREEMTKNQVSLTCLVKGFYPSDIAVEWESNGQPENNYKTTPPVLDSDG

SFFLYSKLTVDKSRWQQGNVFSCSVMHEALHNHYTQKSLSLSPGK (H01 Y180TAG F404TAG HC)

SEQ ID NO: 8

MEVQLVESGGGLVQPGGSLRLSCAASGFNIRTQSIHWVRQAPGKGLEWIGDIFPIDGITDYADSVKGRFTISADTSKNTAYL

QMNSLRAEDTAVYYCARGSWSWPSGMDYYLDYWGQGTLVTVSSASTKGPSVFPLAPSSKSTSGGTAALGCLVKDYFPEPVTV

SWNSGALTSGVHTFPAVLQSSGL*SLSSVVTVPSSSLGTQTYICNVNHKPSNTKVDKKVEPKSCDKTHTCPPCPAPELLGGP

-continued

SVFLFPPKPKDTLMISRTPEVTCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVKGFYPSDIAVEWESNGQPENNYKTTPPVLDSDG

S*FLYSKLTVDKSRWQQGNVFSCSVMHEALHNHYTQKSLSLSPGK (7219 LC)

SEQ ID NO: 9

MDIQMTQSPSSVSASVGDRVTITCRASQGIGSWLAWYQQKPGKAPKLLIYAADRLQSGVPSRFSGSGSGTDFTLTISSLQPE

DFATYYCQQYHTYPLTFGGGTKVEIKRTVAAPSVFIFPPSDEQLKSGTASVVCLLNNFYPREAKVQWKVDNALQSGNSQESV

TEQDSKDSTYSLSSTLTLSKADYEKHKVYACEVTHQGLSSPVTKSFNRGEC (7219 F404TAG HC)

SEQ ID NO: 10

MQVQLVESGGGVVQPGRSLRLSCAASGFNFSDYGMHWVRQAPGKGLEWVAVIWYDGSISYYADSVKGRFTISRDNSKNTLYL

QMNSLRAEDTAVYYCARGGTVEHGAVYGTDVWGQGTTVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKGFYPSDIAVEWESNGQPENNYKTTPPVLDSDGS

*FLYSKLTVDKSRWQQGNVFSCSVMHEALHNHYTQKSLSLSPGK (αPD1 HC)

SEQ ID NO: 11

MEVQLVQSGAEVKKPGASVKVSCKASGYTFDSYGISWVRQAPGQGLEWMGWISYNGNTNYAQKLQRVTMTTDTSTNTAYMEL

RSLRSDDTAVYYCARDVDYGTGSGYWGQGTLVTVSSASTKGPSVFPLAPSSKSTSGGTAALGCLVKDYFPEPVTVSWNSGAL

TSGVHTFPAVLQSSGLYSLSSVVTVPSSSLGTQTYICNVNHKPSNTKVDKKVEPKSCDKTHTCPPCPAPELLGGPSVFLFPP

KPKDTLMISRTPEVTCEVVDVSHEDPEVKFNWYVDGVEVHNAKTKPREEQYNSTRYVVSVLTVLHQDWLNGKEYKCKVSNKA

LPAPIEKTISKAKGQPREPQVYTLPPSREEMTKNQVSLTCLVKGFYPSDIAVEWESNGQPENNYKTTPPVLDSDGSFFLYSK

LTVDKSRWQQGNVFSCSVMHEALHNHYTQKSLSLSPGK (αPD1 LC)

SEQ ID NO: 12

MSYELTQPPSVSVSPGQTARITCSGDALPKQYAYWYQQKPGQAPVMVIYKDTERPSGIPERFSGSSSGTKVTLTISGVQAED

EADYYCQSADNSITYRVFGGGTKVTVLGQPKAAPSVTLFPPSSEELQANKATLVCLISDFYPGAVTVAWKADSSPVKAGVET

TTPSKQSNNKYAASSYLSLTPEQWKSHRSYSCQVTHEGSTVEKTVAPTECS (αTim3 HC)

SEQ ID NO: 13

MEVQLVESGGGLVQPGGSLRLSCAASGFNIDRYYIHWVRQAPGKGLEWVAGITPVRGYTEYADSVKDRFTISADTSKNTAYL

QMNSLRAEDTAVYYCARGYVYRMWDSYDYWGQGTLVTVSSASTKGPSVFPLAPSSKSTSGGTAALGCLVKDYFPEPVTVSWN

SGALTSGVHTFPAVLQSSGLYSLSSVVTVPSSSLGTQTYICNVNHKPSNTKVDKKVEPKSCDKTHTCPPCPAPELLGGPSVF

LFPPKPKDTLMISRTPEVTCEVVDVSHEDPEVKFNWYVDGVEVHNAKTKPREEQY7NSTRYVVSVLTLVHQDWLNGKEYKCK

VSNKALPAPIEKTISKAKGQPREPQVYTLPPSREEMTKNQVSLTCLVKGFYPSDIAVEWESNGQPENNYKTTPPVLDSDGSF

FLYSKLTVDKSRWQQGNVFSCSVMHEALHNHYTQKSLSLSPGK (Timα3 LC)

SEQ ID NO: 14

MDIQMTQSPSSLSASVGDRVTITCRASQDVNTAVAWYQQKPGKAPKLLIYSASFLYSGVPSRFSGSRSGTDFTLTISSLQPE

DFATYYCQQHYTTPPTFGQGTKVEIKRTVAAPSVFIFPPSDEQLKSGTASVVCLLNNFYPREAKVQWKVDNALQSGNSQESV

TEQDSKDSTYSLSSTLTLSKADYEKHKVYACEVTHQGLSSPVTKSFNRGEC (αLAG3 HC)

SEQ ID NO: 15

MQVQLVESGGGVVQPGRSLRLSCAASGFTFSSYGMHWVRQAPGKGLEWVAVIWYDGSYKYYADSVKGRFTISRDNSKNTLYL

QMNSLRAEDTAVYYCAREEAPENWDYALDVWGQGTTVTVSSASTKGPSVFPLAPSSKSTSGGTAALGCLVKDYFPEPVTVSW

NSGALTSGVHTFPAVLQSSGLYSLSSVVTVPSSSLGTQTYICNVNHKPSNTKVDKKVEPKSCDKTHTCPPCPAPELLGGPSV

-continued

FLFPPKPKDTLMISRTPEVTCEVVDVSHEDPEVKFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKGFYPSDIAVEWESNGQPENNYKTTPPVLDSDGSF

FLYSKLTVDKSRWQQGNVFSCSVMHEALHNHYTQKSLSLSPGK (αLAG3 LC)

SEQ ID NO: 16

MEIVLTQSPGTLSLSPGERATLSCRASQSVSSSYLAWYQQKPGQAPRLLIYGASSRATGIPDRFSGSGSGTDFTLTISRLEP

EDFAVYYCQQYGRSPFSFGPGTKVDIKRTVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGEC (HC-RBS1; consensus RBS))

SEQ ID NO: 17

AGGAGGT (HC-RBS2; First mutant)

SEQ ID NO: 18

AAGAGAT (HC-RBS3; Second mutant)

SEQ ID NO: 19

AAAAGAT (LC-RBS1; canonical LC RBS)

SEQ ID NO: 20

AGGAGAT (LC-RBS2; First mutant)

SEQ ID NO: 21

AAGAGAT (LC-RBS3; Double mutant)

SEQ ID NO: 22

AAAAGAT (LC-RBS4; Triple mutant)

SEQ ID NO: 23

AAAATAT (H01 HC)

SEQ ID NO: 24

MEVQLVESGGGLVQPGGSLRLSCAASGFNIRTQSIHWVRQAPGKGLEWVIGDIFPIDGITDYADSVKGRFTISADTSKNTAY

LQMNSLRAEDTAVYYCARGSWSWPSGMDYYLDYWGQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGKEY

KCKVSNKALPAPIEKTISKAKGQPREPQVYTLPPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPGK (7219 HC)

SEQ ID NO: 25

MQVQLVESGGGVVQPGRSLRLSCAASGFNFSDYGMHWVRQAPGKGLEWVAVIWYDGSISYYADSVKGRFTISRDNSKNTLYL

QMNSLRAEDTAVYYCARGGTVEHGAVYGTDVWGQGTTVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKGFYPSDIAVEWESNGQPENNYKTTPPVLDSDGS

FFLYSKLTVDKSRWQQGNVFSCSVMHEALHNHYTQKSLSLSPGK (T7 promoter)

SEQ ID NO: 26

TAATACGACTCACTATAGGG (Trastuzumab HC)

SEQ ID NO: 27

MEVQLVESGGGLVQPGGSLRLSCAASGFNIKDTYIHWVRQAPGKGLEWVARIYPTNGYTRYADSVKGRFTISADTSKNTAYL

QMNSLRAEDTAVYYCSRWGGDGFYAMDYWGQGTLVTVSSASTKGPSVFPLAPSSKSTSGGTAALGCLVKDYFPEPVTVSWNS

GALTSGVHTFPAVLQSSGLYSLSSVVTVPSSSLGTQTYICNVNHKPSNTKVDKKVEPKSCDKTHTCPPCPAPELLGGPSVFL

-continued

FPPKPKDTLMISRPTEVTCVVVDVSHEDPEVKFNWYVDGVEVHNAKTKPREEQYNSTYRVVSVLTVLHQDWLNGKEYKCKVS

NKALPAPIEKTISKAKGQPREPQVYTLPPSREEMTKNQVSLTCLVKGFYPSDIAVEWESNGQPENNYKTTPPVLDSDGSFFL

YSKLTVDKSRWQQGNVFSCSVMHEALHNHYTQKSLSLSPGK (Ribosomal binding sequence, e.g., for heavy chain):

SEQ ID NO: 28

$AX_1GAGX_2T$ (wherein $X_1$ is A or G and $X_2$ is A or G), (Ribosomal binding sequence, e.g., for light chain):

SEQ ID NO: 29

$AX_1X_2AX_3AT$ (wherein $X_1$ is G or A, $X_2$ is G or A, and $X_3$ is G or T)

(T5 promoter sequence)

SEQ ID NO: 30

TAATTGTGAGCGGATAACAATTACGAGCTTCATGCACAGTGAAATCATGAAAAATTTATTTGCTTTGTGAGCGGATAACAAT

TATAATA (comprising SEQ ID NO: 17 (underlined)

(SEQ ID NO: 31

AAGGAGGTAAAAA (comprising SEQ ID NO: 20 (underlined)

SEQ ID NO: 32

AGGAGATATACAT (comprising SEQ ID NO: 21 (underlined)

SEQ ID NO: 33

AAGAGATATACAT (comprising SEQ ID NO: 22 (underlined)

SEQ ID NO: 34

AAAAGATATACAT (Operon sequence for B10 WT; the single-underlined (SEQ ID NO: 31) encodes the 5'UTR of the LC, and the double-underlined (SEQ ID NO: 32) encodes the 5'UTR of the HC)

SEQ ID NO: 35

AAGGAGGTAAAAAATGGACATTCAAATGACCCAGTCTCCGTCGTCACTGTCCGCATCCGTTGGCGACCGCGTTACCATCACG

TGCCGTGCGTCGCAAGATGTGAACACCGCCGTGGCGTGGTATCAGCAAAAACCGGGCAAAGCTCCGAAGCTGCTGATCTATT

CAGCCTCTTTCCTGTACTCGGGTGTTCCGTCCCGTTTCTCAGGCTCTCGCTCGGGTACGGATTTCACCCTGACTATTTCTTC

ACTGCAACCGGAAGATTTTGCGACGTACTACTGTCAGCAGCATTACACGACTCCGCCGACCTTTGGTCAGGGTACCAAGGTC

GAGATTAAGCGTACCGTGGCTGCACCATCCGTGTTTATCTTCCCTCCGTCTGATGAGCAGCTGAAATCCGGTACGGCGTCGG

TCGTCTGCTTGCTGAATAACTTCTATCCGCGTGAAGCGAAGGTGCAATGGAAGGTTGACAATGCCCTGCAGTCAGGTAACTC

CCAAGAGTCTGTTACCGAACAAGATTCGAAAGACTCAACCTACTCCCTGTCTTCGACGCTGACGTTGTCCAAAGCGGACTAT

GAGAAACACAAGGTTTACGCATGTGAAGTGACCCACCAGGGCCTGTCATCTCCGGTCACCAAATCATTTAATCGCGGTGAGT

GCTAAACCCCTTTAAGAAGGAGATATACATATGGAAGTTCAATTAGTCGAGTCTGGTGGCGGCTTAGTTCAACCTGGTGGTT

CATTGCGTCTGTCTTGCGCTGCATCGGGTTTTAACACCACCACGAAATCCATTCATTGGGTGCGCCAGGCCCCAGGTAAAGG

CCTGGAATGGGTCGGCGAGATCTACCCGCGTGACGGTATTACGGATTATGCGGATTCGGTGAAGGGTCGCTTCACCATCTCC

GCGGATACTAGCAAGAATACCGCGTATCTGCAGATGAACTCTCTGCGTGCAGAGGACACCGCGGTCTACTACTGTGCCCGTG

GCGGCTGGCACTGGCGCTCGGGTTATTCATACTATCTGGACTACTGGGGTCAGGGTACGTTGGTTACCGTGTCATCCGCGTC

AACCAAGGGTCCGTCGGTTTTTCCGCTGGCGCCGTCGTCAAAATCTACGTCCGGTGGTACCGCCGCTCTGGGTTGCCTGGTT

AAAGACTACTTTCCGGAGCCGGTCACGGTTTCGTGGAACTCTGGTGCCCTGACTTCTGGCGTCCACACGTTCCCAGCCGTTT

TGCAGTCATCCGGTCTGTACTCGTTGTCCTCTGTGGTCACGGTGCCGTCATCGTCTCTGGGCACCCAAACCTATATCTGCAA

TGTCAACCACAAACCGTCCAATACGAAAGTTGACAAAAAAGTCGAGCCGAAATCTTGCGACAAGACCCACACGTGCCCTCCG

TGCCCGGCACCGGAACTGCTGGGCGGTCCGTCGGTGTTCCTGTTCCCGCCGAAGCCGAAAGATACTCTGATGATCTCACGTA

CCCCGGAAGTCACGTGTGTTGTTGTTGACGTGTCACACGAAGATCCAGAGGTGAAATTCAATTGGTATGTGGACGGTGTCGA

AGTGCATAATGCCAAAACCAAACCGCGCGAGGAACAGTACAACTCCACCTACCGCGTCGTGTCGGTGTTGACCGTCCTGCAT

-continued

CAAGACTGGCTGAACGGTAAAGAGTACAAGTGCAAGGTTTCAAATAAGGCACTGCCTGCGCCGATTGAAAAGACCATCTCTA

AGGCAAAGGGCCAGCCGCGTGAGCCACAGGTGTATACCCTGCCGCCGTCGCGTGAAGAAATGACCAAGAACCAAGTTTCACT

GACGTGTCTGGTCAAGGGCTTTTATCCGTCCGATATTGCGGTGGAGTGGGAGTCTAATGGCCAGCCGGAAAACAATTACAAA

ACGACTCCGCCGGTGCTGGATTCCGACGGTTCGTTTTTCCTGTATTCCAAGCTGACCGTTGACAAATCACGTTGGCAGCAAG

GCAACGTTTTTTCTTGTTCGGTAATGCACGAAGCGCTGCACAATCATTACACCCAGAAATCACTGTCGTTGTCTCCGGGCAA

ATAA (Operon sequence for B10-MO-SDs (the single-underlined (SEQ ID NO: 31) encodes the 5'UTR of the LC and the double-underlined (SEQ ID NO: 32) encodes the 5'UTR of the HC)

SEQ ID NO: 36

AAGGAGGTAAAAAATGGACATTCAAATGACCCAGTCTCCGTCGTCACTGTCCGCATCCGTTGGCGACCGCGTTACCATCACG

TGCCGTGCGTCGCAAGATGTGAACACCGCCGTGGCGTGGTATCAGCAAAAACCGGGCAAAGCTCCGAAGCTGCTGATCTATT

CAGCCTCTTTCCTGTACTCGGGTGTTCCGTCCCGTTTCTCAGGCTCTCGCTCGGGTACGGATTTCACCCTGACTATTTCTTC

ACTGCAACCGGAAGATTTTGCGACGTACTACTGTCAGCAGCATTACACGACTCCGCCGACCTTTGGTCAGGGTACCAAGGTC

GAGATTAAGCGTACCGTGGCTGCACCATCCGTGTTTATCTTCCCTCCGTCTGATGAGCAGCTGAAATCCGGTACGGCGTCGG

TCGTCTGCTTGCTGAATAACTTCTATCCGCGTGAAGCGAAGGTGCAATGGAAGGTTGACAATGCCCTGCAGTCAGGTAACTC

CCAAGAGTCTGTTACCGAACAAGATTCGAAAGACTCAACCTACTCCCTGTCTTCGACGCTGACGTTGTCCAAAGCGGACTAT

GAGAAACACAAGGTTTACGCATGTGAAGTGACCCACCAGGGCCTGTCATCTCCGGTCACCAAATCATTTAATCGCGGTGAGT

GCTAACCCCCTAGCATAACCCCTTGGGGCCTCTAAACGGGTCTTGAGGGGTTTTTTGCCCCTGAGACGCGTCAATCGAGTTC

GTACCTAAGGGCGACACCCCCTAATTAGCCCGGATTTTTTTTGCGAAATTAATACGACTCACTATAGGGAGACCACAACGGT

TTCCCTCTAGAAATAATTTTGTTTAACTTTAAGAGGAGATATACATATGGAAGTTCAATTAGTCGAGTCTGGTGGCGGCTTA

GTTCAACCTGGTGGTTCATTGCGTCTGTCTTGCGCTGCATCGGGTTTTAACACCACCACGAAATCCATTCATTGGGTGCGCC

AGGCCCCAGGTAAAGGCCTGGAATGGGTCGGCGAGATCTACCCGCGTGACGGTATACGATTATGCGGATTCGGTGAAGGGTC

GCTTCACCATCTCCGCGGATACTAGCAAGAATACCGCGTATCTGCAGATGAACTCTCTGCGTGCAGAGGACACCGCGGTCTA

CTACTGTGCCCGTGGCGGCTGGCACTGGCGCTCGGGTTATTCATACTATCTGGACTACTGGGGTCAGGGTACGTTGGTTACC

GTGTCATCCGCGTCAACCAAGGGTCCGTCGGTTTTTCCGCTGGCGCCGTCGTCAAAATCTACGTCCGGTGGTACCGCCGCTC

TGGGTTGCCTGGTTAAAGACTACTTTCCGGAGCCGGTCACGGTTTCGTGGAACTCTGGTGCCCTGACTTCTGGCGTCCACAC

GTTCCCAGCCGTTTTGCAGTCATCCGGTCTGTACTCGTTGTCCTCTGTGGTCACGGTGCCGTCATCGTCTCTGGGCACCCAA

ACCTATATCTGCAATGTCAACCACAAACCGTCCAATACGAAAGTTGACAAAAAAGTCGAGCCGAAATCTTGCGACAAGACCC

ACACGTGCCCTCCGTGCCCGGCACCGGAACTGCTGGGCGGTCCGTCGGTGTTCCTGTTCCCGCCGAAGCCGAAAGATACTCT

GATGATCTCACGTACCCCGGAAGTCACGTGTGTTGTTGTTGACGTGTCACACGAAGATCCAGAGGTGAAATTCAATTGGTAT

GTGGACGGTGTCGAAGTGCATAATGCCAAAACCAAACCGCGCGAGGAACAGTACAACTCCACCTACCGCGTCGTGTCGGTGT

TGACCGTCCTGCATCAAGACTGGCTGAACGGTAAAGAGTACAAGTGCAAGGTTTCAAATAAGGCACTGCCTGCGCCGATTGA

AAAGACCATCTCTAAGGCAAAGGGCCAGCCGCGTGAGCCACAGGTGTATACCCTGCCGCCGTCGCGTGAAGAAATGACCAAG

AACCAAGTTTCACTGACGTGTCTGGTCAAGGGCTTTTATCCGTCCGATATTGCGGTGGAGTGGGAGTCTAATGGCCAGCCGG

AAAACAATTACAAAACGACTCCGCCGGTGCTGGATTCCGACGGTTCGTTTTTCCTGTATTCCAAGCTGACCGTTGACAAATC

ACGTTGGCAGCAAGGCAACGTTTTTTCTTGTTCGGTAATGCACGAAGCGCTGCACAATCATTACACCCAGAAATCACTGTCG

TTGTCTCCGGGCAAATAATGAGTCGACCGGCTGCTAACAAAGCCCGAAAGGAAGCTGAGTTGGCTGCTGCCACCGCTGAGCA

ATAACTAGCATAACCCCTTGGGGCCTCTAAACGGGTCTTGAGGGGTTTTT (Operon sequence for B10-MO-SDm; (the single-underlined (SEQ ID NO: 31) encodes the 5'UTR of the LC, and the double-underlined (SEQ ID NO: 33) encodes the 5'UTR of the HC)

SEQ ID NO: 37

AAGGAGGTAAAAAATGGACATTCAAATGACCCAGTCTCCGTCGTCACTGTCCGCATCCGTTGGCGACCGCGTTACCATCACG

TGCCGTGCGTCGCAAGATGTGAACACCGCCGTGGCGTGGTATCAGCAAAAACCGGGCAAAGCTCCGAAGCTGCTGATCTATT

-continued

CAGCCTCTTTCCTGTACTCGGGTGTTCCGTCCCGTTTCTCAGGCTCTCGCTCGGGTACGGATTTCACCCTGACTATTTCTTC

ACTGCAACCGGAAGATTTTGCGACGTACTACTGTCAGCAGCATTACACGACTCCGCCGACCTTTGGTCAGGGTACCAAGGTC

GAGATTAAGCGTACCGTGGCTGCACCATCCGTGTTTATCTTCCCTCCGTCTGATGAGCAGCTGAAATCCGGTACGGCGTCGG

TCGTCTGCTTGCTGAATAACTTCTATCCGCGTGAAGCGAAGGTGCAATGGAAGGTTGACAATGCCCTGCAGTCAGGTAACTC

CCAAGAGTCTGTTACCGAACAAGATTCGAAAGACTCAACCTACTCCCTGTCTTCGACGCTGACGTTGTCCAAAGCGGACTAT

GAGAAACACAAGGTTTACGCATGTGAAGTGACCCACCAGGGCCTGTCATCTCCGGTCACCAAATCATTTAATCGCGGTGAGT

GCTAACCCCCTAGCATAACCCCTTGGGGCCTCTAAACGGGTCTTGAGGGGTTTTTTGCCCCTGAGACGCGTCAATCGAGTTC

GTACCTAAGGGCGACACCCCCTAATTAGCCCGGATTTTTTTTGCGAAATTAATACGACTCACTATAGGGAGACCACAACGGT

TTCCCTCTAGAAATAATTTTGTTTAACTTTAAGAAGAGATATACATATGGAAGTTCAATTAGTCGAGTCTGGTGGCGGCTAG

TTCAACCTGGTGGTTCATTGCGTCTGTCTTGCGCTGCATCGGGTTTTAACACCACCACGAAATCCATTCATTGGGTGCGCCA

GGCCCCAGGTAAAGGCCTGGAATGGGTCGGCGAGATCTACCCGCGTGACGGTATTACGGATTATGCGGATTCGGTGAAGGGT

CGCTTCACCATCTCCGCGGATACTAGCAAGAATACCGCGTATCTGCAGATGAACTCTCTGCGTGCAGAGGACACCGCGGTCT

ACTACTGTGCCCGTGGCGGCTGGCACTGGCGCTCGGGTTATTCATACTATCTGGACTACTGGGGTCAGGGTACGTTGGTTAC

CGTGTCATCCGCGTCAACCAAGGGTCCGTCGGTTTTTCCGCTGGCGCCGTCGTCAAAATCTACGTCCGGTGGTACCGCCGCT

CTGGGTTGCCTGGTTAAAGACTACTTTCCGGAGCCGGTCACGGTTTCGTGGAACTCTGGTGCCCTGACTTCTGGCGTCCACA

CGTTCCCAGCCGTTTTGCAGTCATCCGGTCTGTACTCGTTGTCCTCTGTGGTCACGGTGCCGTCATCGTCTCTGGGCACCCA

AACCTATATCTGCAATGTCAACCACAAACCGTCCAATACGAAAGTTGACAAAAAAGTCGAGCCGAAATCTTGCGACAAGACC

CACACGTGCCCTCCGTGCCCGGCACCGGAACTGCTGGGCGGTCCGTCGGTGTTCCTGTTCCCGCCGAAGCCGAAAGATACTC

TGATGATCTCACGTACCCCGGAAGTCACGTGTGTTGTTGTTGACGTGTCACACGAAGATCCAGAGGTGAAATTCAATTGGTA

TGTGGACGGTGTCGAAGTGCATAATGCCAAAACCAAACCGCGCGAGGAACAGTACAACTCCACCTACCGCGTCGTGTCGGTG

TTGACCGTCCTGCATCAAGACTGGCTGAACGGTAAAGAGTACAAGTGCAAGGTTTCAAATAAGGCACTGCCTGCGCCGATTG

AAAAGACCATCTCTAAGGCAAAGGGCCAGCCGCGTGAGCCACAGGTGTATACCCTGCCGCCGTCGCGTGAAGAAATGACCAA

GAACCAAGTTTCACTGACGTGTCTGGTCAAGGGCTTTTATCCGTCCGATATTGCGGTGGAGTGGGAGTCTAATGGCCAGCCG

GAAAACAATTACAAAACGACTCCGCCGGTGCTGGATTCCGACGGTTCGTTTTTCCTGTATTCCAAGCTGACCGTTGACAAAT

CACGTTGGCAGCAAGGCAACGTTTTTTCTTGTTCGGTAATGCACGAAGCGCTGCACAATCATTACACCCAGAAATCACTGTC

GTTGTCTCCGGGCAAATAATGAGTCGACCGGCTGCTAACAAAGCCCGAAAGGAAGCTGAGTTGGCTGCTGCCACCGCTGAGC

AATAACTAGCATAACCCCTTGGGGCCTCTAAACGGGTCTTGAGGGGTTTTT (Operon sequence for B10-MO-SDw; (the single-underlined (SEQ ID NO: 31) encodes the 5'UTR of the LC, and the double-underlined (SEQ ID NO: 34) encodes the 5'UTR of the HC)

SEQ ID NO: 38

AAGGAGGTAAAAAATGGACATTCAAATGACCCAGTCTCCGTCGTCACTGTCCGCATCCGTTGGCGACCGCGTTACCATCACG

TGCCGTGCGTCGCAAGATGTGAACACCGCCGTGGCGTGGTATCAGCAAAAACCGGGCAAAGCTCCGAAGCTGCTGATCTATT

CAGCCTCTTTCCTGTACTCGGGTGTTCCGTCCCGTTTCTCAGGCTCTCGCTCGGGTACGGATTTCACCCTGACTATTTCTTC

ACTGCAACCGGAAGATTTTGCGACGTACTACTGTCAGCAGCATTACACGACTCCGCCGACCTTTGGTCAGGGTACCAAGGTC

GAGATTAAGCGTACCGTGGCTGCACCATCCGTGTTTATCTCCCTCCGTCTGATGAGCAGCTGAAATCCGGTACGGCGTCGGT

CGTCTGCTTGCTGAATAACTTCTATCCGCGTGAAGCGAAGGTGCAATGGAAGGTTGACAATGCCCTGCAGTCAGGTAACTCC

CAAGAGTCTGTTACCGAACAAGATTCGAAAGACTCAACCTACTCCCTGTCTTCGACGCTGACGTTGTCCAAAGCGGACTATG

AGAAACACAAGGTTTACGCATGTGAAGTGACCCACCAGGGCCTGTCATCTCCGGTCACCAAATCATTTAATCGCGGTGAGTG

CTAACCCCCTAGCATAACCCCTTGGGGCCTCTAAACGGGTCTTGAGGGGTTTTTTGCCCCTGAGACGCGTCAATCGAGTTCG

TACCTAAGGGCGACACCCCCTAATTAGCCCGGATTTTTTTTGCGAAATTAATACGACTCACTATAGGGAGACCACAACGGTT

TCCCTCTAGAAATAATTTTGTTTAACTTTAAGAAAAGATATACATATGGAAGTTCAATTAGTCGAGTCTGGTGGCGGCTTAG

-continued

TTCAACCTGGTGGTTCATTGCGTCTGTCTTGCGCTGCATCGGGTTTTAACACCACCACGAAATCCATTCATTGGGTGCGCCA

GGCCCCAGGTAAAGGCCTGGAATGGGTCGGCGAGATCTACCCGCGTGACGGTATTACGGATTATGCGGATTCGGTGAAGGGT

CGCTTCACCATCTCCGCGGATACTAGCAAGAATACCGCGTATCTGCAGATGAACTCTCTGCGTGCAGAGGACACCGCGGTCT

ACTACTGTGCCCGTGGCGGCTGGCACTGGCGCTCGGGTTATTCATACTATCTGGACTACTGGGGTCAGGGTACGTTGGTTAC

CGTGTCATCCGCGTCAACCAAGGGTCCGTCGGTTTTTCCGCTGGCGCCGTCGTCAAAATCTACGTCCGGTGGTACCGCCGCT

CTGGGTTGCCTGGTTAAAGACTACTTTCCGGAGCCGGTCACGGTTTCGTGGAACTCTGGTGCCCTGACTTCTGGCGTCCACA

CGTTCCCAGCCGTTTTGCAGTCATCCGGTCTGTACTCGTTGTCCTCTGTGGTCACGGTGCCGTCATCGTCTCTGGGCACCCA

AACCTATATCTGCAATGTCAACCACAAACCGTCCAATACGAAAGTTGACAAAAAAGTCGAGCCGAAATCTTGCGACAAGACC

CACACGTGCCCTCCGTGCCCGGCACCGGAACTGCTGGGCGGTCCGTCGGTGTTCCTGTTCCCGCCGAAGCCGAAAGATACTC

TGATGATCTCACGTACCCCGGAAGTCACGTGTGTTGTTGTTGACGTGTCACACGAAGATCCAGAGGTGAAATTCAATTGGTA

TGTGGACGGTGTCGAAGTGCATAATGCCAAAACCAAACCGCGCGAGGAACAGTACAACTCCACCTACCGCGTCGTGTCGGTG

TTGACCGTCCTGCATCAAGACTGGCTGAACGGTAAAGAGTACAAGTGCAAGGTTTCAAATAAGGCACTGCCTGCGCCGATTG

AAAGACCATCTCTAAGGCAAAGGGCCAGCCGCGTGAGCCACAGGTGTATACCCTGCCGCCGTCGCGTGAAGAAATGACCAAG

AACCAAGTTTCACTGACGTGTCTGGTCAAGGGCTTTTATCCGTCCGATATTGCGGTGGAGTGGGAGTCTAATGGCCAGCCGG

AAAACAATTACAAAACGACTCCGCCGGTGCTGGATTCCGACGGTTCGTTTTTCCTGTATTCCAAGCTGACCGTTGACAAATC

ACGTTGGCAGCAAGGCAACGTTTTTTCTTGTTCGGTAATGCACGAAGCGCTGCACAATCATTACACCCAGAAATCACTGTCG

TTGTCTCCGGGCAAATAATGAGTCGACCGGCTGCTAACAAAGCCCGAAAGGAAGCTGAGTTGGCTGCTGCCACCGCTGAGCA

ATAACTAGCATAACCCCTTGGGGCCTCTAAACGGGTCTTGAGGGGTTTTT

What is claimed is:

1. An *E. coli* cell with an oxidative cytoplasm, wherein the *E. coli* cell comprises (a) a coding sequence encoding a full-length antibody heavy chain (HC); and (b) a coding sequence encoding a full-length antibody light chain (LC);

wherein the cell comprises an expression vector comprising a first ribosome-binding site for translation of the HC and a second ribosome-binding site for translation of the LC, and wherein the HC and LC are not exported outside of the cytoplasm of the cell, and wherein the cell produces more LC than HC.

2. The *E. coli* cell of claim 1, wherein the molar ratio of HC and LC produced ranges from 1:1 to 1:3.

3. The *E. coli* cell of claim 1, wherein the first ribosomal binding site is SEQ ID NO: 28 and the second ribosomal binding site is SEQ ID NO: 29.

4. The *E. coli* cell of claim 1, wherein the coding sequences for the HC and LC are operably linked to regulatory elements that direct expression in the cytoplasm of the *E. coli* cell.

5. The *E. coli* cell of claim 1, wherein the cell is capable of assembling the expressed HC and LC under non-reducing conditions to form a full-length antibody.

6. The *E. coli* cell of claim 1, wherein the *E. coli* cell, when cultured under conditions permitting expression, produces a full-length antibody comprising said HC and LC in an amount of at least about 200 mg per liter of culture medium.

7. The *E. coli* cell of claim 1, wherein expression of the HC and/or LC is controlled by a promoter selected from the group consisting of a T7 promoter, a promoter having substantially similar promoter strength as a T7 promoter, a T5 promoter, or a promoter having substantially similar promoter strength as a T5 promoter.

8. The *E. coli* cell of claim 1, wherein the cell comprises:
(a) a plasmid comprising a bicistronic operon including the coding sequence for the HC and the coding sequence for the LC, or
(b) a plasmid comprising a first monocistronic operon for the HC and a second monocistronic operon for the LC.

9. The *E. coli* cell of claim 8, wherein:
(a) the bicistronic operon comprises a promoter that drives expression of both the HC and LC,
wherein the promoter is a T7 promoter or a promoter having substantially similar promoter strength as a T7 promoter, or
(b) the first or second monocistronic operon comprises a T7 promoter.

10. The *E. coli* cell of claim 9, wherein:
(a) the bicistronic operon comprises a T7 terminator, or
(b) the first or second monocistronic operon comprises a T7 terminator.

11. An *E. coli* cell with an oxidative cytoplasm, wherein the *E. coli* cell comprises an expression vector comprising
(a) a coding sequence encoding a full-length antibody heavy chain (HC); and
(b) a coding sequence encoding a full-length antibody light chain (LC)
(c) a first ribosome-binding site for translation of the HC, wherein
wherein:
the first ribosomal binding site is transcribed from a DNA sequence selected from the group consisting of SEQ ID NO: 17-19, and
(d) a second ribosome-binding site for translation of the LC, wherein the second ribosomal binding site is transcribed from a DNA sequence selected from the group consisting of SEQ ID NO: 20-23,
and wherein the cell produces more LC than HC.

12. The *E. coli* cell of claim 11, wherein the first ribosomal binding site has a sequence of SEQ ID NO: 17 or SEQ ID NO: 18.

13. The *E. coli* cell of claim 1, wherein the HC and/or LC of the full-length antibody comprises at least one non-natural amino acid.

14. The *E. coli* cell of claim 13, wherein the coding sequence for the HC and/or the coding sequence for the LC has been modified to comprise at least one non-natural amino acid codon, said codon not resulting in the incorporation of any naturally occurring amino acid.

15. The *E. coli* cell of claim 13, further comprising at least one tRNA charged with a non-natural amino acid, said tRNA containing an anticodon complementary to at least one non-natural amino acid codon present in the coding sequence for the HC and/or LC.

16. The *E. coli* cell of claim 15, wherein said non-natural amino acid codon is the amber codon TAG.

17. The *E. coli* cell of claim 15, wherein said non-natural amino acid is selected from the group consisting of para-methylazido-L-phenylalanine (pAMF), AEK, and pAcF.

18. The *E. coli* cell of claim 14, wherein the codon immediately 3' to at least one non-natural amino acid codon is codon optimized.

19. The *E. coli* cell of claim 1, wherein the full-length antibody produced is selected from the group consisting of a B10 antibody, an H01 antibody, a 7219 antibody, an anti-PD1 antibody, an anti-Tim3 antibody, an anti-LAG3 antibody, and an anti-Her2 antibody.

20. The *E. coli* cell of claim 19, wherein the coding sequence for the HC of the B10 antibody contains a mutation relative to SEQ ID NO: 1, said mutation resulting in a codon for a natural amino acid selected from F412, Y188, and F249, being substituted with a non-natural amino acid codon, and wherein a non-natural amino acid is introduced to the HC by charging a tRNA complementary to the non-natural amino acid codon.

21. The *E. coli* cell of claim 19, wherein the coding sequence for the LC of the B10 antibody or the coding sequence for the LC of trastuzumab contains at least one mutation relative to SEQ ID NO: 2, said mutation resulting in a codon for a natural amino acid selected from K43 or E162 being substituted with a non-natural amino acid codon.

22. A method to produce a full-length antibody comprising a heavy chain (HC) and a light chain (LC), wherein the method comprises:
culturing *E. coli* cells of claim 1, thereby producing the full-length antibody.

23. The *E. coli* cell of claim 1, wherein the HC and/or LC of the full-length antibody comprises at least one non-natural amino acid.

24. The *E. coli* cell of claim 1, wherein said non-natural amino acid is selected from the group consisting of para-methylazido-L-phenylalanine (pAMF), AEK, and pAcF.

25. The *E. coli* cell of claim 1, wherein the signal peptides of HC and LC are modified such that they are not exported outside the cytoplasm.

* * * * *